United States Patent
Teige

(10) Patent No.: US 9,266,952 B2
(45) Date of Patent: Feb. 23, 2016

(54) ANTIBODIES AGAINST ROR1 AND USES THEREOF

(75) Inventor: Ingrid Teige, Lund (SE)

(73) Assignee: KANCERA AB, Solna (SE)

( * ) Notice: Subject to any disclaimer, the term of this patent is extended or adjusted under 35 U.S.C. 154(b) by 164 days.

(21) Appl. No.: 13/992,704

(22) PCT Filed: Dec. 12, 2011

(86) PCT No.: PCT/EP2011/072490
§ 371 (c)(1),
(2), (4) Date: Jun. 24, 2013

(87) PCT Pub. No.: WO2012/076727
PCT Pub. Date: Jun. 14, 2012

(65) Prior Publication Data
US 2013/0281922 A1      Oct. 24, 2013

Related U.S. Application Data

(63) Continuation-in-part of application No. PCT/EP2011/003017, filed on Jun. 17, 2011.

(30) Foreign Application Priority Data

Dec. 10, 2010   (GB) .................................. 1020995.5

(51) Int. Cl.
*C07K 16/28*     (2006.01)
*C07K 16/30*     (2006.01)
*A61K 39/00*     (2006.01)

(52) U.S. Cl.
CPC ............. *C07K 16/28* (2013.01); *C07K 16/2803* (2013.01); *A61K 2039/505* (2013.01); *C07K 2317/21* (2013.01); *C07K 2317/622* (2013.01); *C07K 2317/73* (2013.01); *C07K 2317/732* (2013.01); *C07K 2317/76* (2013.01); *C07K 2317/92* (2013.01)

(58) Field of Classification Search
None
See application file for complete search history.

(56) References Cited

FOREIGN PATENT DOCUMENTS

| EP | 2316491 A1 | 5/2011 |
|---|---|---|
| GB | 2476293 A | 6/2011 |
| WO | WO 2008/076868 A2 | 6/2008 |
| WO | WO 2010/008069 A1 | 1/2010 |
| WO | WO 2010/124188 A1 | 10/2010 |
| WO | WO 2011/054007 A1 | 5/2011 |
| WO | WO 2011/079902 A2 | 7/2011 |

OTHER PUBLICATIONS

MacCallum et al., Antibody-antigen interactions:contact analysis and binding site topography, J. Mol. Biol. 262:732-745, 1996.*
DaneshManesh, Ror1, a cell surface receptor tyrosine kinase is expressed in choronic lyphocytic leukemia and may serve as a putative target for therapy, Int. J. Cancer, 123:1190-1195, 2008.*

(Continued)

*Primary Examiner* — Claire Kaufman
(74) *Attorney, Agent, or Firm* — Knobbe, Martens, Olson & Bear, LLP

(57) ABSTRACT

The invention relates to antibodies for inducing cell death by the specific binding of (ROR1), domains thereof or nucleotide molecules encoding (ROR1). There are also provided methods involving and uses of the antibodies of the invention.

6 Claims, 34 Drawing Sheets

(56) References Cited

OTHER PUBLICATIONS

Chen et al., Enhancement and desruction of antibody function by somatic mutation: unequal occurrence is controlled by V gene combinatorial association, EMBO J., 14 (12): 2784-2794, 1995.*

Baskar, S et al. 2008 "Targeting human B cell chronic lymphocytic leukemia with a monoclonal antibody specific for the Receptor Tyrosine Kinase ROR1" Journal of Immunotherapy 31(9): p. 969 (Meeting Abstract).

Castells, M.C. et al. 2008 "Hypersensitivity reactions to chemotherapy: Outcomes and safety of rapid desensitization in 413 cases" *J Allergy and Clinical Immunol* 122(3): 574-580.

Choudhury, A. et al. 2010 "Silencing of ROR1 and FMOD with siRNA results in apoptosis of CLL cells" *British Journal of Haematology* 151(4): 327-335.

Fukuda, T. et al. 2008 "Antisera induced by infusions of autologous Ad-CD154-leukemia B cells identify ROR1 as an oncofetal antigen and receptor for Wnt5a" *Proc Natl Aced Sci USA* 105: 3047-3052.

MacKeigan J.P. et al. 2005 "Sensitized RNAi screen of human kinases and phosphatases identifies new regulators of apoptosis and chemoresistance" *Nature Cell Biology* 7(6): 591-600.

Rabbani, H. et al. 2011 "ROR1 Targeting monoclonal antibodies induced apoptosis of chronic lymphocytic leukemia cells—a potential novel therapeutic approach" ASH Annual Meeting and Exposition, San Diego, CA, Abstract No. 916', 52nd Annual Meeting, vol. 116(21), Nov. 19, 2010.

Yang, J. et al. 2011 "Therapeutic Potential and Challenges of Targeting Receptor Tyrosine Kinase ROR1 with Monoclonal Antibodies in B-Cell Malignancies" *PLOS One* 6: pp. 1-15.

* cited by examiner

IgG1-CH

ASTKGPSVFPLAPSSKSTSGGTAALGCLVKDYFPEPVTVSWNSGALTSGVHTFPAVL
QSSGLYSLSSVVTVPSSSLGTQTYICNVNHKPSNTKVDKKVEPKSCDKTHTCPPCPA
PELLGGPSVFLFPPKPKDTLMISRTPEVTCVVVDVSHEDPEVKFNWYVDGVEVHNAK
TKPREEQYNSTYRVVSVLTVLHQDWLNGKEYKCKVSNKALPAPIEKTISKAKGQPRE
PQVYTLPPSRDELTKNQVSLTCLVKGFYPSDIAVEWESNGQPENNYKTTPPVLDSDG
SFFLYSKLTVDKSRWQQGNVFSCSVMHEALHNHYTQKSLSLSPGK

λ-CL

QPKAAPSVTLFPPSSEELQANKATLVCLISDFYPGAVTVAWKADSSPVKAGVETTTP
SKQSNNKYAASSYLSLTPEQWKSHRSYSCQVTHEGSTVEKTVAPTECS

*Figure 3*

ROR1-007-B03-VH

EVQLLESGGGLVQPGGSLRLSCAASGFT FSNYWMHWVRQAPG KGLEWV SAISGSGGSTYYADSV
FrH1                         CDRH1           FrH2   CDRH2

KGR FTISRDNSKNTLYLQMNSLRAEDTAVYYC ARQGRAVTLDY WGQGTLVTVSS
    FrH3                          CDRH3       FrH4

ROR1-007-B03-VL

QSVLTQPPSASGTPGQRVTIS CSGSRSNIGSNSVH WYQQLPGTAPKLLIY SNNQRPS GVPDRFSGSK
FrL1                  CDRL1          FrL2            CDRL2

SGTSASLAISGLRSEDEADYY CSSYTSSSTLL FGGGTKLTVLG
FrL3                  CDRL3       FrL4

ROR1-007-B03-VH

GAGGTGCAGCTGTTGGAGTCTGGGGGAGGCTTGGTACAGCCTGGGGGGTCCCTGAGACTCTCCTGTG
CAGCCTCTGGATTCACCTTCAGTAACTACTGGATGCACTGGGTCCGCCAAGCTCCAGGGAAGGGGCT
GGAGTGGGTCTCAGCTATTAGTGGTAGTGGTGGTAGCACATACTACGCAGACTCCGTGAAGGGCCG
GTTCACCATCTCCAGAGACAATTCCAAGAACACGCTGTATCTGCAAATGAACAGCCTGAGAGCCGA
GGACACTGCCGTGTATTACTGTGCGAGACAGGGACGTGCAGTTACCCTTGACTACTGGGGCCAGGGT
ACACTGGTCACCGTGAGCTCA

ROR1-007-B03-VL

CAGTCTGTGCTGACTCAGCCACCCTCAGCGTCTGGGACCCCCGGGCAGAGGGTCACCATCTCTTGTT
CTGGAAGCAGGTCCAACATCGGGAGTAACTCCGTACACTGGTATCAGCAGCTCCCAGGAACGGCCC
CCAAACTCCTCATCTATAGTAATAATCAGCGGCCCTCAGGGGTCCCTGACCGATTCTCTGGCTCCAA
GTCTGGCACCTCAGCCTCCCTGGCCATCAGTGGGCTCCGGTCCGAGGATGAGGCTGATTATTACTGC
AGCTCATATACAAGCAGCAGCACTCTGCTATTCGGCGGAGGAACCAAGCTGACGGTCCTAGGT

*Figure 4*

ROR1-007-C08-VH

EVQLLESGGGLVQPGGSLRLSCAASGFT FSSYDMAWVRQAPG KGLEWV SGVSWNGSRTHYADSVK
  FrH1                       CDRH1           FrH2  CDRH2

GR FTISRDNSKNTLYLQMNSLRAEDTAVYYC ARDQDLSGWYPGYFDY WGQGTLVTVSS
   FrH3                          CDRH3            FrH4

ROR1-007-C08-VL

QSVLTQPPSASGTPGQRVTIS CSGSSSDMGNYAVS WYQQLPGTAPKLLIY GNSNRPS GVPDRFSGS
  FrL1                CDRL1           FrL2            CDRL2

KSGTSASLAISGLRSEDEADYY CSSYTSSRTVV FGGGTKLTVLG
  FrL3                  CDRL3       FrL4

ROR1-007-C08-VH

GAGGTGCAGCTGTTGGAGTCTGGGGGAGGCTTGGTACAGCCTGGGGGGTCCCTGAGACTCTCCTGTG
CAGCCTCTGGATTCACCTTTAGCAGCTATGACATGGCCTGGGTCCGCCAGGCTCCAGGGAAGGGGCT
GGAGTGGGTATCGGGTGTTAGTTGGAATGGCAGTAGGACGCACTATGCAGACTCTGTGAAGGGCCG
ATTCACCATCTCCAGAGACAATTCCAAGAACACGCTGTATCTGCAAATGAACAGCCTGAGAGCCGA
GGACACTGCCGTGTATTACTGTGCGAGAGATCAAGATCTCAGTGGCTGGTACCCGGGGTACTTTGAC
TACTGGGGCCAGGGTACACTGGTCACCGTGAGCTCA

ROR1-007-C08-VL

CAGTCTGTGCTGACTCAGCCACCCTCAGCGTCTGGGACCCCCGGGCAGAGGGTCACCATCTCCTGCT
CTGGAAGCAGCTCCGACATGGGGAATTATGCGGTATCCTGGTATCAGCAGCTCCCAGGAACGGCCC
CCAAACTCCTCATCTATGGTAACAGCAATCGGCCCTCAGGGGTCCCTGACCGATTCTCTGGCTCCAA
GTCTGGCACCTCAGCCTCCCTGGCCATCAGTGGGCTCCGGTCCGAGGATGAGGCTGATTATTACTGC
AGCTCATATACAAGCAGTCGCACTGTGGTGTTCGGCGGAGGAACCAAGCTGACGGTCCTAGGT

*Figure 5*

ROR1-007-E06-VH

EVQLLESGGGLVQPGGSLRLSCAASGFT FSSYAMSWVRQAPG KGLEWV SAIGAGGGTYYADSVKG
　　　　FrH1　　　　　　　　　　 CDRH1　　　　　 FrH2　　　　 CDRH2

R FTISRDNSKNTLYLQMNSLRAEDTAVYYC ASGGSWELPDY WGQGTLVTVSS
　　　　FrH3　　　　　　　　　　　　 CDRH3　　　　 FrH4

ROR1-007-E06-VL

QSVLTQPPSASGTPGQRVTIS CSGSSSNIGSNTVN WYQQLPGTAPKLLIY YDDLLPS GVPDRFSGSKS
　　　　FrL1　　　　　　 CDRL1　　　　　　　 FrL2　　　　 CDRL2

GTSASLAISGLRSEDEADYY CSSHTTTSTFWV FGGGTKLTVLG
　　　　FrL3　　　　　 CDRL3　　　　　 FrL4

ROR1-007-E06-VH

GAGGTGCAGCTGTTGGAGTCTGGGGGAGGCTTGGTACAGCCTGGGGGGTCCCTGAGACTCTCCTGTG
CAGCCTCTGGATTCACCTTTAGCAGCTATGCCATGAGCTGGGTCCGCCAGGCTCCAGGGAAGGGGCT
GGAGTGGGTATCAGCTATTGGTGCTGGTGGTGGCACATACTATGCAGACTCCGTGAAGGGCCGATTC
ACCATCTCCAGAGACAATTCCAAGAACACGCTGTATCTGCAAATGAACAGCCTGAGAGCCGAGGAC
ACTGCCGTGTATTACTGTGCGAGTGGCGGATCGTGGGAGCTACCTGACTACTGGGGCCAGGGTACAC
TGGTCACCGTGAGCTCA

ROR1-007-E06-VL

CAGTCTGTGCTGACTCAGCCACCCTCAGCGTCTGGGACCCCCGGGCAGAGGGTCACCATCTCTTGTT
CTGGAAGCAGCTCCAACATCGGAAGTAATACTGTAAACTGGTATCAGCAGCTCCCAGGAACGGCCC
CCAAACTCCTCATCTATTATGATGATCTGCTGCCCTCAGGGGTCCCTGACCGATTCTCTGGCTCCAAG
TCTGGCACCTCAGCCTCCCTGGCCATCAGTGGGCTCCGGTCCGAGGATGAGGCTGATTATTACTGCA
GCTCACATACAACCACCAGCACTTTTTGGGTGTTCGGCGGAGGAACCAAGCTGACGGTCCTAGGT

*Figure 6*

ROR1-007-H03-VH

EVQLLESGGGLVQPGGSLRLSCAASGFT|FSPYSMNWVRQAPG|KGLEWV|SSISSSSTIYYADSVKGRF|
      FrH1                          CDRH1              FrH2           CDRH2

TISRDNSKNTLYLQMNSLRAEDTAVYYC|ARKTLALDI|WGQGTLVTVSS
            FrH3                     CDRH3       FrH4

ROR1-007-H03-VL

QSVLTQPPSASGTPGQRVTIS|CTGSSSNIGARYDVH|WYQQLPGTAPKLLIY|SDDQRPS|GVPDRFSGS
          FrL1                   CDRL1             FrL2         CDRL2

KSGTSASLAISGLRSEDEADYY|CQSYDSSLSGWV|FGGGTKLTVLG
       FrL3                CDRL3         FrL4

ROR1-007-H03-VH

GAGGTGCAGCTGTTGGAGTCTGGGGGAGGCTTGGTACAGCCTGGGGGGTCCCTGAGACTCTCCTGTG
CAGCCTCTGGATTCACCTTTAGTCCTTATAGCATGAACTGGGTCCGCCAGGCTCCAGGGAAGGGGCT
GGAGTGGGTCTCATCCATTAGTAGTAGTAGTACCATATACTACGCAGACTCTGTGAAGGGCCGATTC
ACCATCTCCAGAGACAATTCCAAGAACACGCTGTATCTGCAAATGAACAGCCTGAGAGCCGAGGAC
ACTGCCGTGTATTACTGTGCGAGAAAAACCTTGGCTCTTGATATCTGGGGCCAAGGTACACTGGTCA
CCGTGAGCTCA

ROR1-007-H03-VL

CAGTCTGTGCTGACTCAGCCACCCTCAGCGTCTGGGACCCCCGGGCAGAGGGTCACCATCTCCTGCA
CTGGGAGCAGCTCCAACATCGGGGCACGTTATGATGTTCACTGGTATCAGCAGCTCCCAGGAACGGC
CCCCAAACTCCTCATCTATAGTGATGATCAGCGGCCCTCAGGGGTCCCTGACCGATTCTCTGGCTCC
AAGTCTGGCACCTCAGCCTCCCTGGCCATCAGTGGGCTCCGGTCCGAGGATGAGGCTGATTATTACT
GCCAGTCCTACGACAGCAGCCTGAGTGGTTGGGTGTTCGGCGGAGGAACCAAGCTGACGGTCCTAG
GT

*Figure 7*

ROR1-008-A03-VH

EVQLLESGGGLVQPGGSLRLSCAASGFT FSNAWMS WVRQAPG KGLEWV SGITGSGDSTYYADSVK
        FrH1                 CDRH1        FrH2        CDRH2

GR FTISRDNSKNTLYLQMNSLRAEDTAVYYC ATGGDTSGYGPH WGQGTLVTVSS
              FrH3                    CDRH3        FrH4

ROR1-008-A03-VL

QSVLTQPPSASGTPGQRVTIS CSGSSSNIGSNYVY WYQQLPGTAPKLLIY DNNKRPS GVPDRFSGSK
       FrL1              CDRL1          FrL2        CDRL2

SGTSASLAISGLRSEDEADYY CQSYDDTLSVVV FGGGTKLTVLG
     FrL3            CDRL3       FrL4

ROR1-008-A03-VH

GAGGTGCAGCTGTTGGAGTCTGGGGGAGGCTTGGTACAGCCTGGGGGGTCCCTGAGACTCTCCTGTG
CAGCCTCTGGATTCACCTTCAGTAACGCCTGGATGAGCTGGGTCCGCCAGGCTCCAGGGAAGGGGCT
GGAGTGGGTCTCAGGTATTACTGGTAGTGGTGATAGCACATACTACGCAGACTCCGTGAAGGGCCG
CTTCACCATCTCCAGAGACAATTCCAAGAACACGCTGTATCTGCAAATGAACAGCCTGAGAGCCGA
GGACACTGCCGTGTATTACTGTGCGACGGGGGGAGATACTAGTGGGTATGGACCCCACTGGGGCCA
AGGTACACTGGTCACCGTGAGCTCA

ROR1-008-A03-VL

CAGTCTGTGCTGACTCAGCCACCCTCAGCGTCTGGGACCCCCGGGCAGAGGGTCACCATCTCCTGTT
CTGGAAGCAGCTCCAACATCGGAAGTAATTATGTATACTGGTATCAGCAGCTCCCAGGAACGGCCCC
CAAACTCCTCATCTATGACAATAATAAGCGACCCTCAGGGGTCCCTGACCGATTCTCTGGCTCCAAG
TCTGGCACCTCAGCCTCCCTGGCCATCAGTGGGCTCCGGTCCGAGGATGAGGCTGATTATTACTGTC
AATCCTACGACGACACCCTGAGTGTTGTGGTGTTCGGCGGAGGAACCAAGCTGACGGTCCTAGGT

*Figure 8*

ROR1-008-D04-VH

EVQLLESGGGLVQPGGSLRLSCAASGFT `FSDYYMS` WIRQAPG `KGLEWV` `AIISYDGSNEYYADSVKGR`
　　　FrH1　　　　　　　　　　CDRH1　　　　　FrH2　　　　　CDRH2

FTISRDNSKNTLYLQMNSLRAEDTAVYYC `ATSSGDGGWEDWGPPYYYYGMDV` WGQGTLVTVSS
　　　FrH3　　　　　　　　　　　　　　CDRH3　　　　　　　　　　FrH4

ROR1-008-D04-VL

QSVLTQPPSASGTPGQRVTIS `CTGSSSNLGAGYAVH` WYQQLPGTAPKLLIY `GNTNRPS` GVPDRFSGS
　　　FrL1　　　　　　　　CDRL1　　　　　　FrL2　　　　　　CDRL2

KSGTSASLAISGLRSEDEADYY `CAAWDDSLRGPV` FGGGTKLTVLG
　　　FrL3　　　　　　　　CDRL3　　　　　FrL4

ROR1-008-D04-VH

GAGGTGCAGCTGTTGGAGTCTGGGGGAGGCTTGGTACAGCCTGGGGGGTCCCTGAGACTCTCCTGTG
CAGCCTCTGGATTCACCTTCAGTGACTACTACATGAGCTGGATCCGCCAGGCTCCAGGGAAGGGGCT
GGAGTGGGTGGCAATTATATCATATGATGGAAGTAATGAATACTATGCAGACTCCGTGAAGGGCCG
ATTCACCATCTCCAGAGACAATTCCAAGAACACGCTGTATCTGCAAATGAACAGCCTGAGAGCCGA
GGACACTGCCGTGTATTACTGTGCAACATCCTCGGGGGATGGGGGATGGGAGGATTGGGGCCCACC
TTACTACTACTACGGTATGGACGTCTGGGGCCAGGGTACACTGGTCACCGTGAGCTCA

ROR1-008-D04-VL

CAGTCTGTGCTGACTCAGCCACCCTCAGCGTCTGGGACCCCCGGGCAGAGGGTCACCATCTCCTGCA
CTGGGAGCAGCTCCAACCTCGGGGCAGGTTATGCTGTACACTGGTATCAGCAGCTCCCAGGAACGG
CCCCCAAACTCCTCATCTATGGTAACACCAATCGGCCCTCAGGGGTCCCTGACCGATTCTCTGGCTCC
AAGTCTGGCACCTCAGCCTCCCTGGCCATCAGTGGGCTCCGGTCCGAGGATGAGGCTGATTATTACT
GTGCGGCATGGGATGACAGCCTGAGAGGTCCGGTGTTCGGCGGAGGAACCAAGCTGACGGTCCTAG
GT

*Figure 9*

ROR1-008-G04-VH

EVQLLESGGGLVQPGGSLRLSCAASGFT FSSYAMS WVRQAPG KGLEWV SVIYSGGSTYYADSVKGR
　　　　　FrH1　　　　　　　　　CDRH1　　　　　　　FrH2　　　　　　CDRH2

FTISRDNSKNTLYLQMNSLRAEDTAVYYC ARDSWELIGYDAFDL WGQGTLVTVSS
　　　　　FrH3　　　　　　　　　　CDRH3　　　　　　　FrH4

ROR1-008-G04-VL

QSVLTQPPSASGTPGQRVTIS CSGSSSNIGSNYVY WYQQLPGTAPKLLIY GDSNRPS GVPDRFSGSK
　　　　　FrL1　　　　　　　CDRL1　　　　　　　FrL2　　　　　CDRL2

SGTSASLAISGLRSEDEADYY CGTWDSSLSAWV FGGGTKLTVLG
　　　FrL3　　　　　　　　CDRL3　　　　　FrL4

ROR1-008-G04-VH

GAGGTGCAGCTGTTGGAGTCTGGGGGAGGCTTGGTACAGCCTGGGGGGTCCCTGAGACTCTCCTGTG
CAGCCTCTGGATTCACCTTTAGCAGCTATGCCATGAGCTGGGTCCGCCAGGCTCCTGGGAAGGGGCT
GGAGTGGGTCTCAGTTATTTATAGCGGTGGTAGCACATACTACGCAGACTCCGTGAAGGGCCGATTC
ACCATCTCCAGAGACAATTCCAAGAACACGCTGTATCTGCAAATGAACAGCCTGAGAGCCGAGGAC
ACTGCCGTGTATTACTGTGCGAGGGATTCTTGGGAGCTAATAGGGTATGATGCTTTTGATCTCTGGG
GCCAAGGTACACTGGTCACCGTGAGCTCA

ROR1-008-G04-VL

CAGTCTGTGCTGACTCAGCCACCCTCAGCGTCTGGGACCCCCGGGCAGAGGGTCACCATCTCTTGTT
CTGGAAGCAGCTCCAACATCGGAAGTAATTATGTATACTGGTATCAGCAGCTCCCAGGAACGGCCCC
CAAACTCCTCATCTATGGTGACAGTAATCGGCCCTCAGGGGTCCCTGACCGATTCTCTGGCTCCAAG
TCTGGCACCTCAGCCTCCCTGGCCATCAGTGGGCTCCGGTCCGAGGATGAGGCTGATTATTACTGCG
GAACATGGGATAGCAGCCTGAGTGCTTGGGTGTTCGGCGGAGGAACCAAGCTGACGGTCCTAGGT

Figure 10

ROR1-008-H06-VH

EVQLLESGGGLVQPGGSLRLSCAASGFT FSNHEMNWVRQAPG KGLEWV SAISGSGGSTYYADSVK
  FrH1                       CDRH1           FrH2   CDRH2

GR FTISRDNSKNTLYLQMNSLRAEDTAVYYC AREEYTILGAYYFDF WGQGTLVTVSS
   FrH3                          CDRH3           FrH4

ROR1-008-H06-VL

QSVLTQPPSASGTPGQRVTIS CSGSSSNIESSTVN WYQQLPGTAPKLLIY DNNKRPS GVPDRFSGSK
  FrL1                CDRL1          FrL2            CDRL2

SGTSASLAISGLRSEDEADYY CQSYDSSLSPLVL FGGGTKLTVLG
  FrL3                CDRL3         FrL4

ROR1-008-H06-VH

GAGGTGCAGCTGTTGGAGTCTGGGGGAGGCTTGGTACAGCCTGGGGGGTCCCTGAGACTCTCCTGTG
CAGCCTCTGGATTCACCTTCAGTAATCATGAAATGAATTGGGTCCGCCAGGCTCCAGGGAAGGGGCT
GGAGTGGGTCTCAGCTATTAGTGGTAGTGGTAGCACATACTACGCAGACTCCGTGAAGGGCCG
GTTCACCATCTCCAGAGACAATTCCAAGAACACGCTGTATCTGCAAATGAACAGCCTGAGAGCCGA
GGACACTGCCGTGTATTACTGTGCGAGAGAAGAATATACGATTTTGGGAGCCTACTACTTTGACTTC
TGGGGCCAGGGTACACTGGTCACCGTGAGCTCA

ROR1-008-H06-VL

CAGTCTGTGCTGACTCAGCCACCCTCAGCGTCTGGGACCCCCGGGCAGAGGGTCACCATCTCTTGTT
CTGGAAGCAGCTCCAACATCGAAAGTAGTACTGTAAACTGGTATCAGCAGCTCCCAGGAACGGCCC
CCAAACTCCTCATCTATGACAATAATAAGCGACCCTCAGGGGTCCCTGACCGATTCTCTGGCTCCAA
GTCTGGCACCTCAGCCTCCCTGGCCATCAGTGGGCTCCGGTCCGAGGATGAGGCTGATTATTACTGC
CAGTCATATGACAGTAGCCTGAGTCCTCTTGTGCTGTTCGGCGGAGGAACCAAGCTGACGGTCCTAG
GT

Figure 11

ROR1-009-G03-VH

EVQLLESGGGLVQPGGSLRLSCAASGFT FSDYYMSWIRQAPG KGLEWV SAISGSGGSTYYADSVKG
　　　　　FrH1　　　　　　　　　CDRH1　　　　　FrH2　　　　CDRH2

R FTISRDNSKNTLYLQMNSLRAEDTAVYYC AKEDWEGASFDY WGQGTLVTVSS
　　　　FrH3　　　　　　　　　　　CDRH3　　　　　FrH4

ROR1-009-G03-VL

QSVLTQPPSASGTPGQRVTIS CSGSSSNIGINTVN WYQQLPGTAPKLLIY DNNKRPS GVPDRFSGSKS
　　　FrL1　　　　　　　CDRL1　　　　　FrL2　　　　CDRL2

GTSASLAISGLRSEDEADYY CATWDDSLSGWV FGGGTKLTVLG
　　FrL3　　　　　　　CDRL3　　　　　FrL4

ROR1-009-G03-VH

GAGGTGCAGCTGTTGGAGTCTGGGGGAGGCTTGGTACAGCCTGGGGGGTCCCTGAGACTCTCCTGTG
CAGCCTCTGGATTCACCTTCAGTGACTACTACATGAGCTGGATCCGCCAGGCTCCAGGGAAGGGGCT
GGAGTGGGTCTCAGCTATTAGTGGTAGTGGTGGTAGCACATACTACGCAGACTCCGTGAAGGGCCG
GTTCACCATCTCCAGAGACAATTCCAAGAACACGCTGTATCTGCAAATGAACAGCCTGAGAGCCGA
GGACACTGCCGTGTATTACTGTGCGAAAGAAGATTGGGAGGGAGCCTCGTTTGACTACTGGGGCCA
GGGTACACTGGTCACCGTGAGCTCA

ROR1-009-G03-VL

CAGTCTGTGCTGACTCAGCCACCCTCAGCGTCTGGGACCCCCGGGCAGAGGGTCACCATCTCTTGTT
CTGGAAGCAGCTCCAACATCGGAATTAATACTGTAAACTGGTATCAGCAGCTCCCAGGAACGGCCC
CCAAACTCCTCATCTATGACAATAATAAGCGACCCTCAGGGGTCCCTGACCGATTCTCTGGCTCCAA
GTCTGGCACCTCAGCCTCCCTGGCCATCAGTGGGCTCCGGTCCGAGGATGAGGCTGATTATTACTGT
GCAACATGGGATGACAGCCTGAGTGGTTGGGTGTTCGGCGGAGGAACCAAGCTGACGGTCCTAGGT

*Figure 12*

ROR1-009-G11-VH

EVQLLESGGGLVQPGGSLRLSCAASGFT FSSYSMNWVRQAPG KGLEWV SSISSSSSYIYYADSVKG
　　　　　　FrH1　　　　　　　　CDRH1　　　　　FrH2　　　　CDRH2

R FTISRDNSKNTLYLQMNSLRAEDTAVYYC ARRGTTFDY WGQGTLVTVSS
　　　　　FrH3　　　　　　　　　　　CDRH3　　　　FrH4

ROR1-009-G11-VL

QSVLTQPPSASGTPGQRVTISC TGSNSNLGAPYDVH WYQQLPGTAPKLLIY SDNQRPS GVPDRFSGS
　　　　　FrL1　　　　　　CDRL1　　　　　　FrL2　　　　CDRL2

KSGTSASLAISGLRSEDEADYYC CGTWDDSLSGWV FGGGTKLTVLG
　　　FrL3　　　　　　　CDRL3　　　　　FrL4

ROR1-009-G11-VH

GAGGTGCAGCTGTTGGAGTCTGGGGGAGGCTTGGTACAGCCTGGGGGGTCCCTGAGACTCTCCTGTG
CAGCCTCTGGATTCACCTTCAGTAGCTATAGCATGAACTGGGTCCGCCAGGCTCCAGGGAAGGGGCT
GGAGTGGGTCTCATCCATTAGTAGTAGTAGTAGTTACATATACTACGCAGACTCAGTGAAGGGCCGA
TTCACCATCTCCAGAGACAATTCCAAGAACACGCTGTATCTGCAAATGAACAGCCTGAGAGCCGAG
GACACTGCCGTGTATTACTGTGCGAGAAGGGGGACGACTTTTGACTACTGGGGCCAGGGTACACTG
GTCACCGTGAGCTCA

ROR1-009-G11-VL

CAGTCTGTGCTGACTCAGCCACCCTCGGCGTCTGGGACCCCCGGGCAGAGGGTCACCATCTCCTGCA
CTGGGAGCAACTCCAACCTCGGGGCACCTTATGATGTACACTGGTATCAGCAGCTCCCAGGAACGGC
CCCCAAACTCCTCATCTATAGTGATAATCAGCGGCCCTCAGGGGTCCCTGACCGATTCTCTGGCTCC
AAGTCTGGCACCTCAGCCTCCCTGGCCATCAGTGGGCTCCGGTCCGAGGATGAGGCTGATTATTACT
GTGGAACATGGGATGACAGCCTGAGTGGTTGGGTGTTCGGCGGAGGAACCAAGCTGACGGTCCTAG
GT

*Figure 13*

ROR1-010-D05-VH

EVQLLESGGGLVQPGGSLRLSCAASGFT FSSYAMN WVRQAPG KGLEWV SGVSWNGSRTHYADSVK
　　　　FrH1　　　　　　　　　CDRH1　　　　FrH2　　　　CDRH2

GR FTISRDNSKNTLYLQMNSLRAEDTAVYYC ASNAPFDP WGQGTLVTVSS
　　　　FrH3　　　　　　　　　　CDRH3　　　　FrH4

ROR1-010-D05-VL

QSVLTQPPSASGTPGQRVTIS CSGSSSNIGSNYVY WYQQLPGTAPKLLIY DNNKRPS GVPDRFSGSK
　　　　FrL1　　　　　　　CDRL1　　　　　FrL2　　　　CDRL2

SGTSASLAISGLRSEDEADYY CQSYDSSLSAVV FGGGTKLTVLG
　　　　FrL3　　　　　　CDRL3　　　　FrL4

ROR1-010-D05-VH

GAGGTGCAGCTGTTGGAGTCTGGGGGAGGCTTGGTACAGCCTGGGGGGTCCCTGAGACTCTCCTGTG
CAGCCTCTGGATTCACCTTTAGCAGCTATGCCATGAACTGGGTCCGCCAGGCTCCAGGGAAGGGGCT
GGAGTGGGTATCGGGTGTTAGTTGGAATGGCAGTAGGACGCACTATGCAGACTCTGTGAAGGGCCG
ATTCACCATCTCCAGAGACAATTCCAAGAACACGCTGTATCTGCAAATGAACAGCCTGAGAGCCGA
GGACACTGCCGTGTATTACTGTGCGAGTAACGCACCCTTCGACCCCTGGGGCCAAGGTACACTGGTC
ACCGTGAGCTCA

ROR1-010-D05-VL

CAGTCTGTGCTGACTCAGCCACCCTCAGCGTCTGGGACCCCCGGGCAGAGGGTCACCATCTCTTGTT
CTGGAAGCAGCTCCAACATCGGAAGTAATTATGTATACTGGTATCAGCAGCTCCCAGGAACGGCCCC
CAAACTCCTCATCTATGACAATAATAAGCGACCCTCAGGGGTCCCTGACCGATTCTCTGGCTCCAAG
TCTGGCACCTCAGCCTCCCTGGCCATCAGTGGGCTCCGGTCCGAGGATGAGGCTGATTATTACTGCC
AGTCCTATGACAGCAGCCTGAGTGCTGTGGTATTCGGCGGAGGAACCAAGCTGACGGTCCTAGGT

*Figure 14*

ROR1-010-D06-VH

EVQLLESGGGLVQPGGSLRLSCAASGFT FRDYGMHWVRQAPG KGLEWV SAISGSGGSTFYADSVK
   FrH1                      CDRH1            FrH2        CDRH2

GR FTISRDNSKNTLYLQMNSLRAEDTAVYYC ARGRSAGSMGYFDY WGQGTLVTVSS
   FrH3                           CDRH3           FrH4

ROR1-010-D06-VL

QSVLTQPPSASGTPGQRVTIS CTGSSSNIGAGYDVH WYQQLPGTAPKLLIY GNSNRPS GVPDRFSGS
   FrL1                CDRL1              FrL2           CDRL2

KSGTSASLAISGLRSEDEADYY CAAWDDSLNGWV FGGGTKLTVLG
   FrL3                  CDRL3         FrL4

ROR1-010-D06-VH

GAGGTGCAGCTGTTGGAGTCTGGGGGAGGCTTGGTACAGCCTGGGGGGTCCCTGAGACTCTCCTGTG
CAGCCTCTGGATTCACCTTCAGAGACTATGGCATGCACTGGGTCCGCCAGGCTCCAGGCAAGGGGCT
GGAGTGGGTCTCAGCTATTAGTGGTAGTGGTGGTAGCACATTCTACGCAGACTCCGTGAAGGGCCGG
TTCACCATCTCCAGAGACAATTCCAAGAACACGCTGTATCTGCAAATGAACAGCCTGAGAGCCGAG
GACACTGCCGTGTATTACTGTGCGAGAGGCCGGTCGGCTGGTAGCATGGGCTACTTTGACTACTGGG
GCCAAGGTACACTGGTCACCGTGAGCTCA

ROR1-010-D06-VL

CAGTCTGTGCTGACTCAGCCACCCTCAGCGTCTGGGACCCCCGGGCAGAGGGTCACCATCTCCTGCA
CTGGGAGCAGCTCCAACATCGGGGCAGGTTATGATGTACACTGGTATCAGCAGCTCCCAGGAACGG
CCCCCAAACTCCTCATCTATGGTAACAGCAATCGGCCCTCAGGGGTCCCTGACCGATTCTCTGGCTC
CAAGTCTGGCACCTCAGCCTCCCTGGCCATCAGTGGGCTCCGGTCCGAGGATGAGGCTGATTATTAC
TGTGCAGCATGGGATGACAGTCTGAATGGTTGGGTGTTCGGCGGAGGAACCAAGCTGACGGTCCTA
GGT

*Figure 15*

ROR1-011-F01-VH

EVQLLESGGGLVQPGGSLRLSCAASGFT FSDYYMSWVRQAPG KGLEWV AIISYDGNENYYADSVKG
　　　　FrH1　　　　　　　　　　　CDRH1　　　　　FrH2　　　　CDRH2

R FTISRDNSKNTLYLQMNSLRAEDTAVYYC AREDIDYADDAYDI WGQGTLVTVSS
　　　　FrH3　　　　　　　　　　　CDRH3　　　　　FrH4

ROR1-011-F01-VL

QSVLTQPPSASGTPGQRVTIS CTGSSSNIGAGYDVL WYQQLSGTAPKLLIY SNNQRPS GVPDRFSGS
　　　　FrL1　　　　　　　CDRL1　　　　　　　　FrL2　　　　　　CDRL2

KSGTSASLAISGLRSEDEADYY CASWDDSLSGPV FGGGTKLTVLG
　　FrL3　　　　　　　　　CDRL3　　　　FrL4

ROR1-011-F01-VH

GAGGTGCAGCTGTTGGAGTCTGGGGGAGGCTTGGTACAGCCTGGGGGGTCCCTGAGACTCTCCTGTG
CAGCCTCTGGATTCACCTTCAGTAGCAACTACATGAGCTGGGTCCGCCAGGCTCCAGGGAAGGGGCT
GGAGTGGGTCTCAACTGTTAGTGCTGGTGGTGGTAGCACATTCTACGCAGACTCCGTGAAGGGCCGG
TTCACCATCTCCAGAGACAATTCCAAGAACACGCTGTATCTGCAAATGAACAGCCTGAGAGCCGAG
GACACTGCCGTGTATTACTGTGCGAGAGGCCAAGATGGGGCCAATGACTACTGGGGCCAAGGTACA
CTGGTCACCGTGAGCTCA

ROR1-011-F01-VL

CAGTCTGTGCTGACTCAGCCACCCTCAGCGTCTGGGACCCCCGGGCAGAGGGTCACCATCTCCTGCA
CTGGGAGCAGCTCCAACATCGGGGCAGGTTATGATGTACTCTGGTATCAGCAGCTCTCAGGAACGGC
CCCCAAACTCCTCATCTATAGTAATAATCAGCGGCCCTCAGGGGTCCCTGACCGATTCTCTGGCTCC
AAGTCTGGCACCTCAGCCTCCCTGGCCATCAGTGGGCTCCGGTCCGAGGATGAGGCTGATTATTACT
GTGCATCATGGGATGACAGCCTGAGTGGTCCGGTGTTCGGCGGAGGAACCAAGCTGACGGTCCTAG
GT

*Figure 16*

Figure 17A
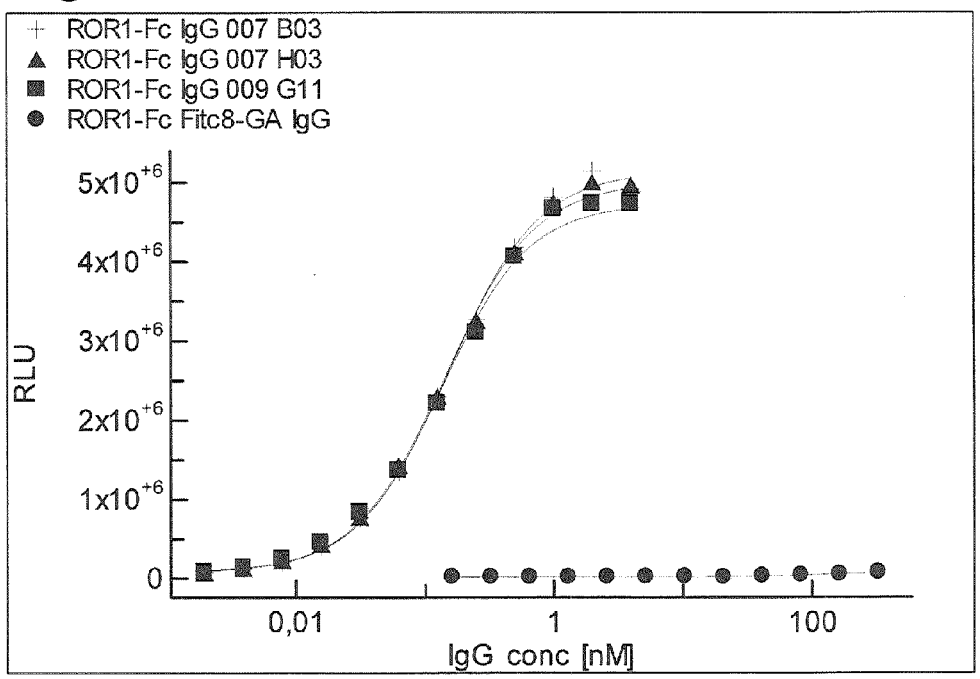
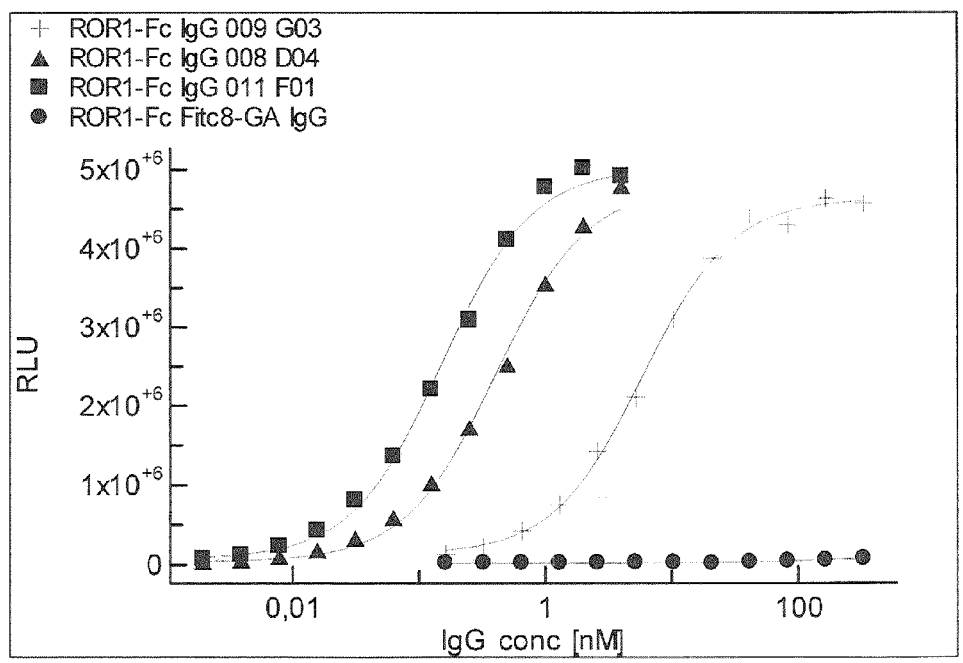
Figure 17B

Figure 17C
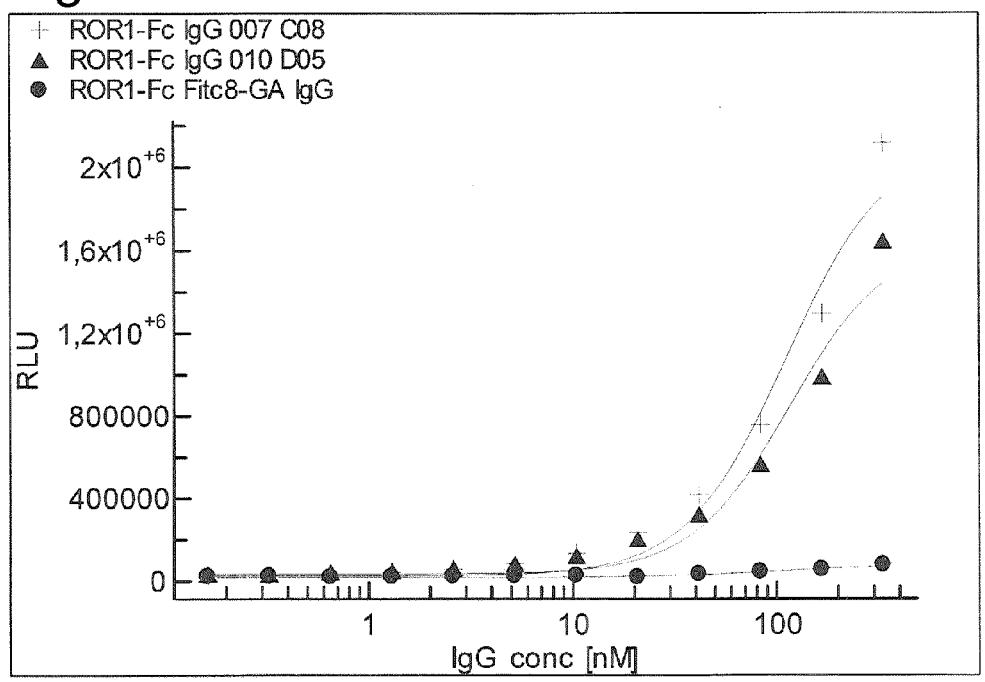
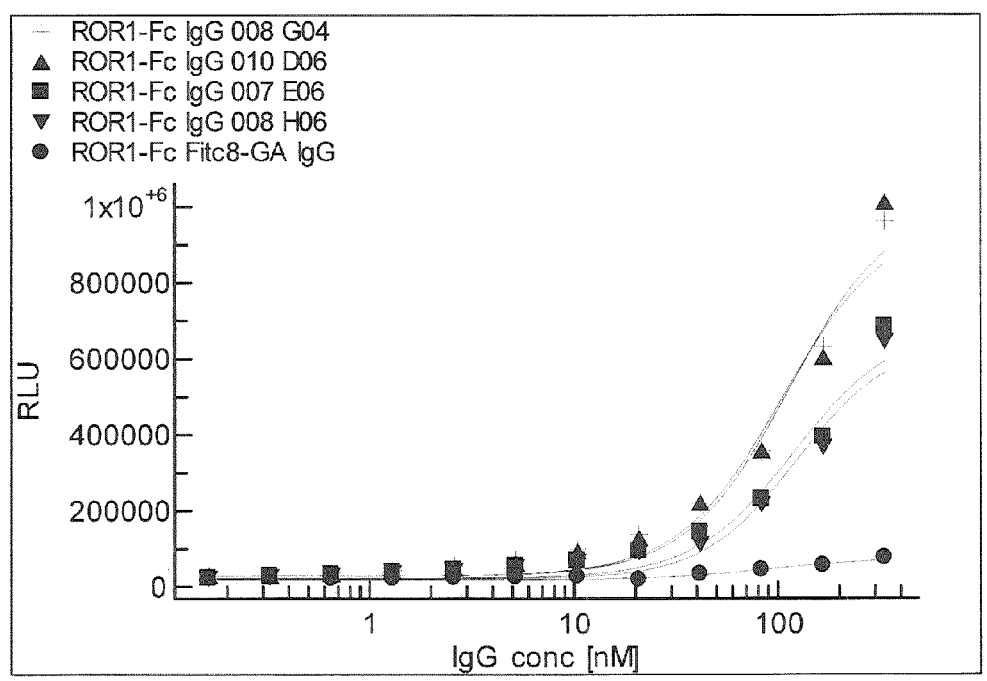
Figure 17D

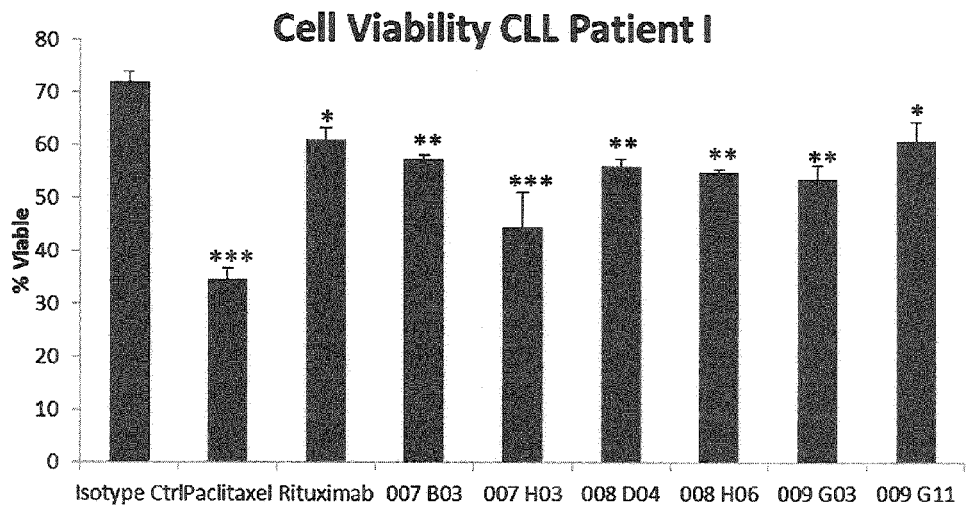
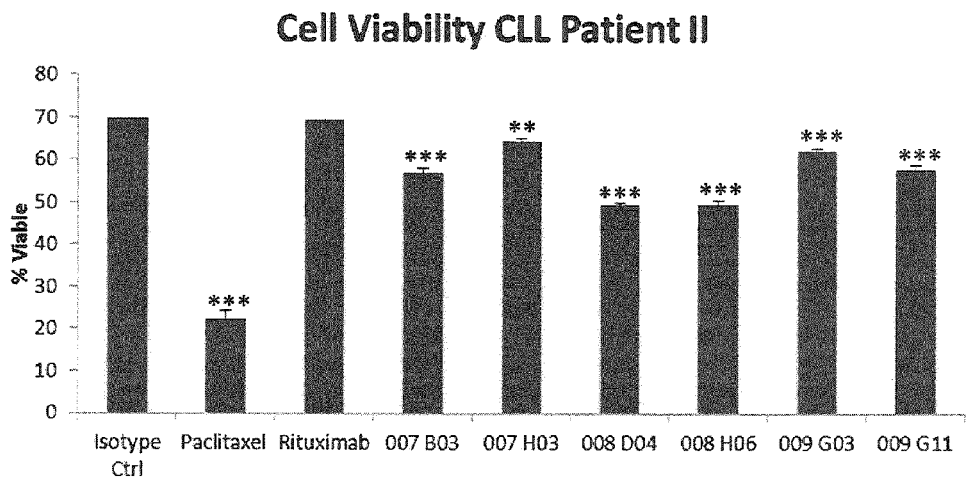
Figure 20

Figure 27A
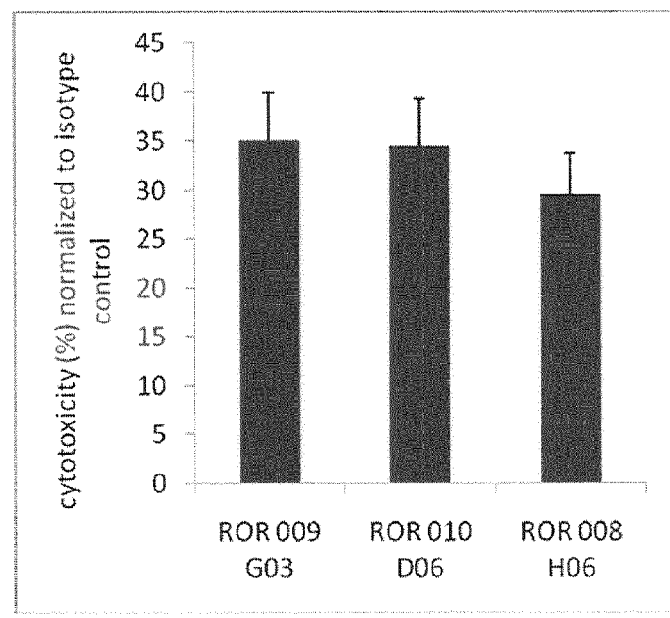
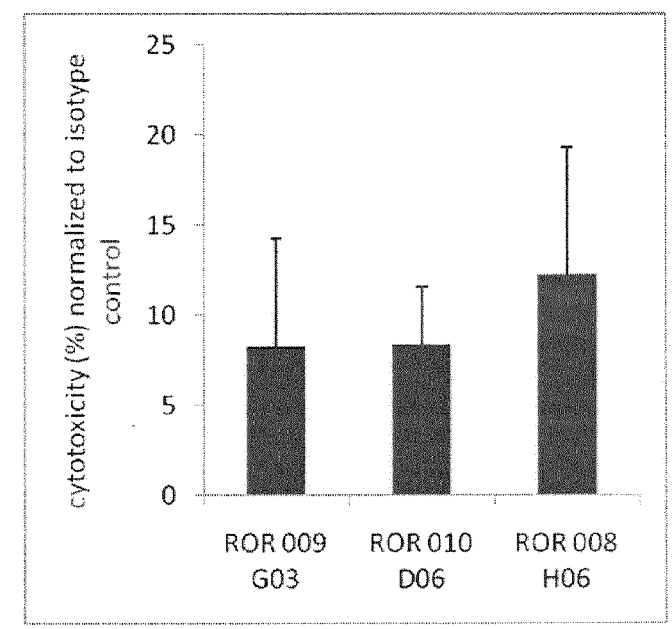
Figure 27B

Figure 29A
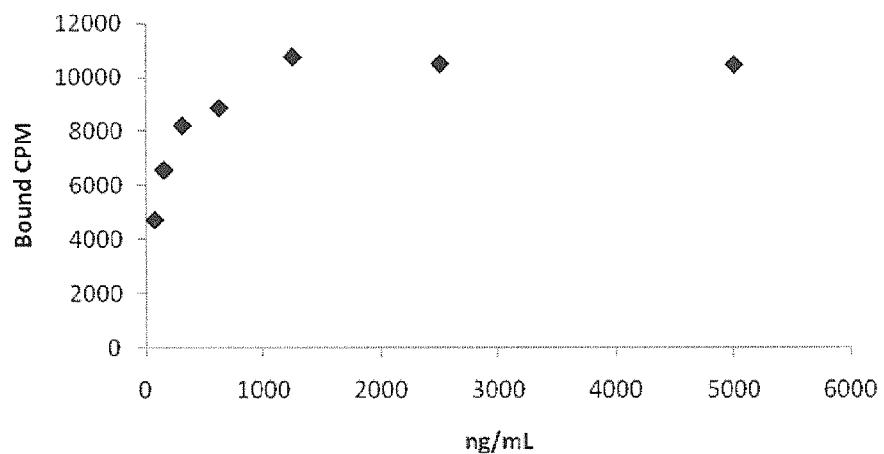
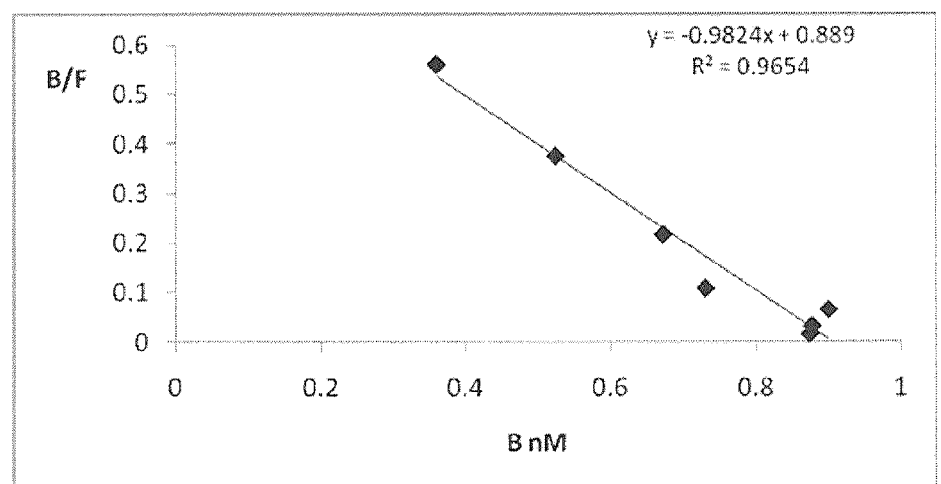
Figure 29B

ANTIBODIES AGAINST ROR1 AND USES THEREOF

FIELD OF THE INVENTION

The present invention relates to antibodies that inhibit ROR1 and are capable of inducing cell death by the specific binding of ROR1, domains thereof or nucleotide molecules encoding ROR1.

REFERENCE TO SEQUENCE LISTING

A Sequence Listing submitted as an ASCII text file via EFS-Web is hereby incorporated by reference in accordance with 35 U.S.C. §1.52(e). The name of the ASCII text file for the Sequence Listing is 15566933.TXT, the date of creation of the ASCII text file is Jun. 10, 2013, and the size of the ASCII text file is 59.1 KB.

BACKGROUND OF THE INVENTION

The work leading to this invention has received funding from the European Community's Seventh Framework Programme FP7/2007-2013/under grant agreement No HEALTH-F5-2008-200755.

Chronic lymphocytic leukaemia (CLL) is a white blood cell cancer that is characterised by an abnormal neoplastic proliferation of B lymphocyte cells (B cells). The B cells of CLL differ from normal B cells in their activation and maturation stage and are in particular derived from antigen experienced B cells with different immunoglobulin heavy chain variable (IgVH) gene mutations (Chiorazzi N et al., N Engl J Med 2005; 352:804-15). CLL patients with mutated IgVH genes have a better prognosis compared to patients with unmutated genes (Damle R N et al., Blood 1999; 94:1840-7; Hamblin T J et al., Blood 1999; 94:1848-54).

Global gene expression profiling studies have revealed partly distinguishing but in general overlapping expression profiles in mutated and unmutated leukaemic B cells, suggesting a common phenotype (Klein U et al., J Exp Med 2001; 194:1625-38; Rosenwald A et al., J Exp Med 2001; 194:1639-47).

Gene expression profiling studies have shown a 43.8 fold increase of the orphan receptor tyrosine kinase (RTK) ROR1 in CLL cells (Klein U et al., J Exp Med 2001; 194:1625-38). Ror1 is a member of the RTK family of orphan receptors related to muscle specific kinase (MUSK) and Trk neurotrophin receptors (Glass D J, et al., Cell 1996; 85:513-23; Masiakowski P et al., J Biol Chem 1992; 267:26181-90; Valenzuela D M et al., Neuron 1995; 15:573-84).

Ror receptors are cell surface receptors participating in signal transduction, cell-cell interaction, regulation of cell proliferation, differentiation, cell metabolism and survival (Masiakowski P et al., Biol Chem 1992; 267:26181-90; Yoda A et al., J Recept Signal Transduct Res 2003; 23:1-15). They are evolutionarily highly conserved between different species e.g. human, mouse, *Drosophila*, and *C. elegans*.

The human ROR1 gene has a coding region of 2814 bp with a predicted 937 amino acids sequence and 105 kDa protein size including an Ig-like domain, cysteine-rich domain, kringle domain, tyrosine kinase domain, and proline-rich domain (FIG. 1) (Yoda A et al., J Recept Signal Transduct Res 2003; 23:1-15).

ROR1 is located on chromosomal region 1p31.3 (http://www.ensembl.org), a region where chromosomal aberrations are not frequently seen in haematological malignancies (FIG. 2). The human ROR1 is expressed in heart, lung, and kidney but less in placenta, pancreas and skeletal muscles (Reddy U R et al., Oncogene 1996; 13:1555-9). ROR1 was originally cloned from a neuroblastoma cell line (Masiakowski P et al., J Biol Chem 1992; 267:26181-90) and subsequently a shorter form lacking the entire extracellular domain but containing the transmembrane domain was isolated from a foetal brain library. Truncated Ror1 (t-Ror1) gene has been reported in foetal and adult human central nervous system, in human leukaemias, lymphoma cell lines, and in a variety of human cancers derived from neuroectoderm (Reddy U R et al., Oncogene 1996; 13:1555-9). A shorter transcript from exons 1-7 including a short part of intron 7 has also been described with a predicted length of 393 amino acids and a molecular weight of 44 kDa (Ensembl ID; ENSG00000185483).

The expression of ROR-1 in cancer cells has been described for CLL (Baskar et al (2008) Clin Cancer Res, 14, p 396-404; Choudhury et al (2010) B. J. Haem, 151, p327-335; and Hudecek et al (2010) Blood, online publication DOI: 10.1182/blood-2010-05-283309); MCL (Hudecek (2010)); B-ALL (Hudecek (2010) and Shabani at al (2008) Leuk & Lymph, 49 p1360-1367), other leukaemias and lymphomas (Fakuda et al (2008) PNAS, 105, p3047-3052; and Barna et al (2010) Hematol Oncol, online publication DOI: 10-1002/hon.948) and solid cancers (renal and colon) (Katoh & Kotoh (2005) Oncol Rep 14, p1381-4).

SUMMARY OF THE INVENTION

In a first aspect of the invention there is provided anti-ROR1 antibody capable of inducing cell death in a cell expressing ROR1. The anti-ROR antibodies may induce cell death directly or via different effector mechanisms, such as, antibody dependent cell cytotoxicity (ADCC), complement dependent cytotoxicity (CDC) or antibody dependent cellular phagocytosis (ADCP).

The antibody may act to reduce the amount of or action of ROR1. For example, the antibody may act directly by binding to ROR1 or a nucleotide sequence encoding ROR1. The antibody may alternatively act by preventing ROR1 interacting with molecules that it normally interacts with e.g. by blocking receptors, sequestering molecules that bind to or associate with ROR1, preventing insertion of ROR1 or its binders from inserting into a membrane, such as the cell membrane.

Preferably, the antibody binds specifically to either an extracellular domain of ROR1, an intracellular domain of ROR1 or to a nucleotide sequence encoding ROR1.

By antibody we mean complete antibodies and antigen binding fragments thereof. Such fragments are defined below.

Antibodies comprise two identical polypeptides of $M_r$ 50,000-70,000 (termed "heavy chains") that are linked together by a disulphide bond, each of which is linked to one of an identical pair of polypeptides of $M_r$ 25,000 (termed "light chains"). There is considerable sequence variability between individual N-termini of heavy chains of different antibody molecules and between individual light chains of different antibody molecules and these regions have hence been termed "variable domains". Conversely, there is considerable sequence similarity between individual C-termini of heavy chains of different antibody molecules and between individual light chains of different antibody molecules and these regions have hence been termed "constant domains".

In general, an antibody molecule obtained from humans relates to any of the classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain.

Reference herein to antibodies includes a reference to all such classes, subclasses and types of human antibody species.

The antigen-binding site is formed from hyper-variable regions in the variable domains of a pair of heavy and light chains. The hyper-variable regions are also known as complementarity-determining regions (CDRs) and determine the specificity of the antibody for a ligand. The variable domains of the heavy chain ($V_H$) and light chain ($V_L$) typically comprise three CDRs, each of which is flanked by sequence with less variation, which are known as framework regions (FRs).

The variable heavy ($V_H$) and variable light ($V_L$) domains of the antibody are involved in antigen recognition, a fact first recognised by early protease digestion experiments. Further confirmation was found by "humanisation" of rodent antibodies. Variable domains of rodent origin may be fused to constant domains of human origin such that the resultant antibody retains the antigenic specificity of the rodent parented antibody (Morrison et al., 1984, *Proc. Natl. Acad. Sci. USA*, 81, 6851-6855).

That antigenic specificity is conferred by variable domains and is independent of the constant domains is known from experiments involving the bacterial expression of antibody fragments, all containing one or more variable domains. These molecules include Fab-like molecules (Better et al., 1988, *Science*, 240:1041). Fv molecules (Skerra et al., 1988, *Science*, 240, 1038); single-chain Fv (ScFv) molecules where the $V_H$ and $V_L$ partner domains are linked via a flexible oligopeptide (Bird et al., 1988, *Science* 242:423; Huston et al., 1988, *Proc. Natl. Acad. Sci. USA*, 85:5879) and single domain antibodies (dAbs) comprising isolated V domains (Ward et al., 1989 *Nature* 341, 544). A general review of the techniques involved in the synthesis of antibody fragments which retain their specific binding sites is to be found in Winter et al., 1991, *Nature*, 349, 293-299.

For the production of polyclonal antibodies, various suitable host animals (e.g., rabbit, goat, mouse or other mammal) may be immunized by one or more injections with the native protein, a synthetic variant thereof, or a derivative of the foregoing. An appropriate immunogenic preparation can contain, for example, the naturally occurring immunogenic protein, a chemically synthesized polypeptide representing the immunogenic protein, or a recombinantly expressed immunogenic protein. Furthermore, the protein may be conjugated to a second protein known to be immunogenic in the mammal being immunized. Examples of such immunogenic proteins include but are not limited to keyhole limpet hemocyanin, serum albumin, bovine thyroglobulin, and soybean trypsin inhibitor. The preparation can further include an adjuvant. Various adjuvants used to increase the immunological response include, but are not limited to, Freund's (complete and incomplete), mineral gels (e.g., aluminum hydroxide), surface-active substances (e.g., lysolecithin, pluronic polyols, polyanions, peptides, oil emulsions, dinitrophenol, etc.), adjuvants usable in humans such as Bacille Calmette-Guerin and *Corynebacterium parvum*, or similar immunostimulatory agents. Additional examples of adjuvants that can be employed include MPL-TDM adjuvant (monophosphoryl Lipid A, synthetic trehalose dicorynomycolate).

The polyclonal antibody molecules directed against the immunogenic protein can be isolated from the mammal (e.g., from the blood) and further purified by well known techniques, such as affinity chromatography using protein A or protein G, which provide primarily the IgG fraction of immune serum. Subsequently, or alternatively, the specific antigen which is the target of the immunoglobulin sought, or an epitope thereof, may be immobilized on a column to purify the immune specific antibody by immunoaffinity chromatography. Purification of immunoglobulins is discussed, for example, by D. Wilkinson (The Scientist, published by The Scientist, Inc., Philadelphia Pa., Vol. 14, No. 8 (Apr. 17, 2000), pp. 25-28).

The term "monoclonal antibody" (mAb) or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs thus contain an antigen-binding site capable of immunoreacting with a particular epitope of the antigen characterized by a unique binding affinity for it.

The antibody may be a human or humanised antibody or fragment thereof. The antibody may be a fragment including scFv molecules or Fab molecules.

By "ScFv molecules" we mean molecules wherein the $V_H$ and $V_L$ partner domains are linked via a flexible oligopeptide.

The advantages of using antibody fragments which have antigen-binding activity, rather than whole antibodies, are several-fold. The smaller size of the fragments may lead to improved pharmacological properties, such as better penetration of solid tissue. Effector functions of whole antibodies, such as complement binding, are removed. Fab, Fv, ScFv and dAb antibody fragments can all be expressed in and secreted from *Escherichia coli* (*E. coli*), thus allowing the facile production of large amounts of the said fragments.

Whole antibodies, and F(ab')$_2$ fragments are "bivalent". By "bivalent" we mean that the said antibodies and F(ab')$_2$ fragments have two antigen combining sites. In contrast, Fab, Fv, ScFv and dAb fragments are monovalent, having only one antigen combining site.

Methods for generating, isolating and using antibodies for a desired antigen or epitope are well known to those skilled in the relevant art. For example, an antibody may be raised in a suitable host animal (such as, for example, a mouse, rabbit or goat) using standard methods known in the art and either used as crude antisera or purified, for example by affinity purification. An antibody of desired specificity may alternatively be generated using well-known molecular biology methods, including selection from a molecular library of recombinant antibodies, or grafting or shuffling of complementarity-determining regions (CDRs) onto appropriate framework regions. Human antibodies may be selected from recombinant libraries and/or generated by grafting CDRs from non-human antibodies onto human framework regions using well-known molecular biology techniques.

The antibodies may be modified in a number of ways in order to enhance their properties either by improving binding affinity or specificity, or to carry effector molecules or detectable moieties. The antibodies may also be humanized wherein such antibodies are suitable for administration to humans without engendering an immune response by the human against the administered immunoglobulin. Humanized forms of antibodies are chimeric immunoglobulins, immunoglobulin chains or fragments thereof (such as Fv, Fab, Fab', F(ab')$_2$ or other antigen-binding subsequences of antibodies) that are principally comprised of the sequence of a human immunoglobulin, and contain minimal sequence derived from a non-human immunoglobulin. Humanization can be performed following the method of Winter and co-workers (Jones et al., *Nature*, 321:522-525 (1986); Riechmann et al., *Nature*, 332:323-327 (1988); Verhoeyen et al., *Science*, 239:1534-1536 (1988)), by substituting CDRs from another source into a human antibody.

Antibodies of one embodiment of the invention may possess the VH and VL amino acid sequences shown in FIGS. 4 to 16. In particular, the antibodies may comprise the VH and VL sequence combinations of one of:

ROR1-007-B03-VH
ROR1-007-B03-VL
(FIG. 4)
ROR1-007-008-VH
ROR1-007-008-VL
(FIG. 5)
ROR1-007-E06-VH
ROR1-007-E06-VL
(FIG. 6)
ROR1-007-H03-VH
ROR1-007-H03-VL
(FIG. 7)
ROR1-008-A03-VH
ROR1-008-A03-VL
(FIG. 8)
ROR1-008-D04-VH
ROR1-008-D04-VL
(FIG. 9)
ROR1-008-G04-VH
ROR1-008-G04-VL
(FIG. 10)
ROR1-008-H06-VH
ROR1-008-H06-VL
(FIG. 11)
ROR1-009-G03-VH
ROR1-009-G03-VL
(FIG. 12)
ROR1-009-G11-VH
ROR1-009-G11-VL
(FIG. 13)
ROR1-010-D05-VH
ROR1-010-D05-VL
(FIG. 14)
ROR1-010-D06-VH
ROR1-010-D06-VL
(FIG. 15)
ROR1-011-F01-VH
ROR1-011-F01-VL
(FIG. 16)

The antibodies of the invention may also comprise the combination of a VH and VL chain each from a different pairs described in FIGS. 4 to 16, by way of example (but not limiting to) VH from FIG. 4 and VL from FIG. 5.

The antibodies of the invention can alternatively be described as comprising at least one CDR selected from the CDRs shown in the VH and VL chains of FIGS. 4 to 16, i.e. at least one of CDRH1, CDRH2, CDRH3, CDRL1, CDRL2, or CDRL3.

Preferably, there is 1, 2, 3, 4, 5, or 6 of the CDRs shown (highlighted) in FIGS. 4 to 16. Where there is more than one CDR present, it is preferred that the CDRs are different and are selected separately from CDRH1, CDRH2, CDRH3, CDRL1, CDRL2, or CDRL3.

Antibodies of the invention also include those that compete against the antibodies having the sequences of FIGS. 4 to 16, for binding of the same epitope of ROR1. Competing antibodies can be detected by any standard method including FACS or ELISA based methods of detecting competitive binding (see examples).

By epitope we mean the specific region of ROR1 to which the antibody binds.

By specific binding or specifically binding or specific for we mean that the variable regions of the antibodies of the invention recognize and bind polypeptides of the invention exclusively (i.e., able to distinguish the polypeptide of the invention from other similar polypeptides despite sequence identity, homology, or similarity found in the family of polypeptides)

The antibodies may also comprise the constant regions (CH and CL) shown in FIG. 3.

By extracellular domain we mean the part of a biological molecule that extends beyond the membrane surface of the cell, where said biological molecule is integrated in/embedded in the cell membrane. An example of such a biological molecule is a receptor which possess an extracellular portion to which ligands bind. If the polypeptide chain of the receptor crosses the bilayer several times, the external domain can comprise several "loops" sticking out of the membrane. Any one or combination of which may form a binding site for a ligand.

In one embodiment the extracellular domain to which the antibody binds has the amino acid sequence WNISSELNKDSYLTL (SEQ ID NO: 1).

Alternatively the intracellular domain to which the antibody binds has the amino acid sequence NKSQKPYKIDSKQAS (SEQ ID NO: 2).

Identification of target domains and the production of biological inhibitors to such domains is described in more detail in DaneshManesh (2008) Int J. Cancer 123 p1190-1195.

Conveniently the antibody induces cell death in a cell expressing ROR1 upon specific binding of the antibody to an ROR1 molecule or domain thereof.

Preferably the antibody causes death of a cell expressing ROR1. By cell death we include all forms of cell death, including, but not limited to, apoptosis, necrosis, pyroptosis and autophagic cell death. Furthermore, cell death may occur via FcγR dependent mechanisms or through activation of the complement cascade.

Apoptosis (programmed cell death, type I), is the process by which cells deliberately destroy themselves by systematically dismantling their contents which are then taken up by surrounding cells.

Autophagic cell death (also know as cytoplasmic or programmed cell death, type II) is characterised by characterized by the formation of large vacuoles which eat away organelles in a specific sequence prior to the nucleus being destroyed.

Pyroptosis is a cell death pathway resulting from caspase-1 activity leading to membrane breakdown and proinflammatory cytokine processing and release.

Necrosis is premature cell death that occurs without the controlled systematic dismantling of the cell and its constituent parts. Typically necrosis is characterised by rupturing of organelles and leakage of enzymatic compounds such as lysozymes which then damage and cause necrosis of neighbouring cells.

FcγR mediated mechanisms include antibody dependent cell cytotoxicity (ADCC), resulting in lysis of target cells, and antibody dependent cellular phagocytosis (ADCP) resulting in the uptake and subsequent killing of the target cells by phagocytes.

Activation of the complement cascade results in disruption of cell membrane integrity and subsequent cell lysis, this is commonly known as complement dependent cytotoxicity (CDC).

Antibodies may be used in therapy—for example, a medicament comprising therapeutic antibodies may be introduced into a subject to modulate the immune response of that subject. For example, a therapeutic antibody specific for an antigen in the subject will stimulate an immune response to that antigen, thereby inducing and/or promoting an immune response and aiding recovery. Methods for administering therapeutic antibodies to a patient in need thereof are well known in the art.

It is preferred that the antibodies of the invention exhibit a minimum of internalisation into cells. The antibodies should bind to targets on the exterior of the cell and the receptor should not be internalised in response to this binding. The antibodies of the invention primarily exhibit their effects by not being internalised.

It will be understood by a skilled person that during the lifetime of a cell that a surface molecule may be internalised (as part of growth and natural cell membrane turnover and replenishment) and as such may therefore also internalise any bound antibodies. However, this coincidental internalisation of antibodies is of little relevance to the invention as it occurs at a slow rate and does not occur directly or indirectly in response to binding.

Hence, in order to differentiate between intentional internalisation and natural membrane turnover, there is a maximum level of internalisation that should characterise the antibodies of interest. This maximum level is expressed as the percentage of antibodies administered to an in vitro or in vivo sample or patient that are internalised into a cell or cells over a given time period.

For example, the antibody should exhibit a maximum internalisation into a cell of 10% after 30 minutes and/or 40% after one hour and/or 50% after two hours. Preferably, internalisation is at most 20% after 30 minutes. Alternatively the antibody should exhibit a maximum internalisation into the cell of between 10-50% (e.g. 10, 15, 20, 25, 30, 35, 40, 45 or 50%) after 30 minutes, and/or between 40-50% (e.g. 40, 45, or 50%) after one hour. In one embodiment the antibody should exhibit these levels of maximum internalisation in CLL cells.

The amount of internalisation can readily be measured using FACS (see Examples).

In a second aspect of the invention there is provided a nucleotide sequence encoding an antibody of the first aspect.

The terms "nucleotide sequence" or "nucleic acid" or "polynucleotide" or "oligonucleotide" are used interchangeably and refer to a heteropolymer of nucleotides or the sequence of these nucleotides. These phrases also refer to DNA or RNA of genomic or synthetic origin which may be single-stranded or double-stranded and may represent the sense or the antisense strand, to peptide nucleic acid (PNA) or to any DNA-like or RNA-like material. In the sequences herein A is adenine, C is cytosine, T is thymine, G is guanine and N is A, C, G or T (U). It is contemplated that where the polynucleotide is RNA, the T (thymine) in the sequences provided herein is substituted with U (uracil). Generally, nucleic acid segments provided by this invention may be assembled from fragments of the genome and short oligonucleotide linkers, or from a series of oligonucleotides, or from individual nucleotides, to provide a synthetic nucleic acid which is capable of being expressed in a recombinant transcriptional unit comprising regulatory elements derived from a microbial or viral operon, or a eukaryotic gene.

Suitable nucleotide sequences are provided in FIGS. 4 to 16:

ROR1-007-B03-VH
ROR1-007-B03-VL
(FIG. 4)
ROR1-007-008-VH
ROR1-007-008-VL
(FIG. 5)
ROR1-007-E06-VH
ROR1-007-E06-VL
(FIG. 6)
ROR1-007-H03-VH
ROR1-007-H03-VL
(FIG. 7)
ROR1-008-A03-VH
ROR1-008-A03-VL
(FIG. 8)
ROR1-008-D04-VH
ROR1-008-D04-VL
(FIG. 9)
ROR1-008-G04-VH
ROR1-008-G04-VL
(FIG. 10)
ROR1-008-H06-VH
ROR1-008-H06-VL
(FIG. 11)
ROR1-009-G03-VH
ROR1-009-G03-VL
(FIG. 12)
ROR1-009-G11-VH
ROR1-009-G11-VL
(FIG. 13)
ROR1-010-D05-VH
ROR1-010-D05-VL
(FIG. 14)
ROR1-010-D06-VH
ROR1-010-D06-VL
(FIG. 15)
ROR1-011-F01-VH
ROR1-011-F01-VL
(FIG. 16)

Preferably the antibodies have an EC50 lower than 20 nM as measured in an ELISA based system measuring binding towards a recombinant protein.

In a third aspect of the invention there is provided an expression vector containing a nucleotide sequence as described in the second aspect of the invention, and which may be used to express an antibody of the invention.

Typical prokaryotic vector plasmids are: pUC18, pUC19, pBR322 and pBR329 available from Biorad Laboratories (Richmond, Calif., USA); pTrc99A, pKK223-3, pKK233-3, pDR540 and pRIT5 available from Pharmacia (Piscataway, N.J., USA); pBS vectors, Phagescript vectors, Bluescript vectors, pNH8A, pNH16A, pNH18A, pNH46A available from Stratagene Cloning Systems (La Jolla, Calif. 92037, USA).

A typical mammalian cell vector plasmid is pSVL available from Pharmacia (Piscataway, N.J., USA). This vector uses the SV40 late promoter to drive expression of cloned genes, the highest level of expression being found in T antigen-producing cells, such as COS-1 cells. An example of an inducible mammalian expression vector is pMSG, also available from Pharmacia (Piscataway, N.J., USA). This vector uses the glucocorticoid-inducible promoter of the mouse mammary tumour virus long terminal repeat to drive expression of the cloned gene.

Useful yeast plasmid vectors are pRS403-406 and pRS413-416 and are generally available from Stratagene Cloning Systems (La Jolla, Calif. 92037, USA). Plasmids pRS403, pRS404, pRS405 and pRS406 are Yeast Integrating plasmids (YIps) and incorporate the yeast selectable markers HIS3, TRP1, LEU2 and URA3. Plasmids pRS413-416 are Yeast Centromere plasmids (YCps).

Methods well known to those skilled in the art can be used to construct expression vectors containing the coding sequence and, for example appropriate transcriptional or translational controls. One such method involves ligation via homopolymer tails. Homopolymer polydA (or polydC) tails are added to exposed 3' OH groups on the DNA fragment to be cloned by terminal deoxynucleotidyl transferases. The fragment is then capable of annealing to the polydT (or polydG) tails added to the ends of a linearised plasmid vector. Gaps left following annealing can be filled by DNA polymerase and the free ends joined by DNA ligase.

Another method involves ligation via cohesive ends. Compatible cohesive ends can be generated on the DNA fragment and vector by the action of suitable restriction enzymes. These ends will rapidly anneal through complementary base pairing and remaining nicks can be closed by the action of DNA ligase.

A further method uses synthetic molecules called linkers and adaptors. DNA fragments with blunt ends are generated by bacteriophage T4 DNA polymerase or *E. coli* DNA polymerase I which remove protruding 3' termini and fill in recessed 3' ends. Synthetic linkers, pieces of blunt-ended double-stranded DNA which contain recognition sequences for defined restriction enzymes, can be ligated to blunt-ended DNA fragments by T4 DNA ligase. They are subsequently digested with appropriate restriction enzymes to create cohesive ends and ligated to an expression vector with compatible termini. Adaptors are also chemically synthesised DNA fragments which contain one blunt end used for ligation but which also possess one preformed cohesive end.

Synthetic linkers containing a variety of restriction endonuclease sites are commercially available from a number of sources including International Biotechnologies Inc, New Haven, Conn., USA.

A desirable way to modify the DNA encoding the polypeptide of the invention is to use the polymerase chain reaction as disclosed by Saiki et al (1988) *Science* 239, 487-491. In this method the DNA to be enzymatically amplified is flanked by two specific oligonucleotide primers which themselves become incorporated into the amplified DNA. The said specific primers may contain restriction endonuclease recognition sites which can be used for cloning into expression vectors using methods known in the art.

In a fourth aspect of the invention there is provided a host cell comprising a nucleotide sequence or expression vector as described in the second and third aspects of the invention.

The DNA is then expressed in a suitable host to produce a polypeptide comprising the compound of the invention. Thus, the DNA encoding the polypeptide constituting the compound of the invention may be used in accordance with known techniques, appropriately modified in view of the teachings contained herein, to construct an expression vector, which is then used to transform an appropriate host cell for the expression and production of the polypeptide of the invention. Such techniques include those disclosed in U.S. Pat. No. 4,440,859 issued 3 Apr. 1984 to Rutter et al, U.S. Pat. No. 4,530,901 issued 23 Jul. 1985 to Weissman, U.S. Pat. No. 4,582,800 issued 15 Apr. 1986 to Crowl, U.S. Pat. No. 4,677,063 issued 30 Jun. 1987 to Mark et al, U.S. Pat. No. 4,678,751 issued 7 Jul. 1987 to Goeddel, U.S. Pat. No. 4,704,362 issued 3 Nov. 1987 to Itakura et al, U.S. Pat. No. 4,710,463 issued 1 Dec. 1987 to Murray, U.S. Pat. No. 4,757,006 issued 12 Jul. 1988 to Toole, Jr. et al, U.S. Pat. No. 4,766,075 issued 23 Aug. 1988 to Goeddel et al and U.S. Pat. No. 4,810,648 issued 7 Mar. 1989 to Stalker, all of which are incorporated herein by reference.

The DNA encoding the polypeptide constituting the compound of the invention may be joined to a wide variety of other DNA sequences for introduction into an appropriate host. The companion DNA will depend upon the nature of the host, the manner of the introduction of the DNA into the host, and whether episomal maintenance or integration is desired.

Generally, the DNA is inserted into an expression vector, such as a plasmid, in proper orientation and correct reading frame for expression. If necessary, the DNA may be linked to the appropriate transcriptional and translational regulatory control nucleotide sequences recognised by the desired host, although such controls are generally available in the expression vector. Thus, the DNA insert may be operatively linked to an appropriate promoter. Bacterial promoters include the *E. coli* lad and lacZ promoters, the T3 and 17 promoters, the gpt promoter, the phage λ PR and PL promoters, the phoA promoter and the trp promoter. Eukaryotic promoters include the CMV immediate early promoter, the HSV thymidine kinase promoter, the early and late SV40 promoters and the promoters of retroviral LTRs. Other suitable promoters will be known to the skilled artisan. The expression constructs will desirably also contain sites for transcription initiation and termination, and in the transcribed region, a ribosome binding site for translation. (WO 98/16643)

The vector is then introduced into the host through standard techniques. Generally, not all of the hosts will be transformed by the vector and it will therefore be necessary to select for transformed host cells. One selection technique involves incorporating into the expression vector a DNA sequence marker, with any necessary control elements, that codes for a selectable trait in the transformed cell. These markers include dihydrofolate reductase, G418 or neomycin resistance for eukaryotic cell culture, and tetracyclin, kanamycin or ampicillin resistance genes for culturing in *E. coli* and other bacteria. Alternatively, the gene for such selectable trait can be on another vector, which is used to co-transform the desired host cell.

Host cells that have been transformed by the recombinant DNA of the invention are then cultured for a sufficient time and under appropriate conditions known to those skilled in the art in view of the teachings disclosed herein to permit the expression of the polypeptide, which can then be recovered.

The polypeptide of the invention can be recovered and purified from recombinant cell cultures by well-known methods including ammonium sulphate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

Many expression systems are known, including (but not limited to) systems employing: bacteria (eg. *E. coli* and *Bacillus subtilis*) transformed with, for example, recombinant bacteriophage, plasmid or cosmid DNA expression vectors; yeasts (eg. *Saccaromyces cerevisiae*) transformed with, for example, yeast expression vectors; insect cell systems transformed with, for example, viral expression vectors (eg. baculovirus); plant cell systems transfected with, for example viral or bacterial expression vectors; animal cell systems transfected with, for example, adenovirus expression vectors.

The vectors can include a prokaryotic replicon, such as the Col E1 ori, for propagation in a prokaryote, even if the vector is to be used for expression in other, non-prokaryotic cell types. The vectors can also include an appropriate promoter such as a prokaryotic promoter capable of directing the expression (transcription and translation) of the genes in a bacterial host cell, such as *E. coli*, transformed therewith.

A promoter is an expression control element formed by a DNA sequence that permits binding of RNA polymerase and transcription to occur. Promoter sequences compatible with exemplary bacterial hosts are typically provided in plasmid vectors containing convenient restriction sites for insertion of a DNA segment of the present invention.

In a fifth aspect of the invention there is provided the use of an antibody as described in the first aspect of the invention in the induction of cell death.

In a sixth aspect of the invention there is provided a method of inducing cell death in one or more cells comprising exposing a cell expressing ROR1 to an antibody as described in the first aspect of the invention.

In a seventh aspect of the invention there is provided an antibody as described in the first aspect of the invention for use in medicine.

In an eighth aspect of the invention there is provided an antibody as described in the first aspect of the invention for use in treating Chronic Lymphocytic Leukaemia, Acute lymphocytic leukaemia, Acute myeloid leukaemia, non-Hodgkins lymphomas, chronic myeloid leukaemia, multiple myeloma, ovarian carcinoma, prostate cancer, breast cancer, melanoma, lung cancer, colorectal cancer, glioblastoma, pancreatic cancer, renal cell carcinoma, endometrial cancer, head and neck cancer and hepatocellular cancer.

By "treatment" we include the meanings that the number of cancer cells characterising the disease to be treated is reduced and/or further cancer cell growth is retarded and/or prevented and/or cancer cells are killed.

Chronic Lymphocytic Leukemia can be identified using the following criteria:

The World Health Organisation (WHO) Classification of Neoplasms of the Haematopoietic and Lymphoid Tissues (Harris N L et al., *Histopathology* 2000; 36:69-86). The diagnosis of CLL (n-100) is based on immunophenotyping (CD5+/CD19+/CD23+/IgM+) and the presence of >5.0×10$^9$/l lymphocytes in peripheral blood.

Patients with CLL are considered to have progressive disease according to a modification of the criteria of the NCI committee National Cancer Institute-sponsored working group guidelines for chronic lymphocytic leukaemia: revised guidelines for diagnosis and treatment. Cheson B et al, Blood 87, 4990-4997, 1996, whereby if there was a progression during the preceding 3 months in disease-related anaemia (haemoglobin <10.0 g/dl), thrombocytopenia (<100×10$^9$/l and/or an increase in spleen/liver/lymph-node size and/or more than a two-fold increase in the blood lymphocyte count. When these criteria are not fulfilled, the patients are considered as having non-progressive disease.

In a ninth aspect of the invention there is provided the use of an antibody as described in the first aspect of the invention in the manufacture of a medicament for treating Chronic Lymphocytic Leukaemia, Acute lymphocytic leukaemia, Acute myeloid leukaemia, non-Hodgkins lymphomas, chronic myeloid leukaemia, multiple myeloma, ovarian carcinoma, prostate cancer, breast cancer, melanoma, lung cancer, colorectal cancer, glioblastoma, pancreatic cancer and hepatocellular cancer.

The antibodies of the invention can be used to manufacture a pharmaceutical composition (medicament) that can be used to treat diseases such as Chronic Lymphocytic Leukaemia, Acute lymphocytic leukaemia, Acute myeloid leukaemia, non-Hodgkins lymphomas, chronic myeloid leukaemia, multiple myeloma, ovarian carcinoma, prostate cancer, breast cancer, melanoma, lung cancer, colorectal cancer, glioblastoma, pancreatic cancer and hepatocellular cancer.

In a tenth aspect of the invention there is provided a method of treating a disease comprising the step of administering to a subject an antibody as described in the first aspect of the invention, wherein the disease is selected from Chronic Lymphocytic Leukaemia, Acute lymphocytic leukaemia, Acute myeloid leukaemia, non-Hodgkins lymphomas, chronic myeloid leukaemia, multiple myeloma, ovarian carcinoma, prostate cancer, breast cancer, melanoma, lung cancer, colorectal cancer, glioblastoma, pancreatic cancer and hepatocellular cancer.

The term "subject" means all animals including humans. Examples of subjects include humans, cows, dogs, cats, goats, sheep, and pigs. The term "patient" means a subject having a disorder in need of treatment.

The disease to be treated may be progressive, i.e. that the disease worsens over time (i.e. is not stable or does not improve). In the case of CLL, patients are considered to have progressive disease if the following criteria were met: progression during the preceding 3 months in disease-related anaemia (haemoglobin <100 g/l), thrombocytopenia (<100×10$^9$/l) and/or an increase in spleen/liver/lymph-node size and/or more than a 2-fold increase in the blood lymphocyte count, if not the patients were considered non-progressive.

In an eleventh aspect of the invention there is provided a pharmaceutical composition comprising an antibody as described in the first aspect of the invention and a pharmaceutically acceptable excipient, diluent or carrier.

The examples describe some methods of producing pharmaceutical formulations, however the skilled person will appreciate that the most appropriate formulation will depend on a number of factors including route of administration, patient type (e.g. patient age, weight/size).

Preferably the pharmaceutical composition induces cell death in a cell expressing ROR1.

In a twelfth aspect of the invention there is provided a kit of parts comprising:
(i) an antibody as described in the first aspect of the invention or a pharmaceutical composition as described in the eleventh aspect of the invention;
(ii) apparatus for administering the antibody or pharmaceutical composition comprising the antibody; and
(iii) instructions for use.

EMBODIMENTS OF THE INVENTION

Embodiments of the invention are described in the following numbered paragraphs.
1. An anti-ROR1 antibody capable of inducing cell death in a cell expressing ROR1.
2. An antibody as described in paragraph 1 wherein the antibody binds specifically to either an extracellular domain of ROR1, an intracellular domain of ROR1 or to a nucleotide sequence encoding ROR1.
3. An antibody as described in paragraph 1 or 2 wherein the antibody is either a complete antibody or a fragment thereof.
4. An antibody as described in any previous paragraph wherein cell death is induced on specific binding of the antibody to ROR1 or the nucleotide sequence encoding ROR1.
5. An antibody as described in any of paragraphs 1 to 4 wherein the extracellular domain to which the antibody binds has the amino acid sequence WNISSELNKDSYLTL (SEQ ID NO: 1).
6. An antibody as described in any of paragraphs 1 to 4 wherein the intracellular domain to which the antibody binds has the amino acid sequence NKSQKPYKIDSKQAS (SEQ ID NO: 2).
7. An antibody as described in any previous paragraph comprising the combination of $V_H$ and $V_L$ region amino acid sequences shown in one of:
   FIG. 4 (ROR1-007-B03-VH and ROR1-007-B03-VL)
   FIG. 5 (ROR1-007-008-VH and ROR1-007-008-VL)
   FIG. 6 (ROR1-007-E06-VH and ROR1-007-E06-VL)

FIG. 7 (ROR1-007-H03-VH and ROR1-007-H03-VL)
FIG. 8 (ROR1-008-A03-VH and ROR1-008-A03-VL)
FIG. 9 (ROR1-008-D04-VH and ROR1-008-D04-VL)
FIG. 10 (ROR1-008-G04-VH and ROR1-008-G04-VL)
FIG. 11 (ROR1-008-H06-VH and ROR1-008-H06-VL)
FIG. 12 (ROR1-009-G03-VH and ROR1-009-G03-VL)
FIG. 13 (ROR1-009-G11-VH and ROR1-009-G11-VL)
FIG. 14 (ROR1-010-D05-VH and ROR1-010-D05-VL)
FIG. 15 (ROR1-010-D06-VH and ROR1-010-D06-VL)
FIG. 16 (ROR1-011-F01-VH and ROR1-011-F01-VL)

8. An antibody as described in any previous paragraph comprising the combination of all six CDR regions (CDRH1, CDRH2, CDRH3, CDRL1, CDRL2 and CDRL3) shown in one of:
FIG. 4 (ROR1-007-B03-VH and ROR1-007-B03-VL)
FIG. 5 (ROR1-007-008-VH and ROR1-007-008-VL)
FIG. 6 (ROR1-007-E06-VH and ROR1-007-E06-VL)
FIG. 7 (ROR1-007-H03-VH and ROR1-007-H03-VL)
FIG. 8 (ROR1-008-A03-VH and ROR1-008-A03-VL)
FIG. 9 (ROR1-008-D04-VH and ROR1-008-D04-VL)
FIG. 10 (ROR1-008-G04-VH and ROR1-008-G04-VL)
FIG. 11 (ROR1-008-H06-VH and ROR1-008-H06-VL)
FIG. 12 (ROR1-009-G03-VH and ROR1-009-G03-VL)
FIG. 13 (ROR1-009-G11-VH and ROR1-009-G11-VL)
FIG. 14 (ROR1-010-D05-VH and ROR1-010-D05-VL)
FIG. 15 (ROR1-010-D06-VH and ROR1-010-D06-VL)
FIG. 16 (ROR1-011-F01-VH and ROR1-011-F01-VL)

9. An antibody as described in any of paragraphs 1 to 8 comprising at least one, preferably 2, 3, 4, 5 or 6 of the CDR regions shown in FIGS. 4 to 16:
FIG. 4 (ROR1-007-B03-VH and ROR1-007-B03-VL)
FIG. 5 (ROR1-007-008-VH and ROR1-007-008-VL)
FIG. 6 (ROR1-007-E06-VH and ROR1-007-E06-VL)
FIG. 7 (ROR1-007-H03-VH and ROR1-007-H03-VL)
FIG. 8 (ROR1-008-A03-VH and ROR1-008-A03-VL)
FIG. 9 (ROR1-008-D04-VH and ROR1-008-D04-VL)
FIG. 10 (ROR1-008-G04-VH and ROR1-008-G04-VL)
FIG. 11 (ROR1-008-H06-VH and ROR1-008-H06-VL)
FIG. 12 (ROR1-009-G03-VH and ROR1-009-G03-VL)
FIG. 13 (ROR1-009-G11-VH and ROR1-009-G11-VL)
FIG. 14 (ROR1-010-D05-VH and ROR1-010-D05-VL)
FIG. 15 (ROR1-010-D06-VH and ROR1-010-D06-VL)
FIG. 16 (ROR1-011-F01-VH and ROR1-011-F01-VL)

10. An antibody as described in any of paragraphs 7 to 9 further comprising the constant regions $C_H$ and $C_L$ have the amino acid sequences as shown in FIG. 3.

11. An antibody as described in any previous paragraph having an EC50 lower than 20 nM as measured in an ELISA based system measuring binding towards a recombinant protein.

12. An antibody that competitively binds to the same epitope as the antibodies of paragraphs 1 to 11.

13. An antibody as described in any previous paragraph wherein the antibody exhibits a maximum internalisation into a cell of 10% after 30 minutes and/or 20% after 30 minutes and/or 40% after one hour and/or 50% after two hours.

14. A nucleotide sequence encoding an antibody as described in any previous paragraph.

15. A nucleotide sequence as described in paragraph 14 wherein the nucleotide sequences are as shown in FIGS. 4 to 16.

16. An expression vector containing a nucleotide sequence as described in paragraph 14 or 15.

17. A host cell comprising a nucleotide sequence or expression vector as described in paragraphs 14 to 16.

18. Use of an antibody as defined in paragraphs 1 to 12 in the induction of cell death of a cell.

19. A method of inducing cell death in one or more cells comprising exposing a cell expressing ROR1 to an antibody as defined in paragraphs 1 to 13.

20. An antibody as defined in paragraphs 1 to 13 for use in medicine.

21. An antibody as defined in paragraphs 1 to 13 for use in treating a disease selected from Chronic Lymphocytic Leukaemia, Acute lymphocytic leukaemia, Acute myeloid leukaemia, non-Hodgkin lymphomas, chronic myeloid, multiple myeloma, ovarian carcinoma, prostate cancer, breast cancer, melanoma, lung cancer, colorectal cancer, glioblastoma, pancreatic cancer, renal cell carcinoma, endometrial cancer, head and neck cancer and hepatocellular cancer.

22. Use of an antibody as defined in paragraphs 1 to 13 in the manufacture of a medicament for treating a disease selected from Chronic Lymphocytic Leukaemia, Acute lymphocytic leukaemia, Acute myeloid leukaemia, non-Hodgkin lymphomas, chronic myeloid, multiple myeloma, ovarian carcinoma, prostate cancer, breast cancer, melanoma, lung cancer, colorectal cancer, glioblastoma, pancreatic cancer, renal cell carcinoma, endometrial cancer, head and neck cancer and hepatocellular cancer.

23. A method of treating a disease comprising the step of administering to a subject an antibody as described in paragraphs 1 to 13, wherein the disease is selected from Chronic Lymphocytic Leukaemia, Acute lymphocytic leukaemia, Acute myeloid leukaemia, non-Hodgkin lymphomas, chronic myeloid, multiple myeloma, ovarian carcinoma, prostate cancer, breast cancer, melanoma, lung cancer, colorectal cancer, glioblastoma, pancreatic cancer, renal cell carcinoma, endometrial cancer, head and neck cancer and hepatocellular cancer and hepatocellular cancer.

24. An antibody, use or method as described in paragraphs 21 to 23 wherein the disease is progressive.

25. An antibody, use or method as described in paragraphs 21 to 23 wherein the disease is Chronic Lymphocytic Leukaemia.

26. A pharmaceutical composition comprising an antibody as defined in paragraphs 1 to 13 and a pharmaceutically acceptable excipient, diluent or carrier.

27. A pharmaceutical composition as described in Paragraph 26 which induces cell death in a cell expressing ROR1.

28. A kit of parts comprising:
(i) an antibody as described in paragraphs 1 to 13 or a pharmaceutical composition as described in paragraphs 26 or 27;
(ii) apparatus for administering the antibody or pharmaceutical composition; and
(iii) instructions for use.

EXAMPLES

The following examples embody various aspects of the invention. It will be appreciated that the specific antibodies and/or antigens used in the examples serve to illustrate the principles of the invention and are not intended to limit its scope.

The following examples are described with reference to the accompanying figures in which:

The human ROR-1 gene has a coding region of 2814 bp which predicted 937 amino acids sequence and 105 kDa protein size including an Ig-like domain, cysteine-rich domain, kringle domain, tyrosine kinase domain, and proline-rich domain.

Positions of the antibody recognition site NKSQKPYKID-SKQAS (SEQ ID NO: 2) (Y) as well as the protein domains: Immunoglobulin like domain (Ig), cysteine rich domain (CRD), Kringle domain (Kr), transmembrane domain (TM), tyrosine kinase domain (TK), serine and threonine rich domain (S/T), and proline rich domain (P) are indicated.

Figure 1:
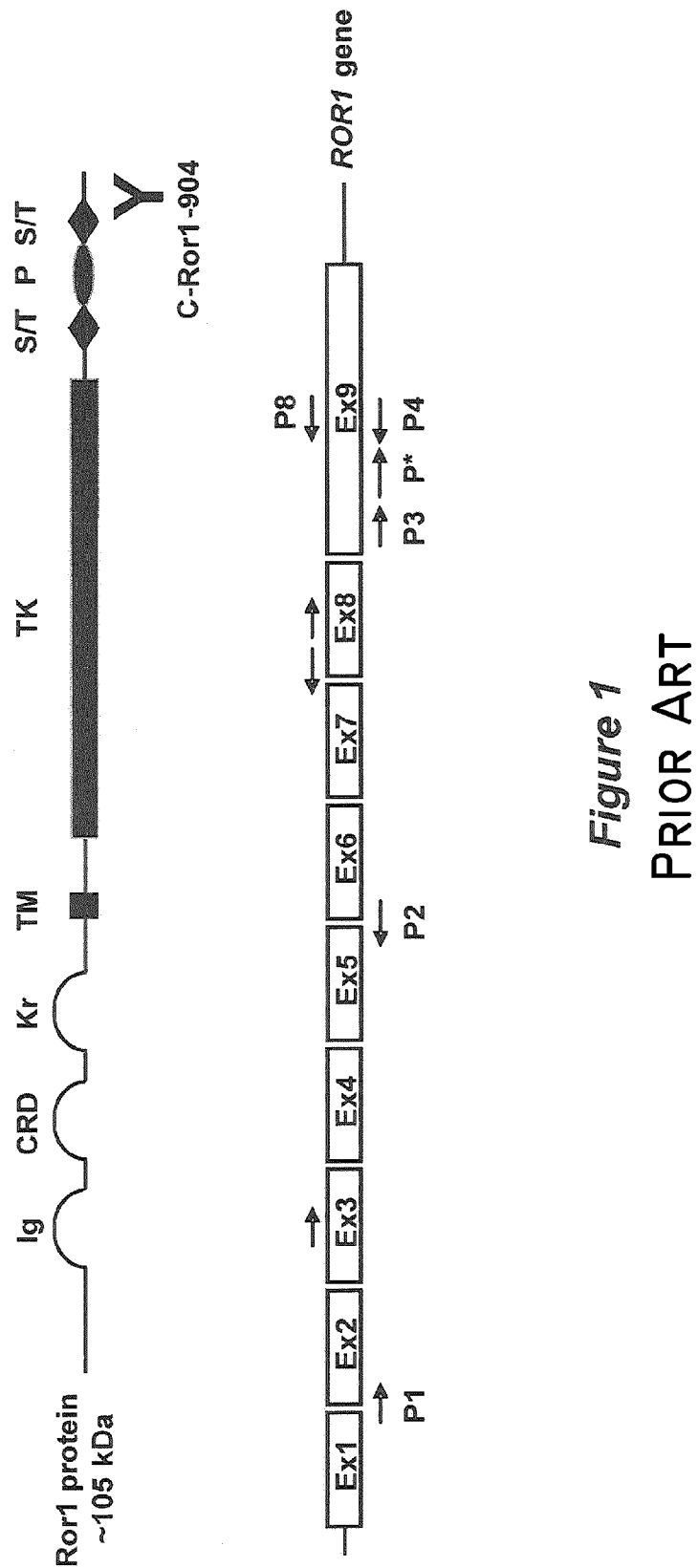
FIG. 1—Schematic presentation of the ROR1 gene and the Ror1 protein.
Figure 2:
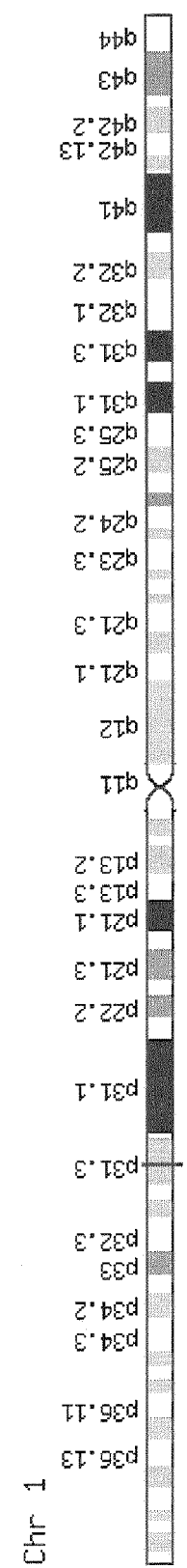

FIG. 2—Map of human chromosome 1 indicating part of the genes overexpressed in B-CLL.

FIG. 3—Amino acid sequences of constant regions: IgG1-CH (SEQ ID NO: 3), λ-CL (SEQ ID NO: 4).

FIGS. 4 to 16—amino acid and nucleotide sequences encoding the variable regions of anti-ROR1 antibodies. CDR regions are highlighted in boxes (and labeled as CDRH1, CDRH2, CDRH3, CDRL1, CDRL2 or CDRL3), and mutations in the framework regions are also marked in bold.

FIG. 4—(ROR1-007-B03-VH, amino acid sequence (SEQ ID NO: 5), nucleotide sequence (SEQ ID NO: 31); and ROR1-007-B03-VL, amino acid sequence (SEQ ID NO: 6), nucleotide sequence (SEQ ID NO: 32)). Shown within the VH chain are the CDRH1 sequence (SEQ ID NO: 57), the CDRH2 sequence (SEQ ID NO: 58) and the CDRH3 sequence (SEQ ID NO: 59). Shown within the VL chain are the CDRL1 sequence (SEQ ID NO: 60), the CDRL2 sequence (SEQ ID NO: 61) and the CDRL3 sequence (SEQ ID NO: 62).

FIG. 5—(ROR1-007-008-VH, amino acid sequence (SEQ ID NO: 7), nucleotide sequence (SEQ ID NO: 33); and ROR1-007-008-VL, amino acid sequence (SEQ ID NO: 8), nucleotide sequence (SEQ ID NO: 34)). Shown within the VH chain are the CDRH1 sequence (SEQ ID NO: 63), the CDRH2 sequence (SEQ ID NO: 64) and the CDRH3 sequence (SEQ ID NO: 65). Shown within the VL chain are the CDRL1 sequence (SEQ ID NO: 66), the CDRL2 sequence (SEQ ID NO: 67) and the CDRL3 sequence (SEQ ID NO: 68).

FIG. 6—(ROR1-007-E06-VH, amino acid sequence (SEQ ID NO: 9), nucleotide sequence (SEQ ID NO: 35); and ROR1-007-E06-VL, amino acid sequence (SEQ ID NO: 10), nucleotide sequence (SEQ ID NO: 36)). Shown within the VH chain are the CDRH1 sequence (SEQ ID NO: 69), the CDRH2 sequence (SEQ ID NO: 70) and the CDRH3 sequence (SEQ ID NO: 71). Shown within the VL chain are the CDRL1 sequence (SEQ ID NO: 72), the CDRL2 sequence (SEQ ID NO: 73) and the CDRL3 sequence (SEQ ID NO: 74).

FIG. 7—(ROR1-007-H03-VH, amino acid sequence (SEQ ID NO: 11), nucleotide sequence (SEQ ID NO: 37); and ROR1-007-H03-VL, amino acid sequence (SEQ ID NO: 12), nucleotide sequence (SEQ ID NO: 38)). Shown within the VH chain are the CDRH1 sequence (SEQ ID NO: 75), the CDRH2 sequence (SEQ ID NO: 76) and the CDRH3 sequence (SEQ ID NO: 77). Shown within the VL chain are the CDRL1 sequence (SEQ ID NO: 78), the CDRL2 sequence (SEQ ID NO: 79) and the CDRL3 sequence (SEQ ID NO: 80).

FIG. 8—(ROR1-008-A03-VH, amino acid sequence (SEQ ID NO: 13), nucleotide sequence (SEQ ID NO: 39); and ROR1-008-A03-VL, amino acid sequence (SEQ ID NO: 14), nucleotide sequence (SEQ ID NO: 40)). Shown within the VH chain are the CDRH1 sequence (SEQ ID NO: 81), the CDRH2 sequence (SEQ ID NO: 82) and the CDRH3 sequence (SEQ ID NO: 83). Shown within the VL chain are the CDRL1 sequence (SEQ ID NO: 84), the CDRL2 sequence (SEQ ID NO: 85) and the CDRL3 sequence (SEQ ID NO: 86).

FIG. 9—(ROR1-008-D04-VH, amino acid sequence (SEQ ID NO: 15), nucleotide sequence (SEQ ID NO: 41); and ROR1-008-D04-VL, amino acid sequence (SEQ ID NO: 16), nucleotide sequence (SEQ ID NO: 42)). Shown within the VH chain are the CDRH1 sequence (SEQ ID NO: 87), the CDRH2 sequence (SEQ ID NO: 88) and the CDRH3 sequence (SEQ ID NO: 89). Shown within the VL chain are the CDRL1 sequence (SEQ ID NO: 90), the CDRL2 sequence (SEQ ID NO: 91) and the CDRL3 sequence (SEQ ID NO: 92).

FIG. 10—(ROR1-008-G04-VH, amino acid sequence (SEQ ID NO: 17), nucleotide sequence (SEQ ID NO: 43); and ROR1-008-G04-VL, amino acid sequence (SEQ ID NO: 18), nucleotide sequence (SEQ ID NO: 44)). Shown within the VH chain are the CDRH1 sequence (SEQ ID NO: 93), the CDRH2 sequence (SEQ ID NO: 94) and the CDRH3 sequence (SEQ ID NO: 95). Shown within the VL chain are the CDRL1 sequence (SEQ ID NO: 86), the CDRL2 sequence (SEQ ID NO: 97) and the CDRL3 sequence (SEQ ID NO: 98).

FIG. 11—(ROR1-008-H06-VH, amino acid sequence (SEQ ID NO: 19), nucleotide sequence (SEQ ID NO: 45); and ROR1-008-H06-VL, amino acid sequence (SEQ ID NO: 20), nucleotide sequence (SEQ ID NO: 46)). Shown within the VH chain are the CDRH1 sequence (SEQ ID NO: 99), the CDRH2 sequence (SEQ ID NO: 100) and the CDRH3 sequence (SEQ ID NO: 101). Shown within the VL chain are the CDRL1 sequence (SEQ ID NO: 102), the CDRL2 sequence (SEQ ID NO: 103) and the CDRL3 sequence (SEQ ID NO: 104).

FIG. 12—(ROR1-009-G03-VH, amino acid sequence (SEQ ID NO: 21), nucleotide sequence (SEQ ID NO: 47); and ROR1-009-G03-VL, amino acid sequence (SEQ ID NO: 22), nucleotide sequence (SEQ ID NO: 48)). Shown within the VH chain are the CDRH1 sequence (SEQ ID NO: 105), the CDRH2 sequence (SEQ ID NO: 106) and the CDRH3 sequence (SEQ ID NO: 107). Shown within the VL chain are the CDRL1 sequence (SEQ ID NO: 108), the CDRL2 sequence (SEQ ID NO: 109) and the CDRL3 sequence (SEQ ID NO: 110).

FIG. 13—(ROR1-009-G11-VH, amino acid sequence (SEQ ID NO: 23), nucleotide sequence (SEQ ID NO: 49); and ROR1-009-G11-VL, amino acid sequence (SEQ ID NO: 24), nucleotide sequence (SEQ ID NO: 50)). Shown within the VH chain are the CDRH1 sequence (SEQ ID NO: 111), the CDRH2 sequence (SEQ ID NO: 112) and the CDRH3 sequence (SEQ ID NO: 113). Shown within the VL chain are the CDRL1 sequence (SEQ ID NO: 114), the CDRL2 sequence (SEQ ID NO: 115) and the CDRL3 sequence (SEQ ID NO: 116).

FIG. 14—(ROR1-010-D05-VH, amino acid sequence (SEQ ID NO: 25), nucleotide sequence (SEQ ID NO: 51); and ROR1-010-D05-VL, amino acid sequence (SEQ ID NO: 26), nucleotide sequence (SEQ ID NO: 52)). Shown within the VH chain are the CDRH1 sequence (SEQ ID NO: 117), the CDRH2 sequence (SEQ ID NO: 118) and the CDRH3 sequence (SEQ ID NO: 119). Shown within the VL chain are the CDRL1 sequence (SEQ ID NO: 120), the CDRL2 sequence (SEQ ID NO: 121) and the CDRL3 sequence (SEQ ID NO: 122).

FIG. 15—(ROR1-010-D06-VH, amino acid sequence (SEQ ID NO: 27), nucleotide sequence (SEQ ID NO: 53); and ROR1-010-D06-VL, amino acid sequence (SEQ ID NO: 28), nucleotide sequence (SEQ ID NO: 54)). Shown within the VH chain are the CDRH1 sequence (SEQ ID NO: 123), the CDRH2 sequence (SEQ ID NO: 124) and the CDRH3 sequence (SEQ ID NO: 125). Shown within the VL chain are the CDRL1 sequence (SEQ ID NO: 126), the CDRL2 sequence (SEQ ID NO: 127) and the CDRL3 sequence (SEQ ID NO: 128).

FIG. 16—(ROR1-011-F01-VH, amino acid sequence (SEQ ID NO: 29), nucleotide sequence (SEQ ID NO: 55); and ROR1-011-F01-VL, amino acid sequence (SEQ ID NO: 30), nucleotide sequence (SEQ ID NO: 56)). Shown within the VH chain are the CDRH1 sequence (SEQ ID NO: 129), the CDRH2 sequence (SEQ ID NO: 130) and the CDRH3 sequence (SEQ ID NO: 131). Shown within the VL chain are the CDRL1 sequence (SEQ ID NO: 132), the CDRL2 sequence (SEQ ID NO: 133) and the CDRL3 sequence (SEQ ID NO: 134).

FIGS. 17A-17D. Antibodies of the invention specifically bind ROR1

The antibodies were shown to bind to ROR1 protein but not to control protein as assayed by ELISA.

Figure 18A:
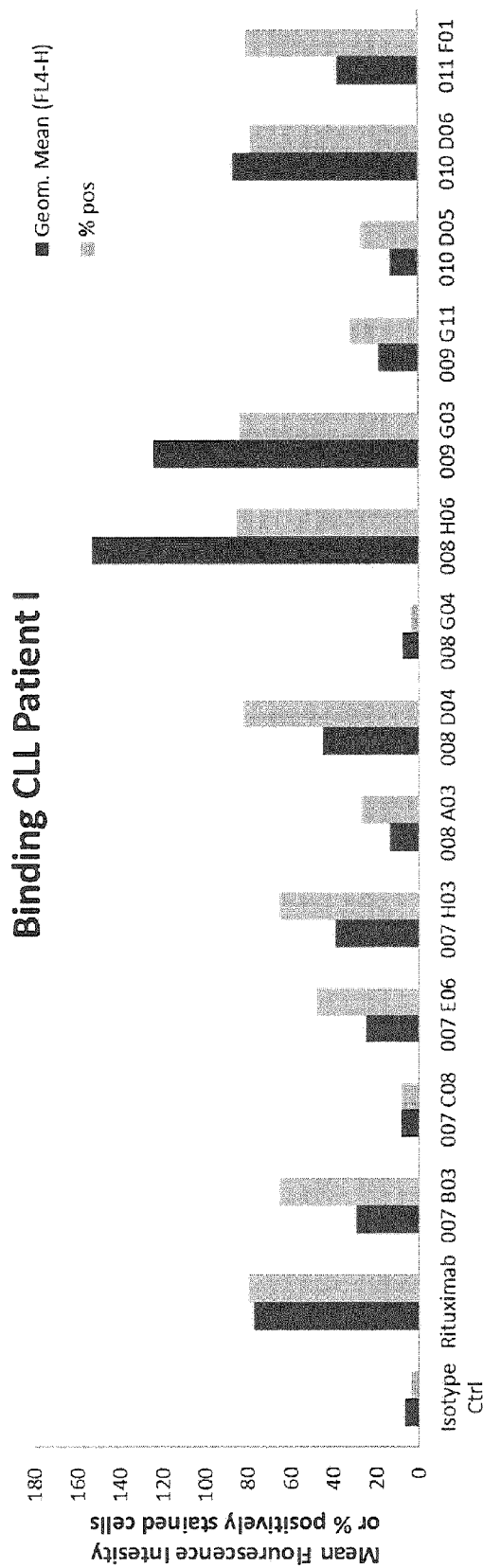
Figure 18B:
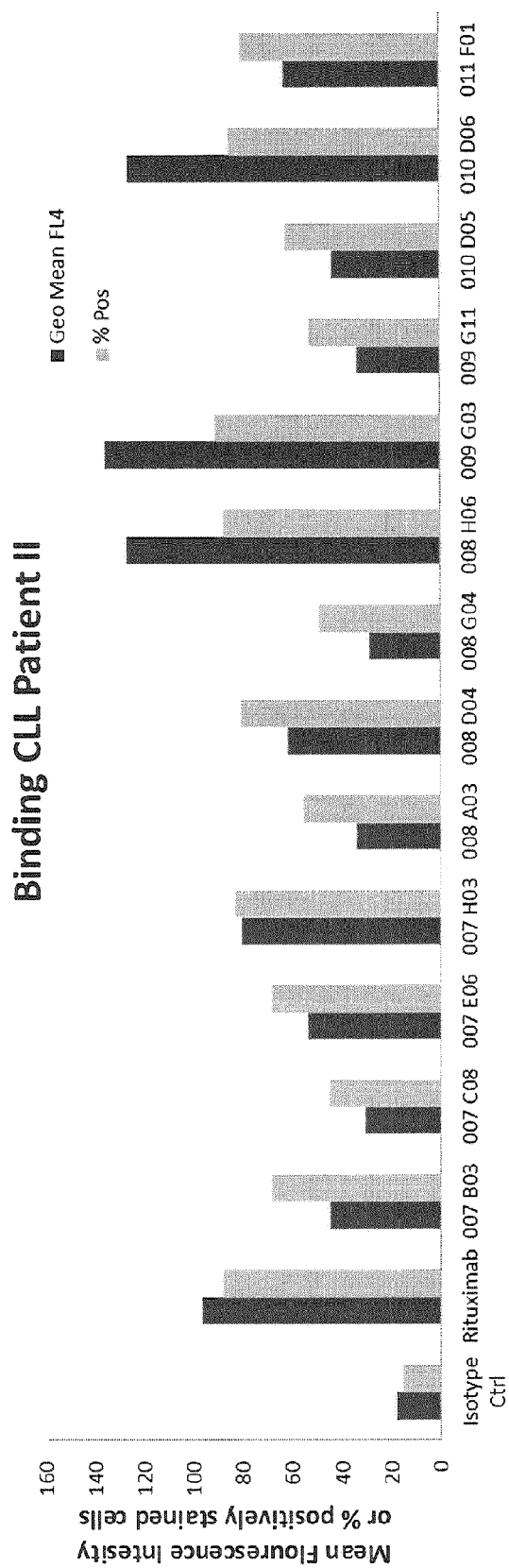

FIGS. 18A-18B. ROR1 specific antibodies bind primary CLL cells

The antibodies bind CLL cells obtained from peripheral blood of two CLL patients as measured by FACS. Black lines show the geometric mean of the fluorescent signal and the grey line show the percentage of positively stained cells. Rituximab staining is used as positive control.

Figure 19:
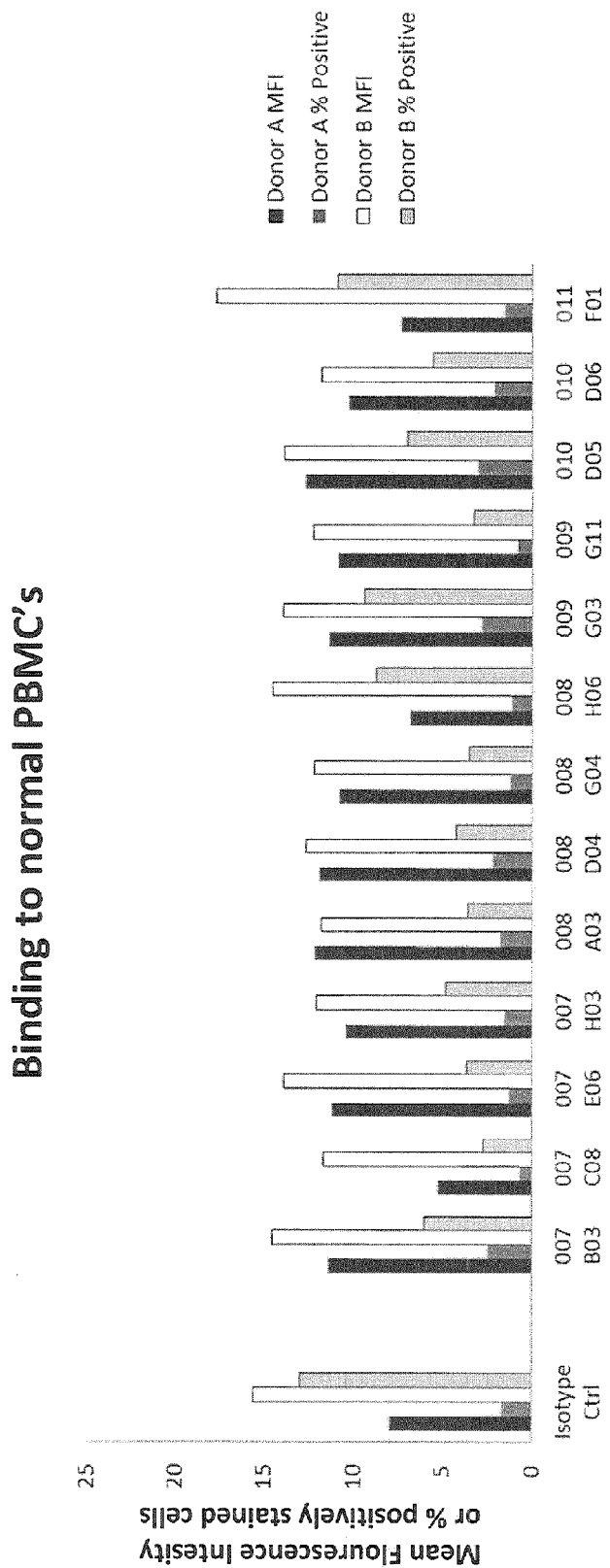

FIG. 19. ROR1 specific antibodies do not bind primary PBMC's from healthy volunteers The antibodies do not bind PBMC's cells obtained from peripheral blood of two healthy volunteers as measured by FACS. Black and white lines show the geometric mean of the fluorescent signal of the two different donors, and the grey lines show the percentage of positively stained cells.

FIG. 20. ROR-1 specific antibodies induce apoptosis of primary CLL cells

The antibodies induce apoptosis of CLL cells obtained from peripheral blood of two CLL patients. The CLL cells are incubated in duplicates with ROR-1 specific antibodies at 1 in the presence of crosslinking F(ab')2 fragments for 16 h. Thereafter the cells are stained with AnnexinV, measuring early apoptotic cells, as well as SYTOX, measuring late apoptotic, necrotic or by other means cells with a leaky cell membrane. Unstained cells are thereby counted as viable. *=p<0.001, =p<0.01, *=p<0.05 as calculated by ANOVA using Bonferronis correction for multiple analyses. The cytotoxic agent Paclitaxel and the CD20 specific therapeutic antibody Rituximab are used as positive controls.

Figure 21:
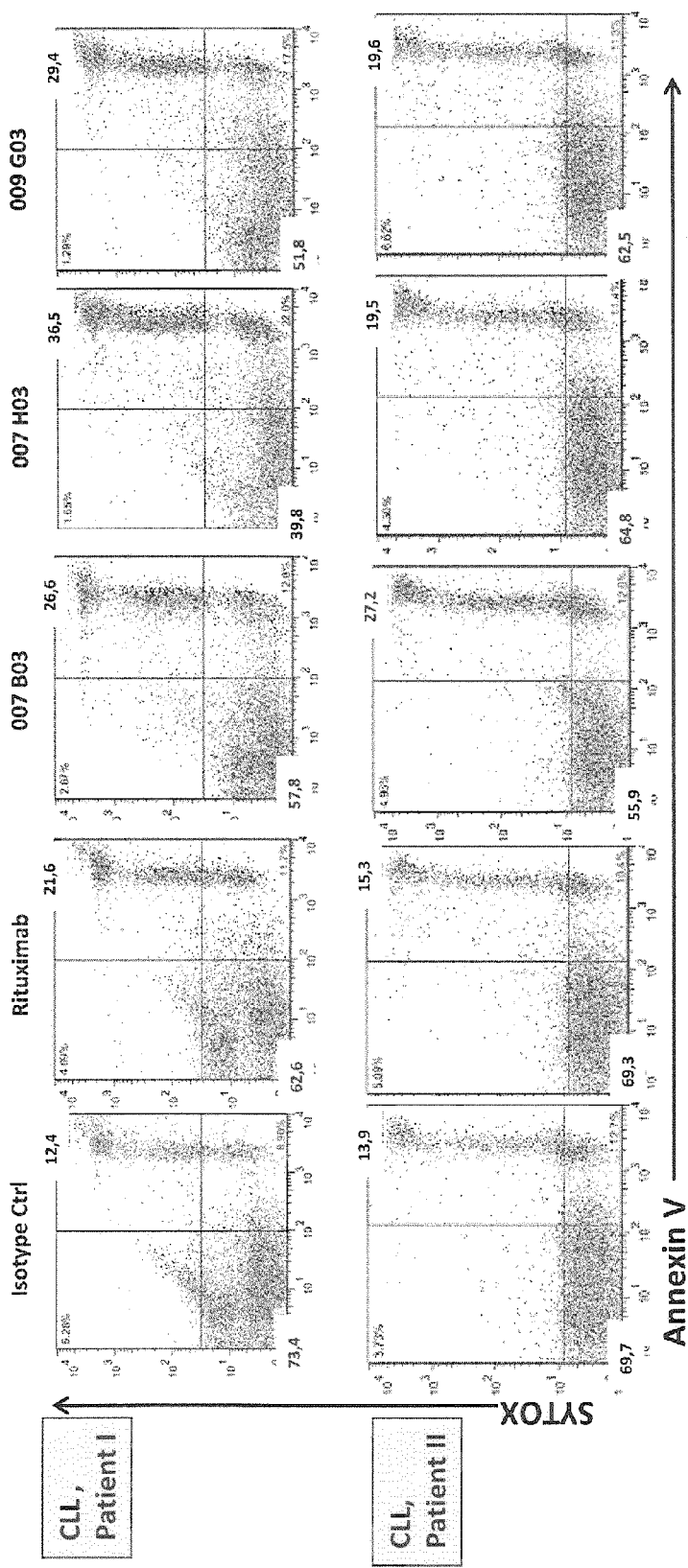

FIG. 21. Examples of FACS pictures for determination of primary CLL cell viability Cells located in the lower left quadrant of each panel are viable. Cells in the lower right are early apoptotic, cells in the upper left have a permeabilized cell membrane and are therefore not viable, and cells in the upper right are considered as late apoptotic or necrotic.

Figure 22:
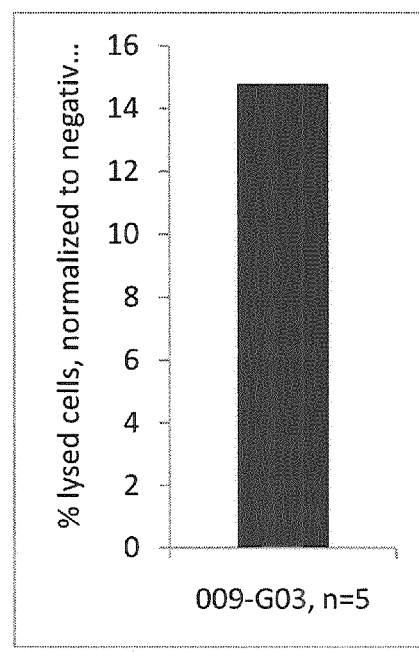

FIG. 22. ROR1 specific antibodies mediate NK dependent ADCC of primary patient CLL cells Primary patient CLL cells were used as target cells and primary NK cells isolated from buffy coats as effector cells and used at an 1:40 ratio. Target cells are loaded with Calcein prior to the assay and released calcein in the media is used to measure NK cell mediated lysis. Figure shows data summarized from 3 different CLL patients and NK cells from in total 5 donors±SEM.

Figure 23:
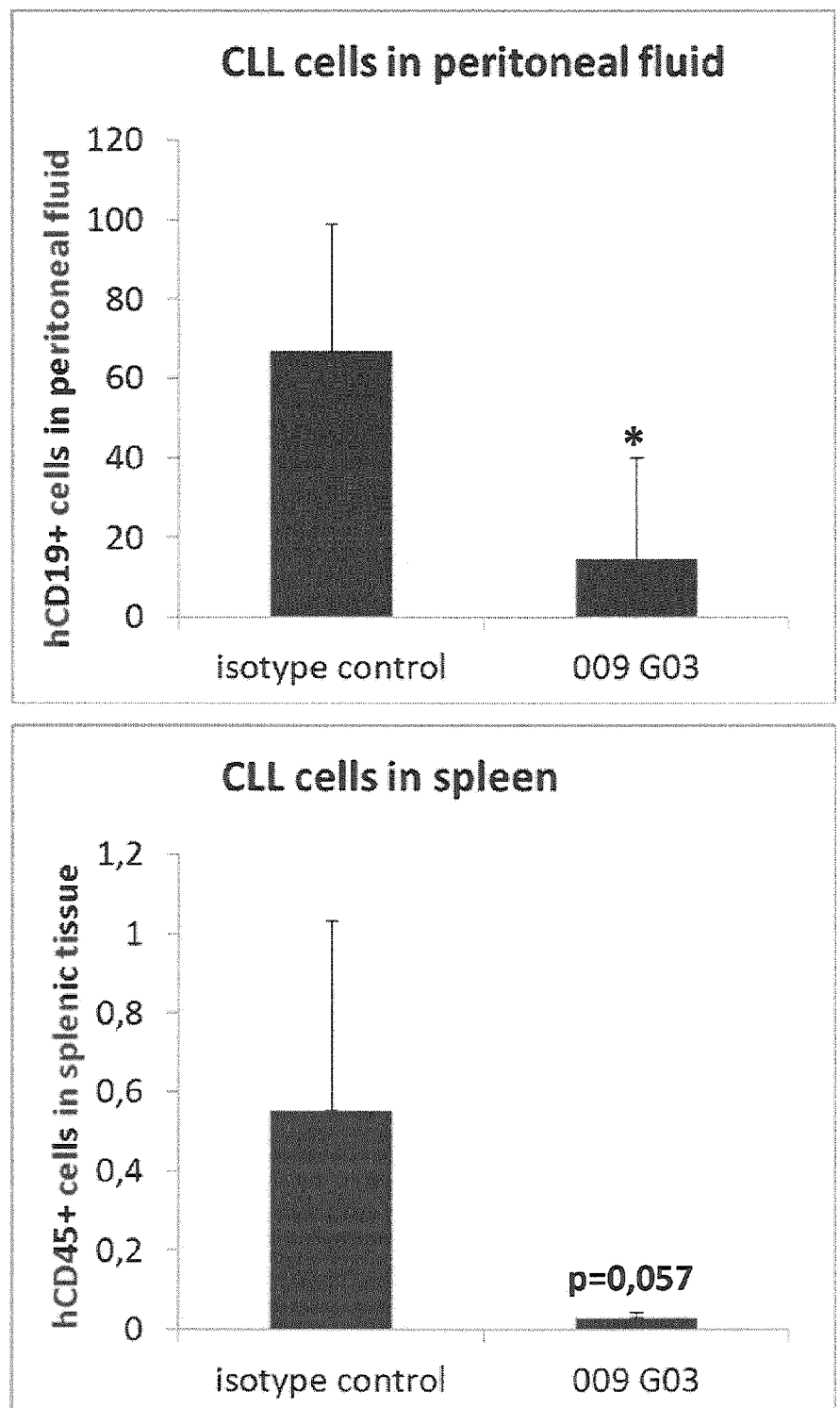

FIG. 23. ROR-1 specific antibodies deplete primary CLL cells transferred to immunodeficient mice.

Primary CLL cells isolated from patient 2 were transferred to immunodeficient NOD.SCID mice and treated with 10 mg/kg of the ROR-1 specific antibody 009-G03 on day 1 and 4 after transfer. At day 7, peritoneal fluid and spleens were collected and human CLL cells were quantified by triple staining for CD45, CD19 and CD5. The 009-G03 antibody significantly reduces the number of CLL cells in the peritoneal fluid. In addition, there is a very strong tendency to reduced numbers also in splenic tissue. N=4 mice/group *=p<0.05 as calculated by T test. Values in spleen are calculated using Mann-Whitney's test for non-parametric values (due to significant differences in variances).

Figure 24:
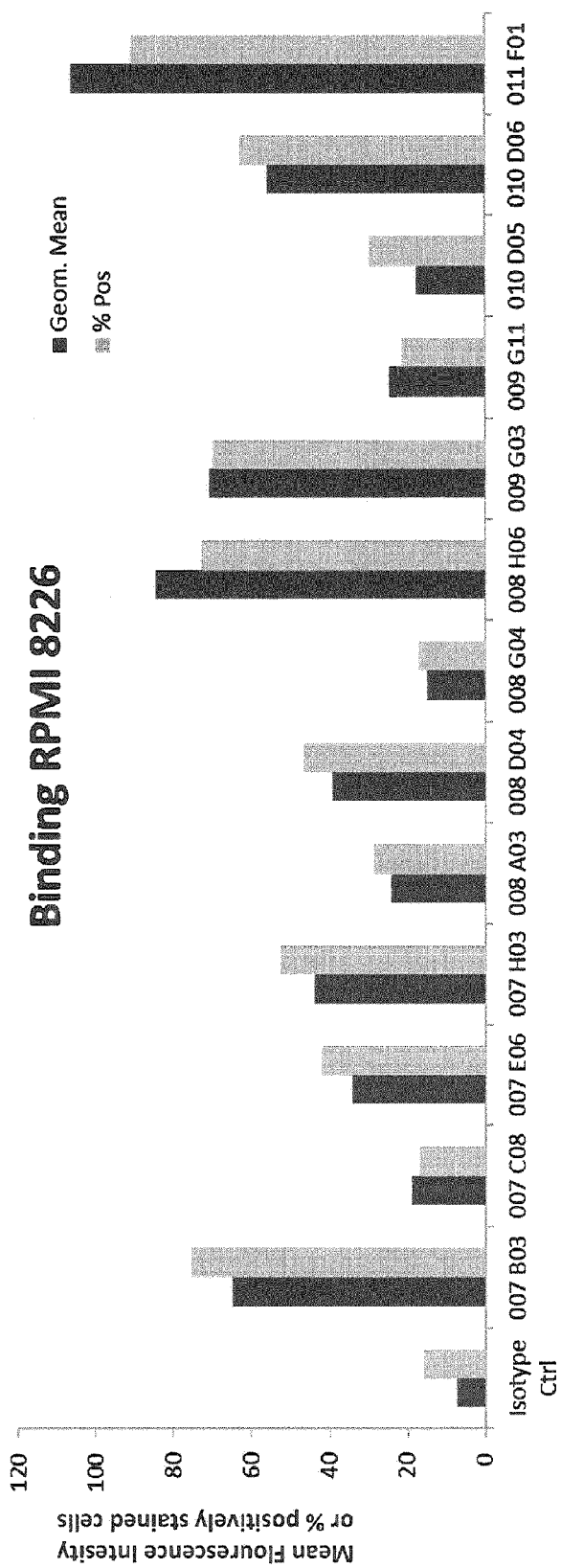

FIG. 24. ROR1 specific antibodies bind RPMI 8226 cells, a cell line for multiple myeloma.

The antibodies bind RPMI 8226 (ATCC Nr: CLL-155) cells as measured by FACS. Black lines show the geometric mean of the fluorescent signal and the grey line show the percentage of positively stained cells.

Figure 25:
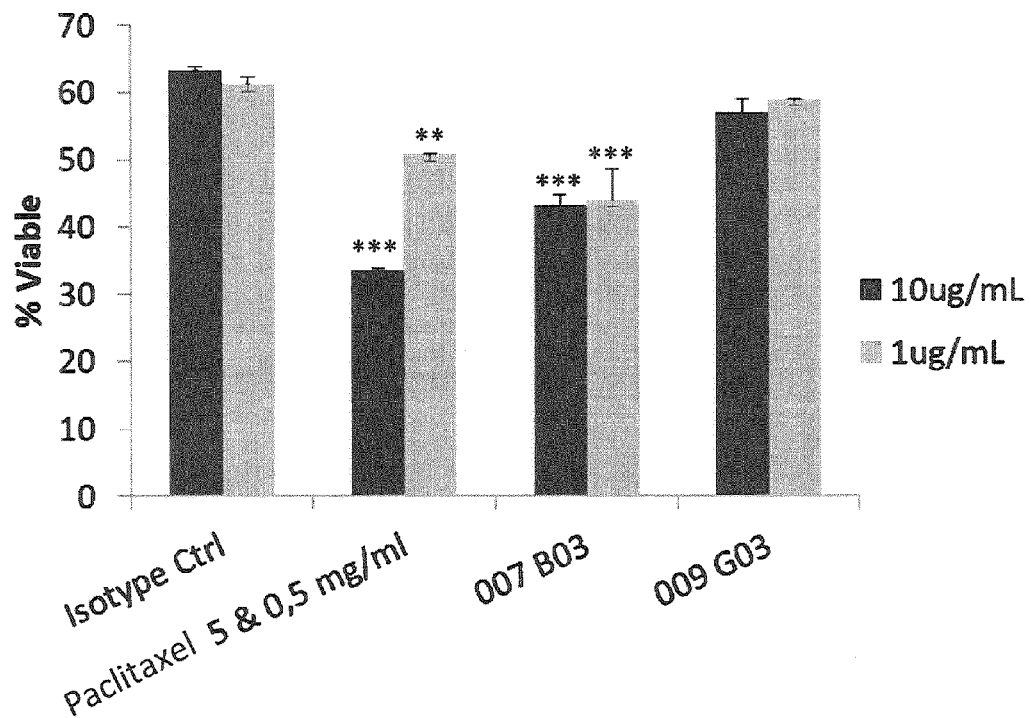

FIG. 25. ROR-1 specific antibodies induce apoptosis of RPMI 8226 cells, a cell line representative of multiple myeloma.

The antibodies induce apoptosis or RPMI 8226 cells. The cell line are incubated in duplicates with two ROR-1 specific antibodies at 10 or 1 μg/ml in the presence of crosslinking F(ab')2 fragments for 16 h. Thereafter the cells are stained with AnnexinV, measuring early apoptotic cells, as well as SYTOX, measuring late apoptotic, necrotic or by other means cells with a leaky cell membrane. Unstained cells are thereby counted as viable. *=p<0.001, =p<0.01 as calculated by ANOVA using Bonferronis correction for multiple analyses. The cytotoxic agent Paclitaxel are used as positive control.

Figure 26:
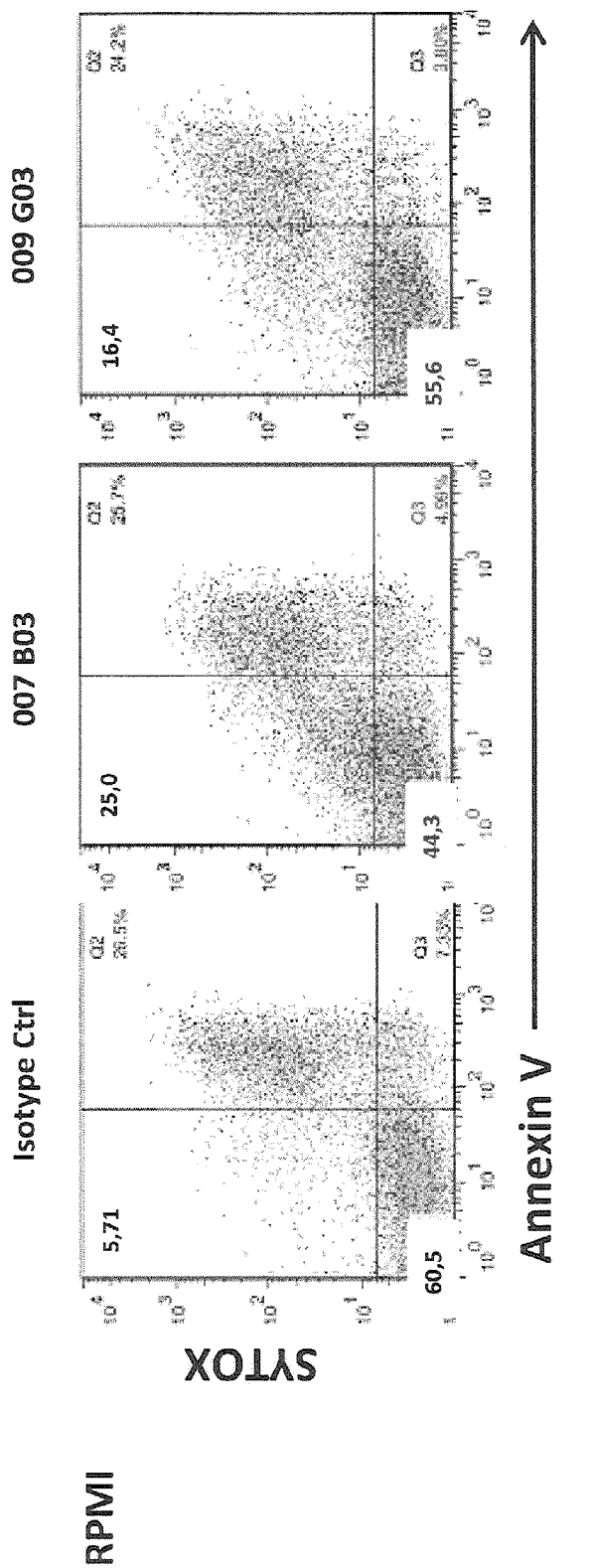

FIG. 26. Examples of FACS pictures for determination of RPMI8226 cell viability.

Cells located in the lower left quadrant of each panel are viable. Cells in the lower right are early apoptotic, cells in the upper left have a permeabilized cell membrane and are therefore not viable, and cells in the upper right are considered as late apoptotic or necrotic.

Figure 28A:
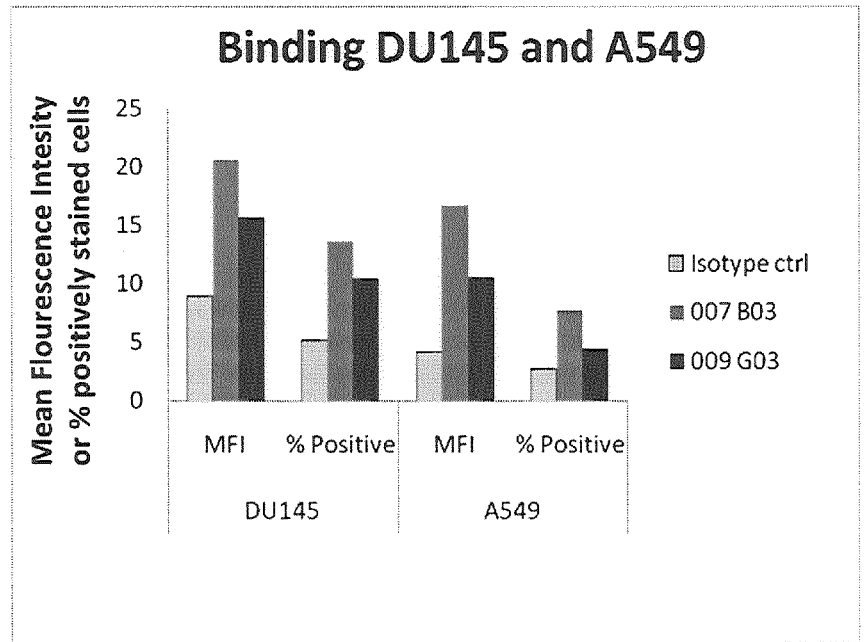
Figure 28B:
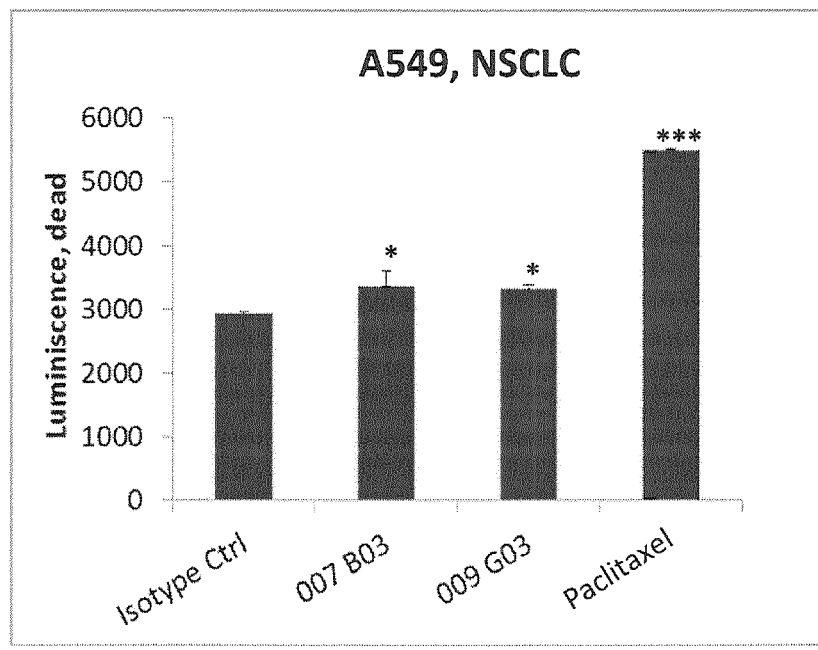

FIGS. 27A-27B. ROR1 specific antibodies mediate NK dependent ADCC in MM cell line The MM cell line RPMI-8226 was used as target cells and primary NK cells isolated from buffy coats as effector cells and used at an 1:40 ratio. Release of endogenous GADPH is used to measure lysis. FIGS. 28A and 28B shows data from triplicates±STD using NK cells from two different donors respectively.

Figure 28C:
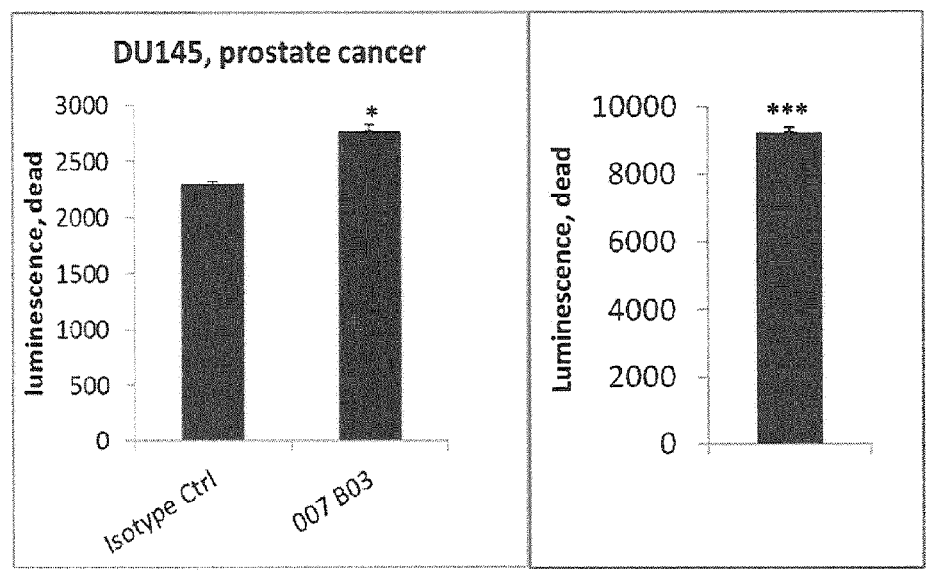
Figure 30A:
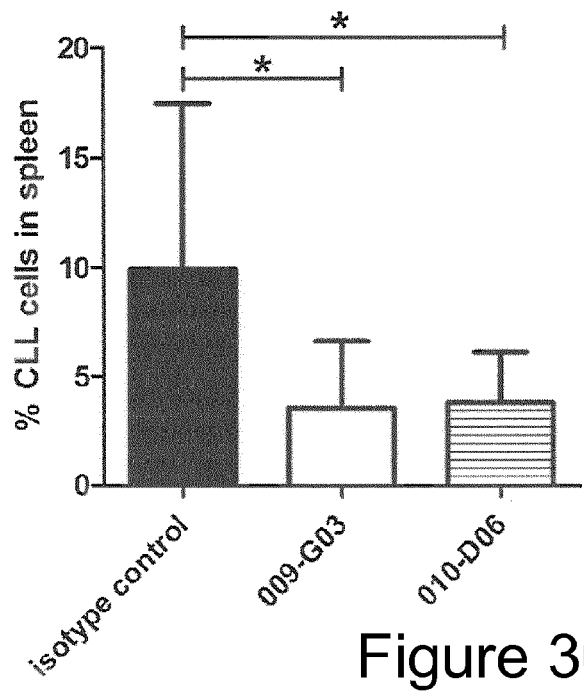
Figure 30B:
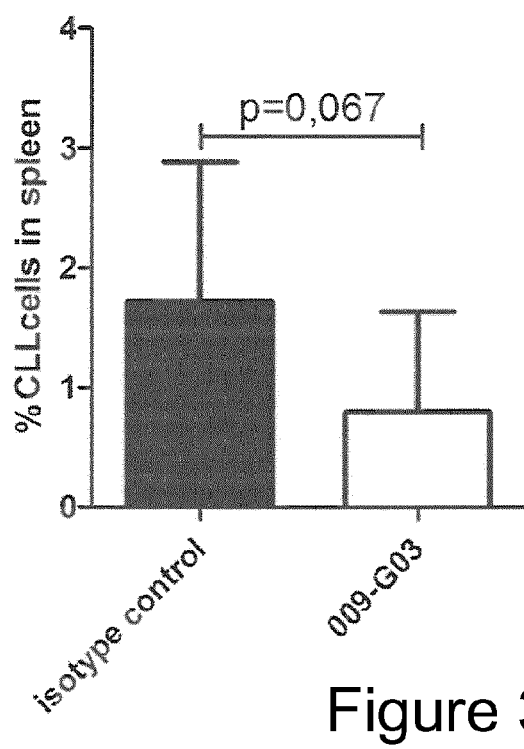
Figure 30C:
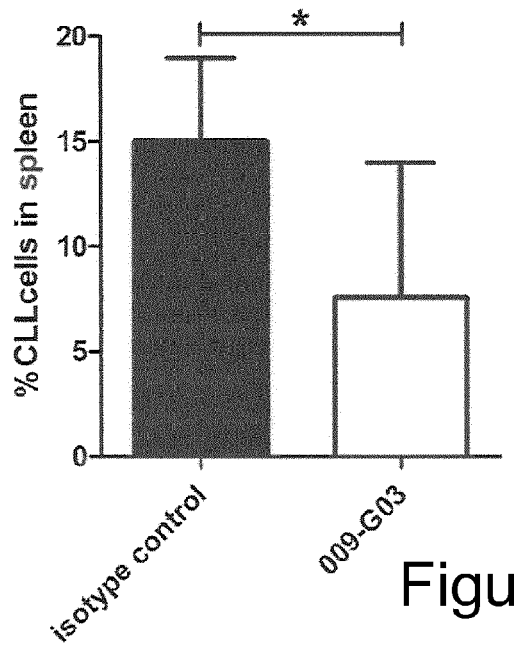
Figure 30D:
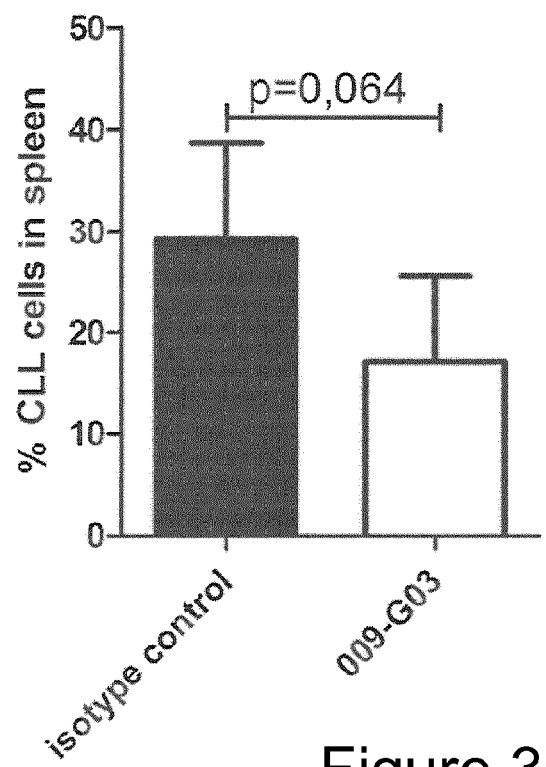

FIGS. 28A-28C. ROR1 specific antibodies bind A549 non-small cell lung cancer cells and DU145 prostate cancer cells and induce cell death.

FIG. 28A. The antibodies bind A549 (ATCC Nr: CCL-185) and DU145 (ATCC Nr: HTB-81) cells as measured by FACS. FIGS. 28B and 28C. Despite the rather weak binding, ROR1 specific antibodies induce significant cell death in the NSCLC and prostate cancer cell lines A549 and DU145 as measured by MultiTox-Glo Multiplex Cytotoxicity Assay suitable for adherent cells.

FIGS. 29A-29B. Affinity of 009-G03

Affinity (KD) of the 009-G03 antibody was determined to be 1.0 nM. Evaluation was done with a Scatchard plot of the $^{125}$I labelled ROR1 specific 009-G03 antibody binding to RPMI-8226. FIG. 29A shows the saturated curve and FIG. 29B shows the scatchard plot.

FIGS. 30A-30D. Primary patient CLL cells investigated in immunodeficient NOD.SCID mice.

Primary patient CLL cells are intravenously injected into immuno-deficient NOD. SCID mice. The CLL cells home to the spleen and there form proliferating clusters, very similar to human disease. After allowing to settle in the spleen for 5-7 days, the mice were treated with 10 mg/kg anti-ROR1 antibodies every third day and terminated after (A) 7 days, n=7 mice/group; (B) 7 days, n=9-10 mice/group; (C) 4 days, n=8 mice/group; (D) 3 days, n=5 mice/group. At termination the number of CLL cells is quantified in spleen using FACS staining of human CD45, CD19 and CD20. Each figure represents cells from individual CLL patients.

EXAMPLE 1

Generation of Ror1 Specific Antibodies

Isolation of scFv Antibody Fragments

The n-CoDeR® scFv library (BioInvent) was used to isolate scFv antibody fragments recognizing human ROR-1.

The phage library was used in a differential biopanning with CLL cells as target cells and an excess of B-cell depleted PBMC as competitor. After phage incubation, the cells were washed to remove unbound phages. Binding phages were eluted with trypsin and amplified in *E. coli*. Two consecutive biopannings were performed and the resulting phage stock was either converted to scFv format or used in a third panning against recombinant human ROR-1 before conversion to scFv. *E. coli* was transformed with scFv bearing plasmids and individual scFv clones were expressed.

Identification of Unique ROR-1 Binding scFv

Converted scFv from the third panning run against recombinant human ROR-1 were assayed for binding to coated hROR-1 with murine IgG3 Fc tag but not to coated murine IgG3.

0.3 pmole/well of hROR or mIgG3 was coated to an ELISA plate and incubated overnight at +4° C. After washing, scFv supernatant was left to bind the coated plate for 1 h. Bound scFv was detected using alkaline phosphatase conjugated mouse anti-FLAG antibody (Sigma) followed by CDP star substrate (Tropix). ROR binding scFv were sequenced to identify unique clones using standard sequencing techniques and all unique clones were analyzed for cell binding as described below. All cell binding scFv clones were converted to IgG format.

Converted scFv from the second panning against CLL cells were assayed for binding to CLL cells but not to B-cell depleted PBMC. CLL cells or PBMC were blocked with human IgG purified from human serum (IVIG, Sigma) 0.2 µg/ml for 10 min at +4° C. before addition of scFv supernatant for 1 h at +4° C.

After washing, scFv was detected using mouse anti-HIS (R&D Systems) followed by washing and detection with allophycocyanin conjugated anti-mouse F(ab)'2 antibody (Jackson Immunoresearch).

Finally, scFv binding was analyzed with flow cytometry. CLL binding scFv were sequenced to identify unique clones using standard sequencing techniques and all unique clones were analyzed for ROR binding in ELISA as described above.

IgG Binding to ROR-1 in ELISA

Converted IgG clones were analysed for ROR binding in ELISA. Recombinant human ROR-1 with murine IgG3 Fc tag was used as target and mIgG3 as non-target. ROR-1 or mIgG3 was coated at 1 pmole/well in ELISA plates overnight at +4° C. IgG was serially diluted in PBS+0.05% Tween and 0.45% Fish Gelatin (Sigma) from 50 µg/ml to 0.02 µg/ml (333 nM to 0.16 nM) or from 600 ng/ml to 0.3 ng/ml (4 nM to 0.002 nM) and added to the coated plate for 1 h at room temperature.

After washing with PBS+0.05% Tween, bound IgG was detected with horseradish peroxidase conjugated anti human antibody (Jackson Immunoresearch) diluted to 50 ng/ml in PBS+0.05% Tween and 0.45% Fish Gelatin.

Finally substrate; Supersingal pico (Pierce) was diluted 10 times in TRIS buffer, added to the washed plate and incubated for 10 min before luminescence reading using a plate reader (Tecan Ultra).

The antibodies were shown to bind to ROR1 protein but not to control protein as assayed by ELISA (see FIGS. 17A-17D)

IgG Binding to CLL Cells in Flow Cytometry

Converted IgG clones were analyzed for binding to CLL cells but not to B-cell depleted PBMC in flow cytometry. IgG was labeled with Alexa flour 647 conjugated Fab fragments, Zenon, according to the manufacturer's instructions (InVitrogen) and diluted to 10 µg/ml in PBS+0.5% BSA. CLL cells or PBMC were blocked with human IgG purified from human serum (IVIG, Sigma) 0.2 µg/ml for 10 min at +4° C. before incubation for 1 h at +4° C. with the labeled IgG.

Finally the cells were washed and IgG binding detected in flow cytometer (BD FACS Calibur).

EXAMPLE 2

ROR1 Specific mAb's Bind Primary CLL Cells but not PBMC Isolated from Healthy Volunteers CLL and PBMC Cell Isolation CLL cells were isolated from peripheral blood of human CLL patient volunteers. PBMCs were isolated from buffy coats derived from healthy volunteer blood samples.

Briefly, whole blood (CLL) or buffy coats (normal PBMC) were diluted 1:2 in PBS and were loaded onto Ficoll-Paque Plus (Amersham) cushions. Samples were centrifuged at 400×$g_{av}$ for 40 min at 20° C.

The upper, plasma-containing phase was removed and mononuclear cells were isolated from the distinct white band at the plasma/Ficoll interphase. Platelets were removed from the mononuclear cell suspension by washing with 4× volume of PBS, centrifugation at 60×$g_{av}$ for 10 min at 20° C., and complete aspiration of the supernatant.

FACS Analyses

Converted IgG clones were analysed for binding to CLL cells and PBMC's. IgG was labeled with Alexa flour 647 conjugated Fab fragments, Zenon, according to the manufacturer's instructions (InVitrogen) and diluted to 10 µg/ml in PBS+0.5% BSA. CLL cells and PBMC's were blocked with human IgG 0.2 µg/ml for 10 min at +4° C. before incubation for 1 h at +4° C. with the labeled IgG purified from human serum (IVIG, Sigma). Finally the cells were washed and IgG binding detected in flow cytometer (BD FACS Calibur).

The antibodies were shown to bind specifically to CLL cells but not to PBMC's cells obtained from peripheral blood of healthy volunteers as measured by FACS. (FIGS. 18 and 19)

EXAMPLE 3

Induction of CLL Cell Death by ROR1 mAb's

All the a-Ror-1 clones and the control antibody FITC-8GA was transiently expressed in HEK293 cells. All produced antibodies were analysed for endotoxin levels (<1 U/mL) and binding to respective antigen was confirmed by flow cytometer and ELISA. (FIGS. 17-19)

CLL Cell Isolation and Culture

CLL cells were isolated as described above and were then suspended in RPMI 1640 medium (Invitrogen) supplemented with 10% FBS and 1% penicillin/streptomycin.

CLL Cell Apoptosis Assay

CLL cells were seeded in 96-well culture plates at a density of $1\times10^6$ cells/mL culture medium (100.000 cells/well). 1 µg/mL of an a-ROR-1 antibody or of isotype control antibody (anti-FITC-8) were added to the cells, in the presence or absence of 3 µg/mL anti-human Fab $(ab')^2$ (Fcγ fragment specific, Jackson ImmunoResearch) for cross-linking. The cells were then incubated for 16 hours at 37° C. in a humidified atmosphere of 5% $CO_2$.

Flow Cytometry Analysis of Apoptosis Induction and ROR-1 Expression

The cells were harvested and stained for necrotic cells with the nuclei stain SYTOX green, and for apoptotic cells using Annexin V-647 (Invitrogen). Necrotic cells were identified by increased fluorescence in the FL-1 channel and apoptotic cells by increased signal in the FL-4 channel on a flow cytometer (FACSCalibur, BD Bioscience). (FIGS. 20 and 21)

EXAMPLE 5

In Vivo Effects of ROR1 mAb

PBMCs were isolated from peripheral blood of a one CLL patient using the Ficoll Hypaque technique. The cells were stained for CD19-PE and CD5-APC (BD) to enumerate CLL cells, which was found to be 89.6% of the PBMCs (data not shown). In comparison, only 1.1% were T cells.

Thereafter, $150\times10^6$ cells was injected i.p and i.v into NOD.SCID mice. The mice were treated i.p with 10 mg/kg of the ROR1 specific mAb 009-G03, or irrelevant negative control at day 1, and 4 after transfer. Mice were sacrificed day 7 and intra-peritoneal cells were collected using intra-peritoneal lavage of 8 ml PBS. Cells recovered from the peritoneum were stained for anti human CD45, anti CD3 (staining cells of human origin and human T cells respectively), anti CD19 and anti CD5 (staining CLL cells) (all antibodies from BD).

As compared with isotype control, the 009-G03 mA significantly reduces the number of grafted CLL cells. This shows that treatment with anti-Ror1 specifically depletes primary human CLL cells in a xenograft in vivo model. (FIG. 23)

EXAMPLE 6

ROR1 Specific Antibodies Bind and Kill RPMI 8226 Cells In Vitro, a Cell Line for Multiple Myeloma RPMI 8226 cells were obtained from ATCC and cultured according to instructions. For binding, IgG was labeled with Alexa flour 647 conjugated Fab fragments, Zenon, according to the manufacturer's instructions (InVitrogen) and diluted to 10 µg/ml in PBS+0.5% BSA. RPMI 8226 cells were blocked with human IgG 0.2 µg/ml for 10 min at +4° C. before incubation for 1 h at +4° C. with the labeled IgG. Finally the cells were washed and IgG binding detected in flow cytometer (BD FACS Calibur).

For cell death induction assays, RPMI 8226 cells were seeded in 96-well culture plates at a density of $1\times10^6$ cells/mL culture medium (100.000 cells/well). 10 or 1 µg/mL of an a-ROR-1 antibody or of isotype control antibody (anti-FITC-8) were added to the cells, in the presence or absence of 30 or 3 µg/ml of anti-human Fab $(ab)^2$(Fcγ fragment specific, Jackson ImmunoResearch) for cross-linking. The cells were then incubated for 16 hours at 37° C. in a humidified atmosphere of 5% $CO_2$. (FIGS. 24, 25 and 26)

EXAMPLE 7

ROR1 Specific Antibodies Bind A549 Non-Small Cell Lung Cancer Cells and DU145 Prostate Cancer Cells and Induce Cell Death In Vitro The cells were obtained from ATCC and cultured according to instructions. Cell lines A549 (ATCC Nr: CCL-185) and DU145 (ATCC Nr: HTB-81) were used. For binding, cells were dissociated using enzyme-free dissociation buffer and thereafter stained with Zenon labelled antibodies as described above.

For cell death assays, cells were seeded in 96-well culture plates at a density of $1.4\times10^5$ cells/mL culture medium (7000 cells/well). 10 µg/mL of an a-ROR-1 antibody or of an isotype control antibody (anti-FITC-8) were added to the cells, in the presence of 5M excess of anti-human Fab $(ab')^2$ (Fcγ fragment specific, Jackson ImmunoResearch) for cross-linking. Paclitaxel, a positive control for cell death was added at 5 µg/mL. The cells were then incubated for 24 and 48 hours at 37° C. in a humidified atmosphere of 5% $CO_2$.

The MultiTox-Glo Multiplex Cytotoxicity Assay (Promega) is a sequential-reagent-addition fluorescent and luminescent assay that measures the relative number of live and dead cells respectively in cell populations. The assay was performed as recommended by the manufacturer FIGS. 28A to 28C show the results of FACS analysis. FIG. 28A shows the antibodies bind A549 and DU145 cells (as measured by FACS). FIGS. 28B-28C show that despite the rather weak binding, ROR1 specific antibodies induce significant cell death in the NSCLC and prostate cancer cell lines A549 and DU145.

EXAMPLE 8

Identifying Competing Antibodies

Methods of identifying antibodies which compete against those created and tested above are as follows:

Method 1—FACS

To be performed preferably on primary CLL cells but if these are not available, RPMI 8226 cells might be used.

Labelled antibodies created above are added first (diluted to 20 µg/ml in FACS buffer) and allowed to bind to the cells by incubation for 20 min on ice, using a relevant isotype control antibody (typically IgG) as negative control. Wash the cells.

The antibody to be tested as to its competitive binding is added (and is labeled with a different color) and also allowed to incubate for 20 min on ice where after the cells are washed.

The signals are then quantified in a suitable FACS machine.

If the antibody to be tested binds to the same epitope, it's signal is significantly inhibited by the above created antibodies compared to the negative control.

In addition, this can be further tested by performing the reversed experiment by adding the competitors antibody prior to the above created antibodies and quantify the signals.

Method 2—ELISA

An ELISA plate is coated with ROR1 protein and incubated with the antibodies created above first (diluted to 20 µg/ml in suitable coating buffer). These are allowed to bind to the cells by incubation for 1 h in room temperature, using a relevant isotype control antibody (typically IgG) as negative control. Wash the plate.

Add antibody to be tested for competition, labeled with for example biotin or similar, and allow incubation for 1 h in room temperature where after the plates are washed. Add secondary detection and quantify the signals in a suitable ELISA reader.

If the antibody to be tested binds to the same epitope, it's signal is significantly inhibited by the above created antibodies compared to the negative control.

As with the FACs analysis this can be tested in the reverse experiment by adding in antibody to be tested before the above-created antibodies.

EXAMPLE 9

Affinity Determination and ADCC Testing

Affinity Determination

Antibody was labelled with $^{125}$I using free Iodine and test tubes pre-coated with the oxidant reagent Iodogen (1,3,4,6-tetrachloro-3α,6α-diphenylglycoluri, Thermo scientific), according to manufactures instruction. Briefly 200 μg of antibody was labeled for 10 minutes in PBS and free iodine were removed using a small disposable desalting columns (NAP 5, GE Healthcare Life science). Labeled antibody had a specific activity of approximately 2.5 μCi/μg antibody and contained less than 1% free Iodine as estimated with paper chromatography. $0.5 \times 10^6$ cells were incubated for 2.5 h on ice with different concentrations of $^{125}$I-labelled 009-G03 antibody. Free nonbinding antibody (F) was separated from cell bound antibody (B) by centrifugation through a 40% Ficoll-cushion and samples were analysed in a gamma counter (FIGS. 29A, 29B).

ADCC aCella-TOX Method

Cell line RPMI-8226 were evaluated in ADCC reactions with n-CoDeR-derived anti-ROR1 IgG1 antibodies, using the aCella-TOX kit (Cell Technology Inc).

The day before ADCC assay, effector NK cells were isolated from healthy human donor Buffy coats. Peripheral blood mononuclear cells were first extracted using Ficoll-Paque PLUS (GE Healthcare Life Sciences), followed by magnetic labeling and separation of NK cells according to standard protocol (Miltenyi Biotec). NK cells were kept in growth medium overnight at 4° C. Next day, target cells were collected, counted and prepared in 100 μl medium suspensions containing 250 000 cells. Anti-ROR1 antibodies, as well as isotype control were added to a final coating concentration of 5-10 μg/ml. After 1 h incubation on ice the cell suspensions were diluted in medium to 50 000 cells/ml. Subsequently, 100 μl from respective solution were dispensed per well in 96-well (V-shaped) tissue culture plates, yielding 5000 cells/well. Next, isolated NK cells were re-suspended in medium and added (100 μl/well) to the culture plates at an excess of 40:1 compared to the used target cells. The cell reactions were incubated 4 h at 37° C., followed by transfer of 100 μl/well of supernatant to flat-bottom, white reading plates. Finally, the level of released endogenous target cell GAPDH enzyme was assessed using the supplied aCella-TOX reagents, as a measurement of specific antibody-dependent NK cell-mediated cytotoxicity.

See FIGS. 27A-27B for results using ROR 009 G03, ROR 010 D06 and ROR 008 H06.

Calcein AM Method

Human effector NK cells were isolated a day before ADCC assay, as described above. Also, CLL cells were isolated with Ficoll-Paque PLUS on the same day and kept in DPBS+10% heat-inactivated FBS (reagents from Invitrogen) at 4° C. On the day of the ADCC experiment, CLL cells were collected, counted and loaded with 10 μM Calcein AM fluorescent dye (BD Biosciences) in medium. After thorough washing in medium, suspensions containing 100 000 cells were thereafter prepared and incubated with anti-ROR1 (and control) antibodies at 5 μg/ml for 30 min-1 h on ice. The samples were then diluted to 1 ml (in medium) and dispensed at 100 μl in tissue culture plates. Isolated NK cells were added as described above, and plates were incubated 4 h at 37° C. Subsequently, 100 μl/well of supernatant was transferred to black, flat-bottom reading plates. The samples were then read for spectrofluorescence at 485/535 nm (excitation/emission), where the signal intensity of released Calcein corresponds to antibody-dependent NK cell-mediated cytotoxicity (FIG. 22).

EXAMPLE 10

Further In Vivo Investigation of Patient Derived CLL Cells

NOD.SCID mice received whole-body irradiation of 1 Gy 1 day prior to injection of primary patient cells.

PBMCs were isolated from peripheral blood of four CLL patients using the Ficoll Hypaque technique. Thereafter, $100 \times 10^6$ cells was injected i.v into irradiated NOD.SCID mice. The mice were treated i.p with 10 mg/kg of the ROR1 specific mAb 009-G03, or irrelevant negative control mAb at day 5-7 after transfer of cells to mice and sacrificed 3-7 days later. Where the mice were sacrificed at 7 days after initial mAb administration, a second mAb injection was given 8-11 days after transfer.

Spleens were dissected out, minced, and lysed for red blood cells. The cell suspension were stained with fluorochrome conjugated mAb's recognizing human CD45, CD19 or CD20 and CLL cells were quantified as being either $CD45^+$ $CD19^+$ or $CD45^+CD20^+$. All such antibodies were purchased from BD Biosciences.

As compared with isotype control, the 009-G03 and 010-D06 mAb significantly reduces the number of grafted CLL cells in the spleen. It is believed that CLL cells residing in lymphoid organs are significantly more difficult to target compared to cells circulating in the blood and that this is one of the reasons for treatment failure in CLL patients. The applicant has shown that mAb's targeting ROR1 can significantly deplete primary human CLL cells in a highly relevant xenograft in vivo model (FIG. 30A to FIG. 30D).

EXAMPLE 11

Measurement of Internalisation Using FACS

Aliquot approximately 250 000 CLL cells/FACS sample, wash once in FACS buffer containing PBS and 2% FCS. Block unspecific Fc binding using 100 μl FACS buffer containing 100 μg/ml mouse γ-globulin, incubate for 10 minutes. Add saturating conditions of you're the ROR1 mAb under investigation, e.g. 10 μg/mL in media and incubate for either 30 min on ice (your reference value) or 37° C. for 2 h (value after 2 h of internalization). Wash twice with FACS buffer. Add secondary detection mAb diluted according to manufacturer's instruction. Incubate for 20 min on ice and thereafter wash twice with FACS buffer. Re-suspend cells in FACS buffer and analyse. Percent internalization is calculated as:

$$1 - \frac{\text{(Mean fluorescence intensity after 2 h in 37° C.)}}{\text{Mean fluorescence intensity after 30 min on ice}} \times 100$$

EXAMPLE 12

Preferred Pharmaceutical Formulations and Modes and Doses of Administration

The polypeptides, polynucleotides and antibodies of the present invention may be delivered using an injectable sustained-release drug delivery system. These are designed specifically to reduce the frequency of injections. An example of such a system is Nutropin Depot which encapsulates recombinant human growth hormone (rhGH) in biodegradable microspheres that, once injected, release rhGH slowly over a sustained period.

The polypeptides, polynucleotides and antibodies of the present invention can be administered by a surgically implanted device that releases the drug directly to the required site. For example, Vitrasert releases ganciclovir directly into the eye to treat CMV retinitis. The direct application of this toxic agent to the site of disease achieves effective therapy without the drug's significant systemic side-effects.

Electroporation therapy (EPT) systems can also be employed for administration. A device which delivers a pulsed electric field to cells increases the permeability of the cell membranes to the drug, resulting in a significant enhancement of intracellular drug delivery.

Polypeptides, polynucleotides and antibodies of the invention can also be delivered by electroincorporation (EI). EI occurs when small particles of up to 30 microns in diameter on the surface of the skin experience electrical pulses identical or similar to those used in electroporation. In EI, these particles are driven through the stratum corneum and into deeper layers of the skin. The particles can be loaded or coated with drugs or genes or can simply act as "bullets" that generate pores in the skin through which the drugs can enter.

An alternative method of administration is the ReGel injectable system that is thermosensitive. Below body temperature, ReGel is an injectable liquid while at body temperature it immediately forms a gel reservoir that slowly erodes and dissolves into known, safe, biodegradable polymers. The active drug is delivered over time as the biopolymers dissolve.

Polypeptides, polynucleotides and antibodies of the invention can be introduced to cells by "Trojan peptides". These are a class of polypeptides called penetratins which have translocating properties and are capable of carrying hydrophilic compounds across the plasma membrane. This system allows direct targeting of oligopeptides to the cytoplasm and nucleus, and may be non-cell type specific and highly efficient (Derossi et al., 1998, *Trends Cell Biol.*, 8, 84-87).

Preferably, the pharmaceutical formulation of the present invention is a unit dosage containing a daily dose or unit, daily sub-dose or an appropriate fraction thereof, of the active ingredient.

The polypeptides, polynucleotides and antibodies of the invention can be administered by any parenteral route, in the form of a pharmaceutical formulation comprising the active ingredient, optionally in the form of a non-toxic organic, or inorganic, acid, or base, addition salt, in a pharmaceutically acceptable dosage form. Depending upon the disorder and patient to be treated, as well as the route of administration, the compositions may be administered at varying doses.

In human therapy, the polypeptides, polynucleotides and antibodies of the invention can be administered alone but will generally be administered in admixture with a suitable pharmaceutical excipient diluent or carrier selected with regard to the intended route of administration and standard pharmaceutical practice.

The polypeptides, polynucleotides and antibodies of the invention can also be administered parenterally, for example, intravenously, intra-arterially, intraperitoneally, intra-thecally, intraventricularly, intrasternally, intracranially, intramuscularly or subcutaneously, or they may be administered by infusion techniques. They are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

Generally, in humans, oral or parenteral administration of the polypeptides, polynucleotides and antibodies of the invention is the preferred route, being the most convenient.

For veterinary use, the polypeptides, polynucleotides and antibodies of the invention are administered as a suitably acceptable formulation in accordance with normal veterinary practice and the veterinary surgeon will determine the dosing regimen and route of administration which will be most appropriate for a particular animal.

The formulations of the pharmaceutical compositions of the invention may conveniently be presented in unit dosage form and may be prepared by any of the methods well known in the art of pharmacy. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Preferred unit dosage formulations are those containing a daily dose or unit, daily sub-dose or an appropriate fraction thereof, of an active ingredient.

A preferred delivery system of the invention may comprise a hydrogel impregnated with a polypeptides, polynucleotides and antibodies of the invention, which is preferably carried on a tampon which can be inserted into the cervix and withdrawn once an appropriate cervical ripening or other desirable affect on the female reproductive system has been produced.

It should be understood that in addition to the ingredients particularly mentioned above the formulations of this invention may include other agents conventional in the art having regard to the type of formulation in question.

EXAMPLE 13

Exemplary Pharmaceutical Formulations

Whilst it is possible for polypeptides, polynucleotides and antibodies of the invention to be administered alone, it is preferable to present it as a pharmaceutical formulation, together with one or more acceptable carriers. The carrier(s) must be "acceptable" in the sense of being compatible with the compound of the invention and not deleterious to the recipients thereof. Typically, the carriers will be water or saline which will be sterile and pyrogen-free.

The following examples illustrate pharmaceutical formulations according to the invention in which the active ingredient is a polypeptides, polynucleotides and/or antibody of the invention.

EXAMPLE 13A

Injectable Formulation

| | |
|---|---|
| Active ingredient | 0.200 g |
| Sterile, pyrogen free phosphate buffer (pH 7.0) to | 10 ml |

The active ingredient is dissolved in most of the phosphate buffer (35-40° C.), then made up to volume and filtered through a sterile micropore filter into a sterile 10 ml amber glass vial (type 1) and sealed with sterile closures and overseals.

EXAMPLE 13B

Intramuscular Injection

| | |
|---|---|
| Active ingredient | 0.20 g |
| Benzyl Alcohol | 0.10 g |
| Glucofurol 75 ® | 1.45 g |
| Water for Injection q.s. to | 3.00 ml |

The active ingredient is dissolved in the glycofurol. The benzyl alcohol is then added and dissolved, and water added to 3 ml. The mixture is then filtered through a sterile micropore filter and sealed in sterile 3 ml glass vials (type 1).

The invention claimed is:

1. An anti-ROR1 antibody comprising a combination of all six CDR regions having the following amino acid sequences:
   (a) CDRH1, SEQ ID NO: 57; CDRH2, SEQ ID NO: 58; CDRH3, SEQ ID NO: 59, CDRL1, SEQ ID NO: 60; CDRL2, SEQ ID NO: 61; and CDRL3, SEQ ID NO: 62;
   (b) CDRH1, SEQ ID NO: 63; CDRH2, SEQ ID NO: 64; CDRH3, SEQ ID NO: 65, CDRL1, SEQ ID NO: 66; CDRL2, SEQ ID NO: 67; and CDRL3, SEQ ID NO: 68;
   (c) CDRH1, SEQ ID NO: 69; CDRH2, SEQ ID NO: 70; CDRH3, SEQ ID NO: 71, CDRL1, SEQ ID NO: 72; CDRL2, SEQ ID NO: 73; and CDRL3, SEQ ID NO: 74;
   (d) CDRH1, SEQ ID NO: 75; CDRH2, SEQ ID NO: 76; CDRH3, SEQ ID NO: 77, CDRL1, SEQ ID NO: 78; CDRL2, SEQ ID NO: 79; and CDRL3, SEQ ID NO: 80;
   (e) CDRH1, SEQ ID NO: 81; CDRH2, SEQ ID NO: 82; CDRH3, SEQ ID NO: 83, CDRL1, SEQ ID NO: 84; CDRL2, SEQ ID NO: 85; and CDRL3, SEQ ID NO: 86;
   (f) CDRH1, SEQ ID NO: 87; CDRH2, SEQ ID NO: 88; CDRH3, SEQ ID NO: 89, CDRL1, SEQ ID NO: 90; CDRL2, SEQ ID NO: 91; and CDRL3, SEQ ID NO: 92;
   (g) CDRH1, SEQ ID NO: 93; CDRH2, SEQ ID NO: 94; CDRH3, SEQ ID NO: 95, CDRL1, SEQ ID NO: 96; CDRL2, SEQ ID NO: 97; and CDRL3, SEQ ID NO: 98;
   (h) CDRH1, SEQ ID NO: 99; CDRH2, SEQ ID NO: 100; CDRH3, SEQ ID NO: 101, CDRL1, SEQ ID NO: 102; CDRL2, SEQ ID NO: 103; and CDRL3, SEQ ID NO: 104;
   (i) CDRH1, SEQ ID NO: 105; CDRH2, SEQ ID NO: 106; CDRH3, SEQ ID NO: 107, CDRL1, SEQ ID NO: 108; CDRL2, SEQ ID NO: 109; and CDRL3, SEQ ID NO: 110;
   (j) CDRH1, SEQ ID NO: 111; CDRH2, SEQ ID NO: 112; CDRH3, SEQ ID NO: 113, CDRL1, SEQ ID NO: 114; CDRL2, SEQ ID NO: 115; and CDRL3, SEQ ID NO: 116;
   (k) CDRH1, SEQ ID NO: 117; CDRH2, SEQ ID NO: 118; CDRH3, SEQ ID NO: 119, CDRL1, SEQ ID NO: 120; CDRL2, SEQ ID NO: 121; and CDRL3, SEQ ID NO: 122;
   (l) CDRH1, SEQ ID NO: 123; CDRH2, SEQ ID NO: 124; CDRH3, SEQ ID NO: 125, CDRL1, SEQ ID NO: 126; CDRL2, SEQ ID NO: 127; and CDRL3, SEQ ID NO: 128; or
   (m) CDRH1, SEQ ID NO: 129; CDRH2, SEQ ID NO: 130; CDRH3, SEQ ID NO: 131, CDRL1, SEQ ID NO: 132; CDRL2, SEQ ID NO: 133; and CDRL3, SEQ ID NO: 134.

2. An antibody as claimed in claim 1 comprising the combination of VH and VL region amino acid sequences of:
   SEQ ID NO: 5 and SEQ ID NO: 6,
   SEQ ID NO: 7 and SEQ ID NO: 8,
   SEQ ID NO: 9 and SEQ ID NO: 10,
   SEQ ID NO: 11 and SEQ ID NO: 12,
   SEQ ID NO: 13 and SEQ ID NO: 14,
   SEQ ID NO: 15 and SEQ ID NO: 16,
   SEQ ID NO: 17 and SEQ ID NO: 18,
   SEQ ID NO: 19 and SEQ ID NO: 20,
   SEQ ID NO: 21 and SEQ ID NO: 22,
   SEQ ID NO: 23 and SEQ ID NO: 24,
   SEQ ID NO: 25 and SEQ ID NO: 26,
   SEQ ID NO: 27 and SEQ ID NO: 28, or
   SEQ ID NO: 29 and SEQ ID NO: 30, respectively.

3. An antibody as claimed in any of claims 1 to 2 comprising the constant region CH, having the amino acid sequence of SEQ ID NO: 3 and the constant region CL having the amino acid sequence of SEQ ID NO: 4.

4. A pharmaceutical composition comprising an antibody as defined in claim 1 or 2 and a pharmaceutically acceptable excipient, diluent or carrier.

5. A kit of parts comprising:
   (i) an antibody as claimed in claim 1 or 2;
   (ii) apparatus for administering the antibody; and
   (iii) instructions for use.

6. A kit of parts comprising:
   (i) a pharmaceutical composition as claimed in claim 4;
   (ii) apparatus for administering the pharmaceutical composition; and
   (iii) instructions for use.

* * * * *

```
SEQUENCE LISTING

<160> NUMBER OF SEQ ID NOS: 134

<210> SEQ ID NO 1
<211> LENGTH: 15
<212> TYPE: PRT
<213> ORGANISM: Mus musculus

<400> SEQUENCE: 1

Trp Asn Ile Ser Ser Glu Leu Asn Lys Asp Ser Tyr Leu Thr Leu
1               5                   10                  15

<210> SEQ ID NO 2
<211> LENGTH: 15
<212> TYPE: PRT
<213> ORGANISM: Mus musculus

<400> SEQUENCE: 2

Asn Lys Ser Gln Lys Pro Tyr Lys Ile Asp Ser Lys Gln Ala Ser
1               5                   10                  15

<210> SEQ ID NO 3
<211> LENGTH: 330
<212> TYPE: PRT
<213> ORGANISM: Mus musculus

<400> SEQUENCE: 3

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80
```

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 4
<211> LENGTH: 105
<212> TYPE: PRT
<213> ORGANISM: Mus musculus

<400> SEQUENCE: 4

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Thr Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
            100                 105

<210> SEQ ID NO 5

```
<211> LENGTH: 118
<212> TYPE: PRT
<213> ORGANISM: Mus musculus

<400> SEQUENCE: 5

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met His Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gln Gly Arg Ala Val Thr Leu Asp Tyr Trp Gly Gln Gly Thr
            100                 105                 110

Leu Val Thr Val Ser Ser
        115

<210> SEQ ID NO 6
<211> LENGTH: 110
<212> TYPE: PRT
<213> ORGANISM: Mus musculus

<400> SEQUENCE: 6

Gln Ser Val Leu Thr Gln Pro Pro Ser Ala Ser Gly Thr Pro Gly Gln
1               5                   10                  15

Arg Val Thr Ile Ser Cys Ser Gly Ser Arg Ser Asn Ile Gly Ser Asn
            20                  25                  30

Ser Val His Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ser Ser Tyr Thr Ser Ser Ser
                85                  90                  95

Thr Leu Leu Phe Gly Gly Gly Thr Lys Leu Thr Val Leu Gly
            100                 105                 110

<210> SEQ ID NO 7
<211> LENGTH: 123
<212> TYPE: PRT
<213> ORGANISM: Mus musculus

<400> SEQUENCE: 7

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ala Trp Val Arg Gln Ala Pro Gly Lys Gly Leu Glu Trp Val
        35                  40                  45

Ser Gly Val Ser Trp Asn Gly Ser Arg Thr His Tyr Ala Asp Ser Val
    50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Gln Asp Leu Ser Gly Trp Tyr Pro Gly Tyr Phe Asp Tyr
            100                 105                 110

Trp Gly Gln Gly Thr Leu Val Thr Val Ser Ser
            115                 120
```

<210> SEQ ID NO 8
<211> LENGTH: 110
<212> TYPE: PRT
<213> ORGANISM: Mus musculus

<400> SEQUENCE: 8

```
Gln Ser Val Leu Thr Gln Pro Pro Ser Ala Ser Gly Thr Pro Gly Gln
  1               5                  10                  15

Arg Val Thr Ile Ser Cys Ser Gly Ser Ser Ser Asp Met Gly Asn Tyr
                 20                  25                  30

Ala Val Ser Trp Tyr Gln Gln Leu Pro Gly Thr Ala Pro Lys Leu Leu
             35                  40                  45

Ile Tyr Gly Asn Ser Asn Arg Pro Ser Gly Val Pro Asp Arg Phe Ser
 50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Ser Ser Tyr Thr Ser Ser Arg
                 85                  90                  95

Thr Val Val Phe Gly Gly Gly Thr Lys Leu Thr Val Leu Gly
            100                 105                 110
```

<210> SEQ ID NO 9
<211> LENGTH: 117
<212> TYPE: PRT
<213> ORGANISM: Mus musculus

<400> SEQUENCE: 9

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
                 20                  25                  30

Ala Met Ser Trp Val Arg Gln Ala Pro Gly Lys Gly Leu Glu Trp Val
             35                  40                  45

Ser Ala Ile Gly Ala Gly Gly Gly Thr Tyr Tyr Ala Asp Ser Val Lys
 50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Ser Gly Gly Ser Trp Glu Leu Pro Asp Tyr Trp Gly Gln Gly Thr Leu
            100                 105                 110

Val Thr Val Ser Ser
            115
```

<210> SEQ ID NO 10
<211> LENGTH: 111
<212> TYPE: PRT
<213> ORGANISM: Mus musculus -continued

```
<400> SEQUENCE: 10

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
            35                  40                  45

Ile Tyr Tyr Asp Asp Leu Leu Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ser Ser His Thr Thr Thr Ser
                85                  90                  95

Thr Phe Trp Val Phe Gly Gly Gly Thr Lys Leu Thr Val Leu Gly
            100                 105                 110

<210> SEQ ID NO 11
<211> LENGTH: 115
<212> TYPE: PRT
<213> ORGANISM: Mus musculus

<400> SEQUENCE: 11

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30

Ser Met Asn Trp Val Arg Gln Ala Pro Gly Lys Gly Leu Glu Trp Val
            35                  40                  45

Ser Ser Ile Ser Ser Ser Ser Thr Ile Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Lys Thr Leu Ala Leu Asp Ile Trp Gly Gln Gly Thr Leu Val Thr
            100                 105                 110

Val Ser Ser
        115

<210> SEQ ID NO 12
<211> LENGTH: 112
<212> TYPE: PRT
<213> ORGANISM: Mus musculus

<400> SEQUENCE: 12

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ala Arg
            20                  25                  30

Tyr Asp Val His Trp Tyr Gln Gln Leu Pro Gly Thr Ala Pro Lys Leu
            35                  40                  45

Leu Ile Tyr Ser Asp Asp Gln Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Gln Ser Tyr Asp Ser Ser
```

```
                    85                  90                  95

Leu Ser Gly Trp Val Phe Gly Gly Gly Thr Lys Leu Thr Val Leu Gly
                100                 105                 110

<210> SEQ ID NO 13
<211> LENGTH: 119
<212> TYPE: PRT
<213> ORGANISM: Mus musculus

<400> SEQUENCE: 13

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Ser Gly Ile Thr Gly Ser Gly Asp Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Gly Gly Asp Thr Ser Gly Tyr Gly Pro His Trp Gln Gly
                100                 105                 110

Thr Leu Val Thr Val Ser Ser
        115

<210> SEQ ID NO 14
<211> LENGTH: 111
<212> TYPE: PRT
<213> ORGANISM: Mus musculus

<400> SEQUENCE: 14

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Tyr Val Tyr Trp Tyr Gln Gln Leu Pro Gly Thr Ala Pro Lys Leu Leu
        35                  40                  45

Ile Tyr Asp Asn Asn Lys Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gln Ser Tyr Asp Asp Thr Leu
                85                  90                  95

Ser Val Val Val Phe Gly Gly Gly Thr Lys Leu Thr Val Leu Gly
                100                 105                 110

<210> SEQ ID NO 15
<211> LENGTH: 130
<212> TYPE: PRT
<213> ORGANISM: Mus musculus

<400> SEQUENCE: 15

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30
```

Tyr Met Ser Trp Ile Arg Gln Ala Pro Gly Lys Gly Leu Glu Trp Val
            35                  40                  45

Ala Ile Ile Ser Tyr Asp Gly Ser Asn Glu Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Thr Ser Ser Gly Asp Gly Gly Trp Glu Asp Trp Gly Pro Pro Tyr
             100                 105                 110

Tyr Tyr Tyr Gly Met Asp Val Trp Gly Gln Gly Thr Leu Val Thr Val
            115                 120                 125

Ser Ser
130

<210> SEQ ID NO 16
<211> LENGTH: 112
<212> TYPE: PRT
<213> ORGANISM: Mus musculus

<400> SEQUENCE: 16

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Leu Gly Ala Gly
             20                  25                  30

Tyr Ala Val His Trp Tyr Gln Gln Leu Pro Gly Thr Ala Pro Lys Leu
            35                  40                  45

Leu Ile Tyr Gly Asn Thr Asn Arg Pro Ser Gly Val Pro Asp Arg Phe
 50                  55                  60

Ser Gly Ser Lys Ser Gly Thr Ser Ala Ser Leu Ala Ile Ser Gly Leu
 65                  70                  75                  80

Arg Ser Glu Asp Glu Ala Asp Tyr Tyr Cys Ala Ala Trp Asp Asp Ser
                 85                  90                  95

Leu Arg Gly Pro Val Phe Gly Gly Gly Thr Lys Leu Thr Val Leu Gly
            100                 105                 110

<210> SEQ ID NO 17
<211> LENGTH: 121
<212> TYPE: PRT
<213> ORGANISM: Mus musculus

<400> SEQUENCE: 17

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
            35                  40                  45

Ser Val Ile Tyr Ser Gly Gly Ser Thr Tyr Tyr Ala Asp Ser Val Lys
 50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Arg Asp Ser Trp Glu Leu Leu Gly Tyr Asp Ala Phe Asp Leu Trp Gly
            100                 105                 110

Gln Gly Thr Leu Val Thr Val Ser Ser
        115                 120

<210> SEQ ID NO 18
<211> LENGTH: 111
<212> TYPE: PRT
<213> ORGANISM: Mus musculus

<400> SEQUENCE: 18

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Tyr Val Tyr Trp Tyr Gln Gln Leu Pro Gly Thr Ala Pro Lys Leu Leu
        35                  40                  45

Ile Tyr Gly Asp Ser Asn Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Thr Trp Asp Ser Ser Leu
                85                  90                  95

Ser Ala Trp Val Phe Gly Gly Gly Thr Lys Leu Thr Val Leu Gly
            100                 105                 110

<210> SEQ ID NO 19
<211> LENGTH: 122
<212> TYPE: PRT
<213> ORGANISM: Mus musculus

<400> SEQUENCE: 19

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn His
            20                  25                  30

Glu Met Asn Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Glu Tyr Thr Ile Leu Gly Ala Tyr Tyr Phe Asp Phe Trp
            100                 105                 110

Gly Gln Gly Thr Leu Val Thr Val Ser Ser
        115                 120

<210> SEQ ID NO 20
<211> LENGTH: 112
<212> TYPE: PRT
<213> ORGANISM: Mus musculus

<400> SEQUENCE: 20

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Glu Ser Ser
            20                  25                  30

-continued

```
Thr Val Asn Trp Tyr Gln Gln Leu Pro Gly Thr Ala Pro Lys Leu Leu
             35                  40                  45

Ile Tyr Asp Asn Asn Lys Arg Pro Ser Gly Val Pro Asp Arg Phe Ser
 50                      55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Gln Ser Tyr Asp Ser Ser Leu
                 85                  90                  95

Ser Pro Leu Val Leu Phe Gly Gly Gly Thr Lys Leu Thr Val Leu Gly
             100                 105                 110
```

<210> SEQ ID NO 21
<211> LENGTH: 119
<212> TYPE: PRT
<213> ORGANISM: Mus musculus

<400> SEQUENCE: 21

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Asp Tyr
             20                  25                  30

Tyr Met Ser Trp Ile Arg Gln Ala Pro Gly Lys Gly Leu Glu Trp Val
             35                  40                  45

Ser Ala Ile Ser Gly Ser Gly Gly Ser Thr Tyr Tyr Ala Asp Ser Val
 50                      55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Glu Asp Trp Glu Gly Ala Ser Phe Asp Tyr Trp Gly Gln Gly
             100                 105                 110

Thr Leu Val Thr Val Ser Ser
         115
```

<210> SEQ ID NO 22
<211> LENGTH: 111
<212> TYPE: PRT
<213> ORGANISM: Mus musculus

<400> SEQUENCE: 22

```
Gln Ser Val Leu Thr Gln Pro Pro Ser Ala Ser Gly Thr Pro Gly Gln
 1               5                  10                  15

Arg Val Thr Ile Ser Cys Ser Gly Ser Ser Asn Ile Gly Ile Asn
             20                  25                  30

Thr Val Asn Trp Tyr Gln Gln Leu Pro Gly Thr Ala Pro Lys Leu Leu
             35                  40                  45

Ile Tyr Asp Asn Asn Lys Arg Pro Ser Gly Val Pro Asp Arg Phe Ser
 50                      55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Ala Thr Trp Asp Asp Ser Leu
                 85                  90                  95

Ser Gly Trp Val Phe Gly Gly Gly Thr Lys Leu Thr Val Leu Gly
             100                 105                 110
```

<210> SEQ ID NO 23
<211> LENGTH: 116

```
<212> TYPE: PRT
<213> ORGANISM: Mus musculus

<400> SEQUENCE: 23

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Gly Thr Thr Phe Asp Tyr Trp Gly Gln Gly Thr Leu Val
            100                 105                 110

Thr Val Ser Ser
            115

<210> SEQ ID NO 24
<211> LENGTH: 112
<212> TYPE: PRT
<213> ORGANISM: Mus musculus

<400> SEQUENCE: 24

Gln Ser Val Leu Thr Gln Pro Pro Ser Ala Ser Gly Thr Pro Gly Gln
 1               5                  10                  15

Arg Val Thr Leu Ser Cys Thr Gly Ser Asn Ser Asn Leu Gly Ala Pro
            20                  25                  30

Tyr Asp Val His Trp Tyr Gln Gln Leu Pro Gly Thr Ala Pro Lys Leu
        35                  40                  45

Leu Ile Tyr Ser Asp Asn Gln Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Gly Thr Trp Asp Ser
                85                  90                  95

Leu Ser Gly Trp Val Phe Gly Gly Gly Thr Lys Leu Thr Val Leu Gly
            100                 105                 110

<210> SEQ ID NO 25
<211> LENGTH: 115
<212> TYPE: PRT
<213> ORGANISM: Mus musculus

<400> SEQUENCE: 25

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Gly Val Ser Trp Asn Gly Ser Arg Thr His Tyr Ala Asp Ser Val
    50                  55                  60

Lys Gly Arg Phe Thr Ile Ser Arg Asp Asn Ser Lys Asn Thr Leu Tyr
```

```
                65                  70                  75                  80
Leu Gln Met Asn Ser Leu Arg Ala Glu Asp Thr Ala Val Tyr Tyr Cys
                        85                  90                  95

Ala Ser Asn Ala Pro Phe Asp Pro Trp Gly Gln Gly Thr Leu Val Thr
                100                 105                 110

Val Ser Ser
        115

<210> SEQ ID NO 26
<211> LENGTH: 111
<212> TYPE: PRT
<213> ORGANISM: Mus musculus

<400> SEQUENCE: 26

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
                20                  25                  30

Tyr Val Tyr Trp Tyr Gln Gln Leu Pro Gly Thr Ala Pro Lys Leu Leu
                35                  40                  45

Ile Tyr Asp Asn Asn Lys Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gln Ser Tyr Asp Ser Ser Leu
                        85                  90                  95

Ser Ala Val Val Phe Gly Gly Gly Thr Lys Leu Thr Val Leu Gly
                100                 105                 110

<210> SEQ ID NO 27
<211> LENGTH: 121
<212> TYPE: PRT
<213> ORGANISM: Mus musculus

<400> SEQUENCE: 27

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Asp Tyr
                20                  25                  30

Gly Met His Trp Val Arg Gln Ala Pro Gly Lys Gly Leu Glu Trp Val
                35                  40                  45

Ser Ala Ile Ser Gly Ser Gly Gly Ser Thr Phe Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                        85                  90                  95

Ala Arg Gly Arg Ser Ala Gly Ser Met Gly Tyr Phe Asp Tyr Trp Gly
                100                 105                 110

Gln Gly Thr Leu Val Thr Val Ser Ser
        115                 120

<210> SEQ ID NO 28
<211> LENGTH: 112
<212> TYPE: PRT
<213> ORGANISM: Mus musculus

<400> SEQUENCE: 28
```

Gln Ser Val Leu Thr Gln Pro Pro Ser Ala Ser Gly Thr Pro Gly Gln
1               5                   10                  15

Arg Val Thr Ile Ser Cys Thr Gly Ser Ser Asn Ile Gly Ala Gly
            20                  25                  30

Tyr Asp Val His Trp Tyr Gln Gln Leu Pro Gly Thr Ala Pro Lys Leu
            35                  40                  45

Leu Ile Tyr Gly Asn Ser Asn Arg Pro Ser Gly Val Pro Asp Arg Phe
50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Asp Ser
                85                  90                  95

Leu Asn Gly Trp Val Phe Gly Gly Gly Thr Lys Leu Thr Val Leu Gly
            100                 105                 110

<210> SEQ ID NO 29
<211> LENGTH: 121
<212> TYPE: PRT
<213> ORGANISM: Mus musculus

<400> SEQUENCE: 29

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
            35                  40                  45

Ala Ile Ile Ser Tyr Asp Gly Asn Glu Asn Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Asp Ile Asp Tyr Ala Asp Asp Ala Tyr Asp Ile Trp Gly
            100                 105                 110

Gln Gly Thr Leu Val Thr Val Ser Ser
        115                 120

<210> SEQ ID NO 30
<211> LENGTH: 112
<212> TYPE: PRT
<213> ORGANISM: Mus musculus

<400> SEQUENCE: 30

Gln Ser Val Leu Thr Gln Pro Pro Ser Ala Ser Gly Thr Pro Gly Gln
1               5                   10                  15

Arg Val Thr Ile Ser Cys Thr Gly Ser Ser Asn Ile Gly Ala Gly
            20                  25                  30

Tyr Asp Val Leu Trp Tyr Gln Gln Leu Ser Gly Thr Ala Pro Lys Leu
            35                  40                  45

Leu Ile Tyr Ser Asn Asn Gln Arg Pro Ser Gly Val Pro Asp Arg Phe
50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ser Trp Asp Asp Ser
                85                  90                  95

Leu Ser Gly Pro Val Phe Gly Gly Gly Thr Lys Leu Thr Val Leu Gly
        100                 105                 110

<210> SEQ ID NO 31
<211> LENGTH: 353
<212> TYPE: DNA
<213> ORGANISM: Mus musculus

<400> SEQUENCE: 31
gaggtgcagc tgttggagtc tgggggaggc ttggtacagc ctggggggtc cctgagactc      60
tcctgtgcag cctctggatt caccttcagt aactactgga tgcactgggt ccgccaagct     120
ccagggaagg ggctggagtg gtctcagct attagtggta gtggtggtag cacatactac      180
gcagactccg tgaagggccg gttcaccatc tccagagaca khccaagaac acgctgtatc     240
tgcaaatgaa cagccrgaga gccgaggaca ctgccgtgta tactgtgcg agacagggac      300
gtgcagttac ccttgactac tggggccagg gtacactggt caccgtgagc tca            353

<210> SEQ ID NO 32
<211> LENGTH: 330
<212> TYPE: DNA
<213> ORGANISM: Mus musculus

<400> SEQUENCE: 32
cagtctgtgc tgacrcagcc accctcagcg tctgggaccc ccgggcagag ggtcaccatc      60
tcttgttctg gaagcaggtc caacatcggg agtaactccg tacactggta tcagcagctc     120
ccaggaacgg cccccaaact cctcatctat agtaataatc agcggccctc aggggtccct     180
gaccgattct ctggctccaa gtctggcacc tcagcctccc tggccatcag tgggctccgg     240
tccgaggatg aggctgatta ttactgcagc tcatatacaa gcagcagcac tctgctattc     300
ggcggaggaa ccaagctgac ggtcctaggt                                      330

<210> SEQ ID NO 33
<211> LENGTH: 369
<212> TYPE: DNA
<213> ORGANISM: Mus musculus

<400> SEQUENCE: 33
gaggtgcagc tgttggagtc tgggggaggc ttggtacagc ctggggggtc cctgagactc      60
tcctgtgcag cctctggatt caccttagc agctatgaca tggcctgggt ccgccaggct     120
ccagggaagg ggctggagtg gtatcgggt gttagttgga atggcagtag dacgcactat     180
gcagactctg tgaagggccg attcaccatc tccagagaca attccaagaa cacgctgtat     240
ctgcaaatga acagcctgag agccgaggac actgccgtgt attactgtgc gagagatcaa     300
gatctcagtg gctggtaccc ggggtacttt gactactggg gccagggtac actggtcacc     360
gtgagctca                                                             369

<210> SEQ ID NO 34
<211> LENGTH: 330
<212> TYPE: DNA
<213> ORGANISM: Mus musculus

<400> SEQUENCE: 34
cagtctgtgc tgactcagcc accctcagcg tctgggaccc ccgggcagag ggtcaccatc      60
tcctgctctg gaagcagctc cgacatgggg aattatgcgg tatcctggta tcagcagctc     120
ccaggaacgg cccccaaact cctcatctat ggtaacagca atcggccctc agggtccct     180

```
gaccgattct ctggctccaa gtctggcacc tcagcctccc tggccatcag tgggctccgg      240
tccgaggatg aggctgatta ttactgcagc tcatatacaa gcagtcgcac tgtggtgttc      300
ggcggaggaa ccaagctgac ggtcctaggt                                      330
```

<210> SEQ ID NO 35
<211> LENGTH: 351
<212> TYPE: DNA
<213> ORGANISM: Mus musculus

<400> SEQUENCE: 35

```
gaggtgcagc tgttggagtc tgggggaggc ttggtacagc ctgggggtc cctgagactc       60 tcctgtgcag cctctggatt caccttagc agctatgcca tgagctgggt ccgccaggct      120
ccagggaagg gctggagtg gtatcagct attggtgctg gtggtggcac atactatgca      180
gactccgtga agggccgatt caccatctcc agagacaatt ccaagaacac gctgtatctg      240
caaatgaaca gcctgagagc cgaggacact gccgtgtatt actgtgcgag tggcggatcg      300
tgggagctac ctgactactg gggccagggt acactggtca ccgtgagctc a              351
```

<210> SEQ ID NO 36
<211> LENGTH: 333
<212> TYPE: DNA
<213> ORGANISM: Mus musculus

<400> SEQUENCE: 36

```
cagtctgtgc tgactcagcc accctcagcg tctgggaccc ccgggcagag ggtcaccatc       60
tcttgttctg gaagcagctc caacatcgga agtaatactg taaactggta tcagcagctc      120
ccaggaacgg cccccaaact cctcatctat tatgatgatc tgctgccctc agggtgtcct      180
gaccgattct ctggctccaa gtctggcacc tcagcctccc tggccatcag tgggctccgg      240
tccgaggatg aggctgatta ttactgcagc tcacatacaa ccaccagcac tttttgggtg      300
ttcggcggag gaaccaagct gacggtccta ggt                                  333
```

<210> SEQ ID NO 37
<211> LENGTH: 346
<212> TYPE: DNA
<213> ORGANISM: Mus musculus

<400> SEQUENCE: 37

```
gaggtgcagc tgttggagtc tgggggaggc ttggtacagc ctgggggtc cctgagactc       60 tcctgtgcag cctctggatt cacctttagt ccttatagca tgattctggg tccgccaggc      120
tccagggaag gggctggagt gggtctcatc cattagtagt agtagtacca tatactacgc      180
agactctgtg aagggccgat tcaccatctc cagagacaat tccaagaaca cgctgtatct      240
gcaaatgaac agcctgagag ccgaggacac tgccgtgtat tactgtgcga gaaaaacctt      300
ggctcttgat atctggggcc aaggtacact ggtcaccgtg agctca                    346
```

<210> SEQ ID NO 38
<211> LENGTH: 336
<212> TYPE: DNA
<213> ORGANISM: Mus musculus

<400> SEQUENCE: 38

```
cagtctgtgc tgactcagcc accctcagcg tctgggaccc ccgggcagag ggtcaccatc       60
tcctgcactg ggagcagctc caacatcggg gcacgttatg atgttcactg gtatcagcag      120
```

```
ctcccaggaa cggcccccaa actcctcatc tatagtgatg atcagcggcc ctcaggggtc      180
cctgaccgat tctctggctc caagtctggc acctcagcct ccctggccat cagtgggctc      240
cggtccgagg atgaggctga ttattactgc cagtcctacg acagcagcct gagtggttgg      300
gtgttcggcg gaggaaccaa gctgacggtc ctaggt                                336

<210> SEQ ID NO 39
<211> LENGTH: 357
<212> TYPE: DNA
<213> ORGANISM: Mus musculus

<400> SEQUENCE: 39
gaggtgcagc tgttggagtc tgggggaggc ttggtacagc ctggggggtc cctgagactc       60
tcctgtgcag cctctggatt caccttcagt aacgcctgga tgagctgggt ccgccaggct      120
ccagggaagg ggctggagtg ggtctcaggt attactggta gtggtgatag cacatactac      180
gcagactccg tgaagggccg cttcaccatc tccagagaca attccaagaa cacgctgtat      240
ctgcaaatga acagcctgag agccgaggac actgccgtgt attactgtgc gacggggga      300 gatactagtg ggtatggacc ccactggggc caaggtacac tggtcaccgt gagctca        357

<210> SEQ ID NO 40
<211> LENGTH: 333
<212> TYPE: DNA
<213> ORGANISM: Mus musculus

<400> SEQUENCE: 40
cagtctgtgc tgactcagcc accctcagcg tctgggaccc ccgggcagag ggtcaccatc       60
tcctgttctg gaagcagctc caacatcgga agtaattatg tatactggta tcagcagctc      120
ccaggaacgg ccccccaaact cctcatctat gacaataata agcgaccctc aggggtccct      180
gaccgattct ctggctccaa gtctggcacc tcagcctccc tggccatcag tgggctccgg      240
tccgaggatg aggctgatta ttactgtcaa tcctacgacg acaccctgag tgttgtggtg      300
ttcggcggag gaaccaagct gacggtccta ggt                                   333

<210> SEQ ID NO 41
<211> LENGTH: 390
<212> TYPE: DNA
<213> ORGANISM: Mus musculus

<400> SEQUENCE: 41
gaggtgcagc tgttggagtc tgggggaggc ttggtacagc ctggggggtc cctgagactc       60
tcctgtgcag cctctggatt caccttcagt gactactaca tgagctggat ccgccaggct      120
ccagggaagg ggctggagtg ggtggcaatt atatcatatg atggaagtaa tgaatactat      180
gcagactccg tgaagggccg attcaccatc tccagagaca attccaagaa cacgctgtat      240
ctgcaaatga acagcctgag agccgaggac actgccgtgt attactgtgc aacatcctcg      300
ggggatgggg gatgggagga ttggggccca ccttactact actacggtat ggacgtctgg      360
ggccagggta cactggtcac cgtgagctca                                       390

<210> SEQ ID NO 42
<211> LENGTH: 336
<212> TYPE: DNA
<213> ORGANISM: Mus musculus

<400> SEQUENCE: 42
cagtctgtgc tgactcagcc accctcagcg tctgggaccc ccgggcagag ggtcaccatc       60
```

```
tcctgcactg ggagcagctc caacctcggg gcaggttatg ctgtacactg gtatcagcag      120
ctcccaggaa cggcccccaa actcctcatc tatggtaaca ccaatcggcc ctcagggg tc     180 cctgaccgat tctctggctc caagtctggc acctcagcct ccctggccat cagtgggctc     240
cggtccgagg atgaggctga ttattactgt gcggcatggg atgacagcct gagaggtccg     300
gtgttcggcg gaggaaccaa gctgacggtc ctaggt                               336
```

<210> SEQ ID NO 43
<211> LENGTH: 363
<212> TYPE: DNA
<213> ORGANISM: Mus musculus

<400> SEQUENCE: 43

```
gaggtgcagc tgttggagtc tgggggaggc ttggtacagc ctggggggtc cctgagactc      60
tcctgtgcag cctctggatt cacctttagc agctatgcca tgagctgggt ccgccaggct     120
cctgggaagg ggctggagtg ggtctcagtt atttatagcg gtggtagcac atactacgca     180
gactccgtga agggccgatt caccatctcc agagacaatt ccaagaacac gctgtatctg     240
caaatgaaca gcctgagagc cgaggacact gccgtgtatt actgtgcgag ggattcttgg     300
gagctaatag gtatgatgc ttttgatctc tggggccaag gtacactggt caccgtgagc     360
tca                                                                    363
```

<210> SEQ ID NO 44
<211> LENGTH: 333
<212> TYPE: DNA
<213> ORGANISM: Mus musculus

<400> SEQUENCE: 44

```
cagtctgtgc tgactcagcc accctcagcg tctgggaccc ccgggcagag ggtcaccatc      60
tcttgttctg gaagcagctc caacatcgga agtaattatg tatactggta tcagcagctc     120
ccaggaacgg cccccaaact cctcatctat ggtgacagta atcggccctc aggggtccct     180
gaccgattct ctggctccaa gtctggcacc tcagcctccc tggccatcag tgggctccgg     240
tccgaggatg aggctgatta ttactgcgga acatgggata gcagcctgag tgcttgggtg     300
ttcggcggag gaaccaagct gacggtccta ggt                                   333
```

<210> SEQ ID NO 45
<211> LENGTH: 366
<212> TYPE: DNA
<213> ORGANISM: Mus musculus

<400> SEQUENCE: 45

```
gaggtgcagc tgttggagtc tgggggaggc ttggtacagc ctggggggtc cctgagactc      60
tcctgtgcag cctctggatt caccttcagt aatcatgaaa tgaattgggt ccgccaggct     120
ccagggaagg ggctggagtg ggtctcagct attagtggta gtggtggtag cacatactac     180
gcagactccg tgaagggccg gttcaccatc tccagagaca attccaagaa cacgctgtat     240
ctgcaaatga acagcctgag agccgaggac actgccgtgt attactgtgc gagagaagaa     300
tatacgattt tgggagccta ctactttgac ttctggggcc agggtacact ggtcaccgtg     360
agctca                                                                 366
```

<210> SEQ ID NO 46
<211> LENGTH: 336
<212> TYPE: DNA

<213> ORGANISM: Mus musculus

<400> SEQUENCE: 46

```
cagtctgtgc tgactcagcc accctcagcg tctgggaccc ccgggcagag ggtcaccatc    60
tcttgttctg gaagcagctc caacatcgaa agtagtactg taaactggta tcagcagctc   120
ccaggaacgg cccccaaact cctcatctat gacaataata agcgaccctc aggggtccct   180
gaccgattct ctggctccaa gtctggcacc tcagcctccc tggccatcag tgggctccgg   240
tccgaggatg aggctgatta ttactgccag tcatatgaca gtagcctgag tcctcttgtg   300
ctgttcggcg aggaaccaa gctgacggtc ctaggt                              336
```

<210> SEQ ID NO 47
<211> LENGTH: 357
<212> TYPE: DNA
<213> ORGANISM: Mus musculus

<400> SEQUENCE: 47

```
gaggtgcagc tgttggagtc tgggggaggc ttggtacagc ctgggggtc cctgagactc     60
tcctgtgcag cctctggatt caccttcagt gactactaca tgagctggat ccgccaggct   120
ccagggaagg ggctggagtg gtctcagct attagtggta gtggtggtag cacatactac   180
gcagactccg tgaagggccg gttcaccatc tccagagaca attccaagaa cacgctgtat   240
ctgcaaatga acagcctgag agccgaggac actgccgtgt attactgtgc gaaagaagat   300
tgggagggag cctcgtttga ctactggggc cagggtacac tggtcaccgt gagctca      357
```

<210> SEQ ID NO 48
<211> LENGTH: 333
<212> TYPE: DNA
<213> ORGANISM: Mus musculus

<400> SEQUENCE: 48

```
cagtctgtgc tgactcagcc accctcagcg tctgggaccc ccgggcagag ggtcaccatc    60
tcttgttctg gaagcagctc caacatcgga attaatactg taaactggta tcagcagctc   120
ccaggaacgg cccccaaact cctcatctat gacaataata agcgaccctc aggggtccct   180
gaccgattct ctggctccaa gtctggcacc tcagcctccc tggccatcag tgggctccgg   240
tccgaggatg aggctgatta ttactgtgca acatggatg acagcctgag tggttgggtg   300
ttcggcggag gaaccaagct gacggtccta ggt                                333
```

<210> SEQ ID NO 49
<211> LENGTH: 347
<212> TYPE: DNA
<213> ORGANISM: Mus musculus

<400> SEQUENCE: 49

```
gaggtgcagc tgttggagtc tgggggaggc ttggtacagc ctgggggtc cctgagactc     60
tcctgtgcag cctctggatt caccttcagt agctatagca tgaactgggt ccgccaggct   120
ccagggaagg ggctggagtg gtctcatcc attagtagta gtagtagtta catatactac   180
gcagactcag tgaagggccg attcaccatc tccagagaca attccaagaa cacgctgtat   240
ctgcaaatga acagcctgag agccgaggac actgccgtgt attactgtgc gagaaggggg   300
acgacttttg actactgggg ccagggacac tggtcaccgt gagctca                 347
```

<210> SEQ ID NO 50
<211> LENGTH: 336

```
<212> TYPE: DNA
<213> ORGANISM: Mus musculus

<400> SEQUENCE: 50
cagtctgtgc tgactcagcc accctcggcg tctgggaccc ccgggcagag ggtcaccatc    60
tcctgcactg ggagcaactc caacctcggg cacccttatg atgtacactg gtatcagcag   120
ctcccaggaa cggcccccaa actcctcatc tatagtgata atcagcggcc ctcaggggtc   180
cctgaccgat tctctggctc caagtctggc acctcagcct ccctggccat cagtgggctc   240
cggtccgagg atgaggctga ttattactgt ggaacatggg atgacagcct gagtggttgg   300
gtgttcggcg gaggaaccaa gctgacggtc ctaggt                             336

<210> SEQ ID NO 51
<211> LENGTH: 345
<212> TYPE: DNA
<213> ORGANISM: Mus musculus

<400> SEQUENCE: 51
gaggtgcagc tgttggagtc tgggggaggc ttggtacagc ctggggggtc cctgagactc    60
tcctgtgcag cctctggatt cacctttagc agctatgcca tgaactgggt ccgccaggct   120
ccagggaagg ggctggagtg gtatcgggt gttagttgga atggcagtag gacgcactat   180
gcagactctg tgaagggccg attcaccatc tccagagaca attccaagaa cacgctgtat   240
ctgcaaatga acagcctgag agccgaggac actgccgtgt attactgtgc gagtaacgca   300
cccttcgacc cctggggcca aggtacactg gtcaccgtga gctca                  345

<210> SEQ ID NO 52
<211> LENGTH: 333
<212> TYPE: DNA
<213> ORGANISM: Mus musculus

<400> SEQUENCE: 52
cagtctgtgc tgactcagcc accctcagcg tctgggaccc ccgggcagag ggtcaccatc    60
tcttgttctg gaagcagctc caacatcgga agtaattatg tatactggta tcagcagctc   120
ccaggaacgg cccccaaact cctcatctat gacaataata gcgaccctc agggtccct     180 gaccgattct ctggctccaa gtctggcacc tcagcctccc tggccatcag tgggctccgg   240
tccgaggatg aggctgatta ttactgccag tcctatgaca gcagcctgag tgctgtggta   300
ttcggcggag gaaccaagct gacggtccta ggt                                333

<210> SEQ ID NO 53
<211> LENGTH: 363
<212> TYPE: DNA
<213> ORGANISM: Mus musculus

<400> SEQUENCE: 53
gaggtgcagc tgttggagtc tgggggaggc ttggtacagc ctggggggtc cctgagactc    60
tcctgtgcag cctctggatt cacccttcaga gactatggca tgcactgggt ccgccaggct   120
ccaggcaagg ggctggagtg gtctcagct attagtggta gtggtggtag cacattctac   180
gcagactccg tgaagggccg gttcaccatc tccagagaca attccaagaa cacgctgtat   240
ctgcaaatga acagcctgag agccgaggac actgccgtgt attactgtgc gagaggccgg   300
tcggctggta gcatgggcta ctttgactac tggggccaag gtacactggt caccgtgagc   360
tca                                                                 363
```

<210> SEQ ID NO 54
<211> LENGTH: 336
<212> TYPE: DNA
<213> ORGANISM: Mus musculus

<400> SEQUENCE: 54

| | | | | | |
|---|---|---|---|---|---|
| cagtctgtgc | tgactcagcc | accctcagcg | tctgggaccc | ccgggcagag | ggtcaccatc | 60 |
| tcctgcactg | ggagcagctc | caacatcggg | gcaggttatg | atgtacactg | gtatcagcag | 120 |
| ctcccaggaa | cggcccccaa | actcctcatc | tatggtaaca | gcaatcggcc | ctcaggggtc | 180 |
| cctgaccgat | tcrctggctc | caagtctggc | acctcagcct | ccctggccat | cagtgggctc | 240 |
| cggtccgagg | atgaggctga | ttattactgt | gcagcatggg | atgacagtct | gaatggttgg | 300 |
| gtgttcggcg | gaggaaccaa | gctgacggtc | ctaggt | | | 336 |

<210> SEQ ID NO 55
<211> LENGTH: 351
<212> TYPE: DNA
<213> ORGANISM: Mus musculus

<400> SEQUENCE: 55

| | | | | | |
|---|---|---|---|---|---|
| gaggtgcagc | tgttggagtc | tgggggaggc | ttggtacagc | ctgggggggtc | cctgagactc | 60 |
| tcctgtgcag | cctctggatt | caccttcagt | agcaactaca | tgagctgggt | ccgccaggct | 120 |
| ccagggaagg | ggctggagtg | ggtctcaact | gttagtgctg | gtggtggtag | cacattctac | 180 |
| gcagactccg | tgaagggccg | gttcaccatc | tccagagaca | attccaagaa | cacgctgtat | 240 |
| ctgcaaatga | acagcctgag | agccgaggac | actgccgtgt | attactgtgc | gagaggccaa | 300 |
| gatggggcca | atgactactg | gggccaaggt | acactggtca | ccgtgagctc | a | 351 |

<210> SEQ ID NO 56
<211> LENGTH: 336
<212> TYPE: DNA
<213> ORGANISM: Mus musculus

<400> SEQUENCE: 56

| | | | | | |
|---|---|---|---|---|---|
| cagtctgtgc | tgactcagcc | accctcagcg | tctgggaccc | ccgggcagag | ggtcaccatc | 60 |
| tcctgcactg | ggagcagctc | caacatcggg | gcaggttatg | atgtactctg | gtatcagcag | 120 |
| ctctcaggaa | cggcccccaa | actcctcatc | tatagtaata | atcagcggcc | ctcaggggtc | 180 |
| cctgaccgat | tctctggctc | caagtctggc | acctcagcct | ccctggccat | cagtggggctc | 240 |
| cggtccgagg | atgaggctga | ttattactgt | gcatcatggg | atgacagcct | gagtggtccg | 300 |
| gtgttcggcg | gaggaaccaa | gctgacggtc | ctaggt | | | 336 |

<210> SEQ ID NO 57
<211> LENGTH: 14
<212> TYPE: PRT
<213> ORGANISM: Mus musculus

<400> SEQUENCE: 57

Phe Ser Asn Tyr Trp Met His Trp Val Arg Gln Ala Pro Gly
1               5                   10

<210> SEQ ID NO 58
<211> LENGTH: 19
<212> TYPE: PRT
<213> ORGANISM: Mus musculus

<400> SEQUENCE: 58

-continued

Ser Ala Ile Ser Gly Ser Gly Gly Ser Thr Tyr Tyr Ala Asp Ser Val
1               5                   10                  15

Lys Gly Arg

<210> SEQ ID NO 59
<211> LENGTH: 11
<212> TYPE: PRT
<213> ORGANISM: Mus musculus

<400> SEQUENCE: 59

Ala Arg Gln Gly Arg Ala Val Thr Leu Asp Tyr
1               5                   10

<210> SEQ ID NO 60
<211> LENGTH: 14
<212> TYPE: PRT
<213> ORGANISM: Mus musculus

<400> SEQUENCE: 60

Cys Ser Gly Ser Arg Ser Asn Ile Gly Ser Asn Ser Val His
1               5                   10

<210> SEQ ID NO 61
<211> LENGTH: 7
<212> TYPE: PRT
<213> ORGANISM: Mus musculus

<400> SEQUENCE: 61

Ser Asn Asn Gln Arg Pro Ser
1               5

<210> SEQ ID NO 62
<211> LENGTH: 11
<212> TYPE: PRT
<213> ORGANISM: Mus musculus

<400> SEQUENCE: 62

Cys Ser Ser Tyr Thr Ser Ser Thr Leu Leu
1               5                   10

<210> SEQ ID NO 63
<211> LENGTH: 14
<212> TYPE: PRT
<213> ORGANISM: Mus musculus

<400> SEQUENCE: 63

Phe Ser Ser Tyr Asp Met Ala Trp Val Arg Gln Ala Pro Gly
1               5                   10

<210> SEQ ID NO 64
<211> LENGTH: 19
<212> TYPE: PRT
<213> ORGANISM: Mus musculus

<400> SEQUENCE: 64

Ser Gly Val Ser Trp Asn Gly Ser Arg Thr His Tyr Ala Asp Ser Val
1               5                   10                  15

Lys Gly Arg

<210> SEQ ID NO 65
<211> LENGTH: 16
<212> TYPE: PRT
<213> ORGANISM: Mus musculus

```
<400> SEQUENCE: 65

Ala Arg Asp Gln Asp Leu Ser Gly Trp Tyr Pro Gly Tyr Phe Asp Tyr
1               5                   10                  15

<210> SEQ ID NO 66
<211> LENGTH: 14
<212> TYPE: PRT
<213> ORGANISM: Mus musculus

<400> SEQUENCE: 66

Cys Ser Gly Ser Ser Asp Met Gly Asn Tyr Ala Val Ser
1               5                   10

<210> SEQ ID NO 67
<211> LENGTH: 7
<212> TYPE: PRT
<213> ORGANISM: Mus musculus

<400> SEQUENCE: 67

Gly Asn Ser Asn Arg Pro Ser
1               5

<210> SEQ ID NO 68
<211> LENGTH: 11
<212> TYPE: PRT
<213> ORGANISM: Mus musculus

<400> SEQUENCE: 68

Cys Ser Ser Tyr Thr Ser Ser Arg Thr Val Val
1               5                   10

<210> SEQ ID NO 69
<211> LENGTH: 14
<212> TYPE: PRT
<213> ORGANISM: Mus musculus

<400> SEQUENCE: 69

Phe Ser Ser Tyr Ala Met Ser Trp Val Arg Gln Ala Pro Gly
1               5                   10

<210> SEQ ID NO 70
<211> LENGTH: 18
<212> TYPE: PRT
<213> ORGANISM: Mus musculus

<400> SEQUENCE: 70

Ser Ala Ile Gly Ala Gly Gly Gly Thr Tyr Tyr Ala Asp Ser Val Lys
1               5                   10                  15

Gly Arg

<210> SEQ ID NO 71
<211> LENGTH: 11
<212> TYPE: PRT
<213> ORGANISM: Mus musculus

<400> SEQUENCE: 71

Ala Ser Gly Gly Ser Trp Glu Leu Pro Asp Tyr
1               5                   10

<210> SEQ ID NO 72
<211> LENGTH: 14
<212> TYPE: PRT
<213> ORGANISM: Mus musculus
```

<400> SEQUENCE: 72

Cys Ser Gly Ser Ser Ser Asn Ile Gly Ser Asn Thr Val Asn
1               5                   10

<210> SEQ ID NO 73
<211> LENGTH: 7
<212> TYPE: PRT
<213> ORGANISM: Mus musculus

<400> SEQUENCE: 73

Tyr Asp Asp Leu Leu Pro Ser
1               5

<210> SEQ ID NO 74
<211> LENGTH: 12
<212> TYPE: PRT
<213> ORGANISM: Mus musculus

<400> SEQUENCE: 74

Cys Ser Ser His Thr Thr Thr Ser Thr Phe Trp Val
1               5                   10

<210> SEQ ID NO 75
<211> LENGTH: 14
<212> TYPE: PRT
<213> ORGANISM: Mus musculus

<400> SEQUENCE: 75

Phe Ser Pro Tyr Ser Met Asn Trp Val Arg Gln Ala Pro Gly
1               5                   10

<210> SEQ ID NO 76
<211> LENGTH: 19
<212> TYPE: PRT
<213> ORGANISM: Mus musculus

<400> SEQUENCE: 76

Ser Ser Ile Ser Ser Ser Ser Thr Ile Tyr Tyr Ala Asp Ser Val Lys
1               5                   10                  15

Gly Arg Phe

<210> SEQ ID NO 77
<211> LENGTH: 9
<212> TYPE: PRT
<213> ORGANISM: Mus musculus

<400> SEQUENCE: 77

Ala Arg Lys Thr Leu Ala Leu Asp Ile
1               5

<210> SEQ ID NO 78
<211> LENGTH: 15
<212> TYPE: PRT
<213> ORGANISM: Mus musculus

<400> SEQUENCE: 78

Cys Thr Gly Ser Ser Ser Asn Ile Gly Ala Arg Tyr Asp Val His
1               5                   10                  15

<210> SEQ ID NO 79
<211> LENGTH: 7
<212> TYPE: PRT
<213> ORGANISM: Mus musculus

<400> SEQUENCE: 79

Ser Asp Asp Gln Arg Pro Ser
1               5

<210> SEQ ID NO 80
<211> LENGTH: 12
<212> TYPE: PRT
<213> ORGANISM: Mus musculus

<400> SEQUENCE: 80

Cys Gln Ser Tyr Asp Ser Ser Leu Ser Gly Trp Val
1               5                   10

<210> SEQ ID NO 81
<211> LENGTH: 14
<212> TYPE: PRT
<213> ORGANISM: Mus musculus

<400> SEQUENCE: 81

Phe Ser Asn Ala Trp Met Ser Trp Val Arg Gln Ala Pro Gly
1               5                   10

<210> SEQ ID NO 82
<211> LENGTH: 19
<212> TYPE: PRT
<213> ORGANISM: Mus musculus

<400> SEQUENCE: 82

Ser Gly Ile Thr Gly Ser Gly Asp Ser Thr Tyr Tyr Ala Asp Ser Val
1               5                   10                  15

Lys Gly Arg

<210> SEQ ID NO 83
<211> LENGTH: 12
<212> TYPE: PRT
<213> ORGANISM: Mus musculus

<400> SEQUENCE: 83

Ala Thr Gly Gly Asp Thr Ser Gly Tyr Gly Pro His
1               5                   10

<210> SEQ ID NO 84
<211> LENGTH: 14
<212> TYPE: PRT
<213> ORGANISM: Mus musculus

<400> SEQUENCE: 84

Cys Ser Gly Ser Ser Ser Asn Ile Gly Ser Asn Tyr Val Tyr
1               5                   10

<210> SEQ ID NO 85
<211> LENGTH: 7
<212> TYPE: PRT
<213> ORGANISM: Mus musculus

<400> SEQUENCE: 85

Asp Asn Asn Lys Arg Pro Ser
1               5

<210> SEQ ID NO 86
<211> LENGTH: 12
<212> TYPE: PRT
<213> ORGANISM: Mus musculus

<400> SEQUENCE: 86

Cys Gln Ser Tyr Asp Asp Thr Leu Ser Val Val Val
1               5                   10

<210> SEQ ID NO 87
<211> LENGTH: 14
<212> TYPE: PRT
<213> ORGANISM: Mus musculus

<400> SEQUENCE: 87

Phe Ser Asp Tyr Tyr Met Ser Trp Ile Arg Gln Ala Pro Gly
1               5                   10

<210> SEQ ID NO 88
<211> LENGTH: 19
<212> TYPE: PRT
<213> ORGANISM: Mus musculus

<400> SEQUENCE: 88

Ala Ile Ile Ser Tyr Asp Gly Ser Asn Glu Tyr Tyr Ala Asp Ser Val
1               5                   10                  15

Lys Gly Arg

<210> SEQ ID NO 89
<211> LENGTH: 23
<212> TYPE: PRT
<213> ORGANISM: Mus musculus

<400> SEQUENCE: 89

Ala Thr Ser Ser Gly Asp Gly Gly Trp Glu Asp Trp Gly Pro Pro Tyr
1               5                   10                  15

Tyr Tyr Tyr Gly Met Asp Val
            20

<210> SEQ ID NO 90
<211> LENGTH: 15
<212> TYPE: PRT
<213> ORGANISM: Mus musculus

<400> SEQUENCE: 90

Cys Thr Gly Ser Ser Ser Asn Leu Gly Ala Gly Tyr Ala Val His
1               5                   10                  15

<210> SEQ ID NO 91
<211> LENGTH: 7
<212> TYPE: PRT
<213> ORGANISM: Mus musculus

<400> SEQUENCE: 91

Gly Asn Thr Asn Arg Pro Ser
1               5

<210> SEQ ID NO 92
<211> LENGTH: 12
<212> TYPE: PRT
<213> ORGANISM: Mus musculus

<400> SEQUENCE: 92

Cys Ala Ala Trp Asp Asp Ser Leu Arg Gly Pro Val
1               5                   10

<210> SEQ ID NO 93
<211> LENGTH: 14

```
<212> TYPE: PRT
<213> ORGANISM: Mus musculus

<400> SEQUENCE: 93

Phe Ser Ser Tyr Ala Met Ser Trp Val Arg Gln Ala Pro Gly
1               5                   10

<210> SEQ ID NO 94
<211> LENGTH: 18
<212> TYPE: PRT
<213> ORGANISM: Mus musculus

<400> SEQUENCE: 94

Ser Val Ile Tyr Ser Gly Gly Ser Thr Tyr Tyr Ala Asp Ser Val Lys
1               5                   10                  15

Gly Arg

<210> SEQ ID NO 95
<211> LENGTH: 15
<212> TYPE: PRT
<213> ORGANISM: Mus musculus

<400> SEQUENCE: 95

Ala Arg Asp Ser Trp Glu Leu Leu Gly Tyr Asp Ala Phe Asp Leu
1               5                   10                  15

<210> SEQ ID NO 96
<211> LENGTH: 14
<212> TYPE: PRT
<213> ORGANISM: Mus musculus

<400> SEQUENCE: 96

Cys Ser Gly Ser Ser Asn Ile Gly Ser Asn Tyr Val Tyr
1               5                   10

<210> SEQ ID NO 97
<211> LENGTH: 7
<212> TYPE: PRT
<213> ORGANISM: Mus musculus

<400> SEQUENCE: 97

Gly Asp Ser Asn Arg Pro Ser
1               5

<210> SEQ ID NO 98
<211> LENGTH: 12
<212> TYPE: PRT
<213> ORGANISM: Mus musculus

<400> SEQUENCE: 98

Cys Gly Thr Trp Asp Ser Ser Leu Ser Ala Trp Val
1               5                   10

<210> SEQ ID NO 99
<211> LENGTH: 14
<212> TYPE: PRT
<213> ORGANISM: Mus musculus

<400> SEQUENCE: 99

Phe Ser Asn His Glu Met Asn Trp Val Arg Gln Ala Pro Gly
1               5                   10

<210> SEQ ID NO 100
<211> LENGTH: 19
```

```
<212> TYPE: PRT
<213> ORGANISM: Mus musculus

<400> SEQUENCE: 100

Ser Ala Ile Ser Gly Ser Gly Gly Ser Thr Tyr Tyr Ala Asp Ser Val
1               5                   10                  15

Lys Gly Arg

<210> SEQ ID NO 101
<211> LENGTH: 15
<212> TYPE: PRT
<213> ORGANISM: Mus musculus

<400> SEQUENCE: 101

Ala Arg Glu Glu Tyr Thr Ile Leu Gly Ala Tyr Tyr Phe Asp Phe
1               5                   10                  15

<210> SEQ ID NO 102
<211> LENGTH: 14
<212> TYPE: PRT
<213> ORGANISM: Mus musculus

<400> SEQUENCE: 102

Cys Ser Gly Ser Ser Ser Asn Ile Glu Ser Ser Thr Val Asn
1               5                   10

<210> SEQ ID NO 103
<211> LENGTH: 7
<212> TYPE: PRT
<213> ORGANISM: Mus musculus

<400> SEQUENCE: 103

Asp Asn Asn Lys Arg Pro Ser
1               5

<210> SEQ ID NO 104
<211> LENGTH: 13
<212> TYPE: PRT
<213> ORGANISM: Mus musculus

<400> SEQUENCE: 104

Cys Gln Ser Tyr Asp Ser Ser Leu Ser Pro Leu Val Leu
1               5                   10

<210> SEQ ID NO 105
<211> LENGTH: 14
<212> TYPE: PRT
<213> ORGANISM: Mus musculus

<400> SEQUENCE: 105

Phe Ser Asp Tyr Tyr Met Ser Trp Ile Arg Gln Ala Pro Gly
1               5                   10

<210> SEQ ID NO 106
<211> LENGTH: 19
<212> TYPE: PRT
<213> ORGANISM: Mus musculus

<400> SEQUENCE: 106

Ser Ala Ile Ser Gly Ser Gly Gly Ser Thr Tyr Tyr Ala Asp Ser Val
1               5                   10                  15

Lys Gly Arg
```

```
<210> SEQ ID NO 107
<211> LENGTH: 12
<212> TYPE: PRT
<213> ORGANISM: Mus musculus

<400> SEQUENCE: 107

Ala Lys Glu Asp Trp Glu Gly Ala Ser Phe Asp Tyr
1               5                   10

<210> SEQ ID NO 108
<211> LENGTH: 14
<212> TYPE: PRT
<213> ORGANISM: Mus musculus

<400> SEQUENCE: 108

Cys Ser Gly Ser Ser Asn Ile Gly Ile Asn Thr Val Asn
1               5                   10

<210> SEQ ID NO 109
<211> LENGTH: 7
<212> TYPE: PRT
<213> ORGANISM: Mus musculus

<400> SEQUENCE: 109

Asp Asn Asn Lys Arg Pro Ser
1               5

<210> SEQ ID NO 110
<211> LENGTH: 12
<212> TYPE: PRT
<213> ORGANISM: Mus musculus

<400> SEQUENCE: 110

Cys Ala Thr Trp Asp Asp Ser Leu Ser Gly Trp Val
1               5                   10

<210> SEQ ID NO 111
<211> LENGTH: 14
<212> TYPE: PRT
<213> ORGANISM: Mus musculus

<400> SEQUENCE: 111

Phe Ser Ser Tyr Ser Met Asn Trp Val Arg Gln Ala Pro Gly
1               5                   10

<210> SEQ ID NO 112
<211> LENGTH: 19
<212> TYPE: PRT
<213> ORGANISM: Mus musculus

<400> SEQUENCE: 112

Ser Ser Ile Ser Ser Ser Ser Tyr Ile Tyr Ala Asp Ser Val
1               5                   10                  15

Lys Gly Arg

<210> SEQ ID NO 113
<211> LENGTH: 9
<212> TYPE: PRT
<213> ORGANISM: Mus musculus

<400> SEQUENCE: 113

Ala Arg Arg Gly Thr Thr Phe Asp Tyr
1               5
```

```
<210> SEQ ID NO 114
<211> LENGTH: 15
<212> TYPE: PRT
<213> ORGANISM: Mus musculus

<400> SEQUENCE: 114

Cys Thr Gly Ser Asn Ser Asn Leu Gly Ala Pro Tyr Asp Val His
1               5                   10                  15

<210> SEQ ID NO 115
<211> LENGTH: 7
<212> TYPE: PRT
<213> ORGANISM: Mus musculus

<400> SEQUENCE: 115

Ser Asp Asn Gln Arg Pro Ser
1               5

<210> SEQ ID NO 116
<211> LENGTH: 12
<212> TYPE: PRT
<213> ORGANISM: Mus musculus

<400> SEQUENCE: 116

Cys Gly Thr Trp Asp Asp Ser Leu Ser Gly Trp Val
1               5                   10

<210> SEQ ID NO 117
<211> LENGTH: 14
<212> TYPE: PRT
<213> ORGANISM: Mus musculus

<400> SEQUENCE: 117

Phe Ser Ser Tyr Ala Met Asn Trp Val Arg Gln Ala Pro Gly
1               5                   10

<210> SEQ ID NO 118
<211> LENGTH: 19
<212> TYPE: PRT
<213> ORGANISM: Mus musculus

<400> SEQUENCE: 118

Ser Gly Val Ser Trp Asn Gly Ser Arg Thr His Tyr Ala Asp Ser Val
1               5                   10                  15

Lys Gly Arg

<210> SEQ ID NO 119
<211> LENGTH: 8
<212> TYPE: PRT
<213> ORGANISM: Mus musculus

<400> SEQUENCE: 119

Ala Ser Asn Ala Pro Phe Asp Pro
1               5

<210> SEQ ID NO 120
<211> LENGTH: 14
<212> TYPE: PRT
<213> ORGANISM: Mus musculus

<400> SEQUENCE: 120

Cys Ser Gly Ser Ser Asn Ile Gly Ser Asn Tyr Val Tyr
1               5                   10
```

```
<210> SEQ ID NO 121
<211> LENGTH: 7
<212> TYPE: PRT
<213> ORGANISM: Mus musculus

<400> SEQUENCE: 121

Asp Asn Asn Lys Arg Pro Ser
1               5

<210> SEQ ID NO 122
<211> LENGTH: 12
<212> TYPE: PRT
<213> ORGANISM: Mus musculus

<400> SEQUENCE: 122

Cys Gln Ser Tyr Asp Ser Ser Leu Ser Ala Val Val
1               5                   10

<210> SEQ ID NO 123
<211> LENGTH: 14
<212> TYPE: PRT
<213> ORGANISM: Mus musculus

<400> SEQUENCE: 123

Phe Arg Asp Tyr Gly Met His Trp Val Arg Gln Ala Pro Gly
1               5                   10

<210> SEQ ID NO 124
<211> LENGTH: 19
<212> TYPE: PRT
<213> ORGANISM: Mus musculus

<400> SEQUENCE: 124

Ser Ala Ile Ser Gly Ser Gly Gly Ser Thr Phe Tyr Ala Asp Ser Val
1               5                   10                  15

Lys Gly Arg

<210> SEQ ID NO 125
<211> LENGTH: 14
<212> TYPE: PRT
<213> ORGANISM: Mus musculus

<400> SEQUENCE: 125

Ala Arg Gly Arg Ser Ala Gly Ser Met Gly Tyr Phe Asp Tyr
1               5                   10

<210> SEQ ID NO 126
<211> LENGTH: 15
<212> TYPE: PRT
<213> ORGANISM: Mus musculus

<400> SEQUENCE: 126

Cys Thr Gly Ser Ser Ser Asn Ile Gly Ala Gly Tyr Asp Val His
1               5                   10                  15

<210> SEQ ID NO 127
<211> LENGTH: 7
<212> TYPE: PRT
<213> ORGANISM: Mus musculus

<400> SEQUENCE: 127

Gly Asn Ser Asn Arg Pro Ser
1               5
```

```
<210> SEQ ID NO 128
<211> LENGTH: 12
<212> TYPE: PRT
<213> ORGANISM: Mus musculus

<400> SEQUENCE: 128

Cys Ala Ala Trp Asp Asp Ser Leu Asn Gly Trp Val
1               5                   10

<210> SEQ ID NO 129
<211> LENGTH: 14
<212> TYPE: PRT
<213> ORGANISM: Mus musculus

<400> SEQUENCE: 129

Phe Ser Asp Tyr Tyr Met Ser Trp Val Arg Gln Ala Pro Gly
1               5                   10

<210> SEQ ID NO 130
<211> LENGTH: 19
<212> TYPE: PRT
<213> ORGANISM: Mus musculus

<400> SEQUENCE: 130

Ala Ile Ile Ser Tyr Asp Gly Asn Glu Asn Tyr Tyr Ala Asp Ser Val
1               5                   10                  15

Lys Gly Arg

<210> SEQ ID NO 131
<211> LENGTH: 14
<212> TYPE: PRT
<213> ORGANISM: Mus musculus

<400> SEQUENCE: 131

Ala Arg Glu Asp Ile Asp Tyr Ala Asp Asp Ala Tyr Asp Ile
1               5                   10

<210> SEQ ID NO 132
<211> LENGTH: 15
<212> TYPE: PRT
<213> ORGANISM: Mus musculus

<400> SEQUENCE: 132

Cys Thr Gly Ser Ser Ser Asn Ile Gly Ala Gly Tyr Asp Val Leu
1               5                   10                  15

<210> SEQ ID NO 133
<211> LENGTH: 7
<212> TYPE: PRT
<213> ORGANISM: Mus musculus

<400> SEQUENCE: 133

Ser Asn Asn Gln Arg Pro Ser
1               5

<210> SEQ ID NO 134
<211> LENGTH: 12
<212> TYPE: PRT
<213> ORGANISM: Mus musculus

<400> SEQUENCE: 134

Cys Ala Ser Trp Asp Asp Ser Leu Ser Gly Pro Val
1               5                   10
```